(12) United States Patent
Slobodkin et al.

(10) Patent No.: US 8,900,621 B2
(45) Date of Patent: Dec. 2, 2014

(54) POLYAMINE DERIVATIVES

(71) Applicant: CLSN Laboratories, Inc., Wilmington, DE (US)

(72) Inventors: Gregory Slobodkin, Huntsville, AL (US); Richard Congo, Huntsville, AL (US); Majed Matar, Madison, AL (US); Jason Fewell, Madison, AL (US); Khursheed Anwer, Madison, AL (US); Brian Jeffery Sparks, Huntsville, AL (US)

(73) Assignee: CLSN Laboratories, Inc., Wilmington, DE (US)

( * ) Notice: Subject to any disclaimer, the term of this patent is extended or adjusted under 35 U.S.C. 154(b) by 0 days.

(21) Appl. No.: 13/790,980

(22) Filed: Mar. 8, 2013

(65) Prior Publication Data

US 2014/0050775 A1  Feb. 20, 2014

Related U.S. Application Data

(62) Division of application No. 12/727,987, filed on Mar. 19, 2010, now Pat. No. 8,460,696.

(60) Provisional application No. 61/161,828, filed on Mar. 20, 2009.

(51) Int. Cl.

| | | |
|---|---|---|
| A61F 2/00 | (2006.01) | |
| A61K 47/16 | (2006.01) | |
| A61K 31/713 | (2006.01) | |
| C07C 233/38 | (2006.01) | |
| C07C 235/10 | (2006.01) | |
| C07C 235/60 | (2006.01) | |
| A61K 47/48 | (2006.01) | |
| A61K 9/127 | (2006.01) | |
| C07D 475/04 | (2006.01) | |
| C07H 15/10 | (2006.01) | |
| C07K 7/23 | (2006.01) | |
| C07K 7/64 | (2006.01) | |

(52) U.S. Cl.
CPC ............ *A61K 31/713* (2013.01); *C07C 233/38* (2013.01); *C07C 235/10* (2013.01); *C07C 235/60* (2013.01); *A61K 47/16* (2013.01); *A61K 47/48061* (2013.01); *A61K 47/48946* (2013.01); *A61K 9/1272* (2013.01); *C07D 475/04* (2013.01); *C07H 15/10* (2013.01); *C07K 7/23* (2013.01); *C07K 7/64* (2013.01); *A61K 47/48815* (2013.01)

USPC .............. 424/426; 424/490; 554/58; 554/258

(58) Field of Classification Search
USPC .............................. 424/426, 490; 554/58, 528
See application file for complete search history.

(56) References Cited

U.S. PATENT DOCUMENTS

| 2,580,880 A | 1/1952 | Bird et al. | |
|---|---|---|---|
| 2008/0089924 A1* | 4/2008 | Nojima et al. | 424/439 |

FOREIGN PATENT DOCUMENTS

| EP | WO2007/045303 | * 4/2007 | ............... A61K 6/00 |
|---|---|---|---|
| JP | 6 016608 | 1/1994 | |
| JP | 6 345704 | 12/1994 | |
| JP | 7 018569 | 1/1995 | |
| JP | 7 018571 | 1/1995 | |
| JP | 10 001869 | 1/1998 | |
| WO | 89-08098 | 9/1989 | |
| WO | 00-30444 | 6/2000 | |
| WO | 03-106636 | 12/2003 | |
| WO | 2007/045303 | 4/2007 | |

OTHER PUBLICATIONS

Scanu, David et al., "Polar and Electrooptical Properties of [60]Fullerene-Containing Poly(benzylether) Dendrimers in Solution" Database Caplus [online], Chemical Abstracts Service, Columbus Ohio, US; XP002614842.

Thomas E. W. et al., "Cholesterol lowering bile acid binding agents: Novel Lipophilic polyamines" (1992) Journal of Medicinal Chemistry, American Chemical Society, vol. 35, No. 7, pp. 1233-1245.

Gray et al., "Polymer-based siRNA delivery: Perspectives on the fundamental and phenomenological distinctions from polymer-based DNA delivery" Journal of Controlled Release 121 (2007), pp. 64-73.

Wooddell et al., "Long-term RNA interference from optimized siRNA expression constructs in adult mice" Biochemical and Biophysical Research Communications 334 (2005), pp. 117-127.

Carmell et al., "RNase III enzymes and the initiation of gene silencing" Nature Structural & Molecular Biology (2004), vol. 11(3), pp. 91-92.

* cited by examiner

*Primary Examiner* — Anoop Singh
*Assistant Examiner* — Anna Falkowitz
(74) *Attorney, Agent, or Firm* — Sterne, Kessler, Goldstein & Fox P.L.L.C.

(57) ABSTRACT

Disclosed are compounds, compositions and methods for systemic and local delivery of biologically active molecules.

8 Claims, 10 Drawing Sheets

POLYAMINE DERIVATIVES

CROSS-REFERENCE TO RELATED APPLICATIONS

This application is a divisional of U.S. patent application Ser. No. 12/727,987, filed Mar. 19, 2010, now U.S. Pat. No. 8,460,696, which claims the benefit of U.S. Provisional Application No. 61/161,828, filed Mar. 20, 2009, the disclosures of which are incorporated herein by reference in their entireties.

BACKGROUND OF THE INVENTION

1. Field of the Invention

The invention relates to symmetrical polyamine derivatives and formulations comprising such compounds, and more specifically to polyamine derivatives that are partially acylated and optionally carry an auxiliary group. Such compounds are useful in introducing siRNA into a cell, in silencing expression of a target sequence, in delivering in vivo of siRNA, and in treating diseases and/or disorders.

2. Description of the Related Art

The compounds, compositions and methods of the invention are useful in therapeutic, research, and diagnostic applications that rely upon the efficient transfer of biologically active molecules into cells, tissues, and organs. The discussion is provided only for understanding of the invention that follows.

The cellular delivery of various therapeutic compounds, such as antiviral and chemotherapeutic agents, is usually compromised by two limitations. First, the selectivity of a number of therapeutic agents is often low, resulting in high toxicity to normal tissues. Secondly, the trafficking of many compounds into living cells is highly restricted by the complex membrane systems of the cell. Specific transporters allow the selective entry of nutrients or regulatory molecules, while excluding most exogenous molecules such as nucleic acids and proteins. Various strategies can be used to improve transport of compounds into cells, including the use of lipid carriers, biodegradable polymers, and various conjugate systems.

The most well studied approaches for improving the transport of foreign nucleic acids into cells involve the use of viral vectors or cationic lipids and related cytofectins. Viral vectors can be used to transfer genes efficiently into some cell types, but they generally cannot be used to introduce chemically synthesized molecules into cells. An alternative approach is to use delivery formulations incorporating cationic lipids, which interact with nucleic acids through one end and lipids or membrane systems through another. Synthetic nucleic acids as well as plasmids can be delivered using the cytofectins, although the utility of such compounds is often limited by cell-type specificity, requirement for low serum during transfection, and toxicity.

Another approach to delivering biologically active molecules involves the use of conjugates. Conjugates are often selected based on the ability of certain molecules to be selectively transported into specific cells, for example via receptor-mediated endocytosis. By attaching a compound of interest to molecules that are actively transported across the cellular membranes, the effective transfer of that compound into cells or specific cellular organelles can be realized. Alternatively, molecules that are able to penetrate cellular membranes without active transport mechanisms, for example, various lipophilic molecules, can be used to deliver compounds of interest. Examples of molecules that can be utilized as conjugates include but are not limited to peptides, hormones, fatty acids, vitamins, flavonoids, sugars, reporter molecules, reporter enzymes, chelators, porphyrins, intercalators, and other molecules that are capable of penetrating cellular membranes, either by active transport or passive transport.

The delivery of compounds to specific cell types, for example, cancer cells or cells specific to particular tissues and organs, can be accomplished by utilizing receptors associated with specific cell types. Particular receptors are overexpressed in certain cancerous cells, including the high affinity folic acid receptor. For example, the high affinity folate receptor is a tumor marker that is overexpressed in a variety of neoplastic tissues, including breast, ovarian, cervical, colorectal, renal, and nasopharyngeal tumors, but is expressed to a very limited extent in normal tissues. The use of folic acid based conjugates to transport exogenous compounds across cell membranes can provide a targeted delivery approach to the treatment and diagnosis of disease and can provide a reduction in the required dose of therapeutic compounds. Furthermore, therapeutic bioavailability, pharmacodynamics, and pharmacokinetic parameters can be modulated through the use of bioconjugates, including folate bioconjugates. The synthesis of biologically active pteroyloligo-L-glutamates has been reported. A method for the solid phase synthesis of certain oligonucleotide-folate conjugates has been described, as well as oligonucleotides modified with specific conjugate groups. The use of biotin and folate conjugates to enhance transmembrane transport of exogenous molecules, including specific oligonucleotides has been reported. Certain folate conjugates, including specific nucleic acid folate conjugates with a phosphoramidite moiety attached to the nucleic acid component of the conjugate, and methods for the synthesis of these folate conjugates have been described. The synthesis of an intermediate, alpha-[2-(trimethylsilyl)ethoxycarbonyl]folic acid, useful in the synthesis of certain types of folate-nucleoside conjugates has been reported.

The delivery of compounds to other cell types can be accomplished by utilizing receptors associated with a certain type of cell, such as hepatocytes. For example, drug delivery systems utilizing receptor-mediated endocytosis have been employed to achieve drug targeting as well as drug-uptake enhancement. The asialoglycoprotein receptor (ASGPr) is unique to hepatocytes and binds branched galactose-terminal glycoproteins, such as asialoorosomucoid (ASOR). Binding of such glycoproteins or synthetic glycoconjugates to the receptor takes place with an affinity that strongly depends on the degree of branching of the oligosaccharide chain, for example, triatennary structures are bound with greater affinity than biatenarry or monoatennary chains (example of this high specificity through the use of N-acetyl-D-galactosamine as the carbohydrate moiety, which has higher affinity for the receptor, compared to galactose). This "clustering effect" has also been described for the binding and uptake of mannosyl-terminating glycoproteins or glycoconjugates. The use of galactose and galactosamine based conjugates to transport exogenous compounds across cell membranes can provide a targeted delivery approach to the treatment of liver disease such as HBV and HCV infection or hepatocellular carcinoma. The use of bioconjugates can also provide a reduction in the required dose of therapeutic compounds required for treatment. Furthermore, therapeutic bioavailability, pharmacodynamics, and pharmacokinetic parameters can be modulated through the use of bioconjugates.

A number of peptide based cellular transporters have been developed by several research groups. These peptides are capable of crossing cellular membranes in vitro and in vivo with high efficiency. Examples of such fusogenic peptides include a 16-amino acid fragment of the homeodomain of ANTENNAPEDIA, a *Drosophila* transcription factor; a 17-mer fragment representing the hydrophobic region of the signal sequence of Kaposi fibroblast growth factor with or without NLS domain; a 17-mer signal peptide sequence of caiman crocodylus Ig(5) light chain; a 17-amino acid fusion sequence of HIV envelope glycoprotein gp4114; the HIV-1 Tat49-57 fragment; a transportan A—achimeric 27-mer consisting of N-terminal fragment of neuropeptide galanine and membrane interacting wasp venom peptide mastoporan; and a 24-mer derived from influenza virus hemagglutinin envelope glycoprotein. These peptides were successfully used as part of an antisense oligodeoxyribonucleotide-peptide conjugate for cell culture transfection without lipids. In a number of cases, such conjugates demonstrated better cell culture efficacy then parent oligonucleotides transfected using lipid delivery. In addition, use of phage display techniques has identified several organ targeting and tumor targeting peptides in vivo. Conjugation of tumor targeting peptides to doxorubicin has been shown to significantly improve the toxicity profile and has demonstrated enhanced efficacy of doxorubicin in the in vivo murine cancer model MDA-MB-435 breast carcinoma.

Another approach to the intracellular delivery of biologically active molecules involves the use of cationic polymers (for example, the use of high molecular weight lysine polymers for increasing the transport of various molecules across cellular membranes has been described). Certain methods and compositions for transporting drugs and macromolecules across biological membranes in which the drug or macromolecule is covalently attached to a transport polymer consisting of from 6 to 25 subunits, at least 50% of which contain a guanidine or amidine side chain have been disclosed. The transport polymers are preferably polyarginine peptides composed of all D-, all L- or mixtures of D- and L-arginine. Described also are certain poly-lysine and poly-arginine compounds for the delivery of drugs and other agents across epithelial tissues, including the skin, gastrointestinal tract, pulmonary epithelium and blood-brain barrier. Certain polyarginine compounds and certain poly-lysine and polyarginine compounds for intra-ocular delivery of drugs have also been disclosed. Certain cyclodextran polymers compositions that include a cross-linked cationic polymer component and certain lipid based formulations have been disclosed.

Another approach to the intracellular delivery of biologically active molecules involves the use of liposomes or other particle forming compositions. Since the first description of liposomes in 1965, there has been a sustained interest and effort in the area of developing lipid-based carrier systems for the delivery of pharmaceutically active compounds. Liposomes are attractive drug carriers since they protect biological molecules from degradation while improving their cellular uptake. One of the most commonly used classes of liposome formulations for delivering polyanions (e.g., DNA) is that which contains cationic lipids. Lipid aggregates can be formed with macromolecules using cationic lipids alone or including other lipids and amphiphiles such as phosphatidylethanolamine. It is well known in the art that both the composition of the lipid formulation as well as its method of preparation have effect on the structure and size of the resultant anionic macromolecule-cationic lipid aggregate. These factors can be modulated to optimize delivery of polyanions to specific cell types in vitro and in vivo. The use of cationic lipids for cellular delivery of biologically active molecules has several advantages. The encapsulation of anionic compounds using cationic lipids is essentially quantitative due to electrostatic interaction. In addition, it is believed that the cationic lipids interact with the negatively charged cell membranes initiating cellular membrane transport.

Experiments have shown that plasmid DNA can be encapsulated in small particles that consist of a single plasmid encapsulated within a bilayer lipid vesicle. These particles typically contain the fusogenic lipid dioleoylphosphatidylethanolamine (DOPE), low levels of a cationic lipid, and can be stabilized in aqueous media by the presence of a poly (ethylene glycol) (PEG) coating. These particles have systemic applications as they exhibit extended circulation lifetimes following intravenous (i.v.) injection, can accumulate preferentially in various tissues and organs or tumors due to the enhanced vascular permeability in such regions, and can be designed to escape the lyosomic pathway of endocytosis by disruption of endosomal membranes. These properties can be useful in delivering biologically active molecules to various cell types for experimental and therapeutic applications. For example, the effective use of nucleic acid technologies such as short interfering RNA (siRNA), antisense, ribozymes, decoys, triplex forming oligonucleotides, 2-5A oligonucleotides, and aptamers in vitro and in vivo may benefit from efficient delivery of these compounds across cellular membranes. Certain compositions consisting of the combination of siRNA, certain amphipathic compounds, and certain polycations have been disclosed. Certain lipid based formulations, certain lipid encapsulated interfering RNA formulations, and certain polycationic compositions for the cellular delivery of polynucleotides have been described. Short interfering nucleic acid molecules (siNA) and various technologies for the delivery of siNA molecules and other polynucleotides have also been described.

In addition, recent work involving cationic lipid particles demonstrated the formation of two structurally different complexes comprising nucleic acid (or other polyanionic compound) and cationic lipid. One structure comprises a multilamellar structure with nucleic acid monolayers sandwiched between cationic lipid bilayers ("lamellar structure"). A second structure comprises a two dimensional hexagonal columnar phase structure ("inverted hexagonal structure") in which nucleic acid molecules are encircled by cationic lipid in the formation of a hexagonal structure. Authors also demonstrated that the inverted hexagonal structure transfects mammalian cells more efficiently than the lamellar structure. Further, optical microscopy studies showed that the complexes comprising the lamellar structure bind stably to anionic vesicles without fusing to the vesicles, whereas the complexes comprising the inverted hexagonal structure are unstable and rapidly fuse to the anionic vesicles, releasing the nucleic acid upon fusion.

The structural transformation from lamellar phase to inverted hexagonal phase complexes is achieved either by incorporating a suitable helper lipid that assists in the adoption of an inverted hexagonal structure or by using a co-surfactant, such as hexanol. However, neither of these transformation conditions are suitable for delivery in biological systems. Furthermore, while the inverted hexagonal complex exhibits greater transfection efficiency, it has very poor serum stability compared to the lamellar complex. Thus, there remains a need to design delivery agents that are serum stable.

SUMMARY OF THE INVENTION

The invention provides compounds, compositions and methods for improving the efficiency of systemic and local delivery of biologically active molecules. Among other things, the invention provides compounds, compositions and methods for making and using delivery agents that are stable in circulation and undergo structural changes under appropriate physiological conditions (e.g., pH) which increase the efficiency of delivery of biologically active molecules.

In a broad aspect, the invention encompasses the compounds of formulae I-VI, shown below.

Thus, one aspect of the invention provides compounds of formula I

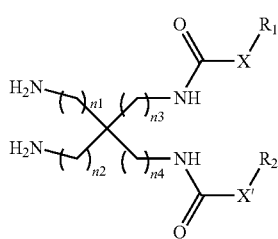

wherein
n1, n2, n3, and n4 are independently 1, 2, 3, or 4;
X and X' are independently a bond, oxygen, or nitrogen; and
$R_1$ and $R_2$ are independently $C_8$-$C_{25}$ hydrocarbon groups optionally containing from 1-4 double or triple bonds.

The second aspect of the invention provides compounds of formula II

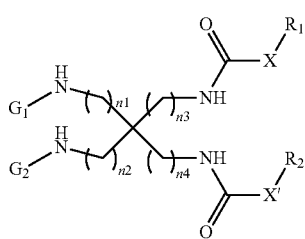

wherein
n1, n2, n3, and n4 are independently 1, 2, 3, or 4;
X and X' are independently a bond, oxygen, or nitrogen; and
$R_1$ and $R_2$ are independently $C_8$-$C_{25}$ hydrocarbon groups optionally containing from 1-4 double or triple bonds; and
$G_1$ and $G_2$ are independently hydrogen or a polymer moiety.

The third aspect of the invention provides compounds of formula III,

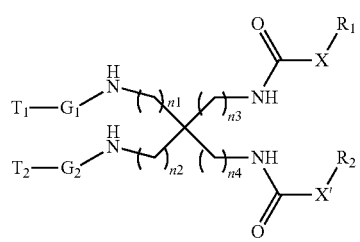

wherein
n1, n2, n3, and n4 are independently 1, 2, 3, or 4;
X and X' are independently a bond, oxygen, or nitrogen;
$R_1$ and $R_2$ are independently $C_8$-$C_{25}$ hydrocarbon groups optionally containing from 1-4 double or triple bonds; and $T_1$ and $T_2$ are independently hydrogen or a targeting ligand;
$G_1$ and $G_2$ are independently bond or a polymer moiety, where at least one of $T_1$ and $T_2$ is a targeting ligand.

The fourth aspect of the invention provides compounds of formula IV,

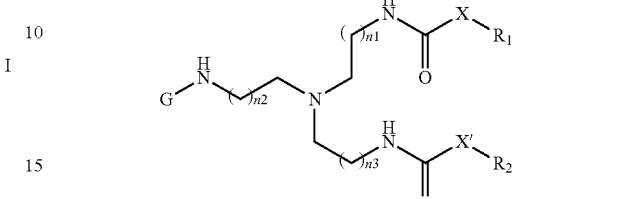

wherein
n1, n2, and n3 are independently 1, 2, 3, or 4;
X and X' are independently a bond, oxygen, or nitrogen;
$R_1$ and $R_2$ are independently $C_8$-$C_{25}$ hydrocarbon groups optionally containing from 1-4 double or triple bonds; and
G is hydrogen or a polymer moiety.

The fifth aspect of the invention provides compounds of formula V,

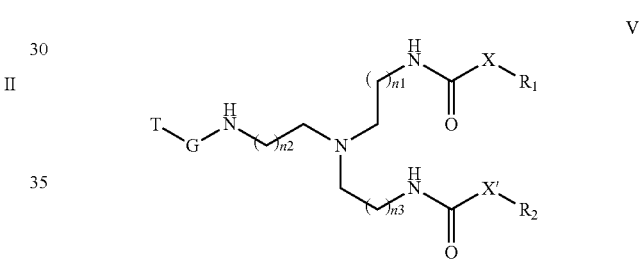

wherein
n1, n2, and n3 are independently 1, 2, 3, or 4;
X and X' are independently a bond, oxygen, or nitrogen;
$R_1$ and $R_2$ are independently $C_8$-$C_{25}$ hydrocarbon groups optionally containing from 1-4 double or triple bonds; and
T is a targeting ligand; and
G is a bond or a polymer moiety.

In another aspect, the invention provides compounds of formula VI,

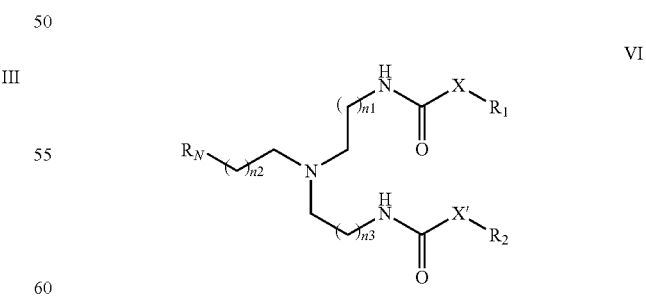

wherein
n1, n2, and n3 are independently 1, 2, 3, or 4;
X and X' are independently a bond, oxygen, or nitrogen;
$R_1$ and $R_2$ are independently $C_2$-$C_{25}$ hydrocarbon groups optionally containing from 1-4 double or triple bonds; and
$R_N$ represents $NHR_4$, $NR_4R_5$, or $N^+R_4R_5R_6$; where $R_4$, $R_5$, and $R_6$ independently represent $C_1$-$C_6$ alkyl groups.

The invention also provides synthetic intermediates that are useful in making the compounds of Formulae I-VI.

One aspect of the invention provides formulations comprising a compound of any formulae I-VI. The formulations of the invention contain lipoplexes or liposomes formed by the compounds of formulae I-VI.

One aspect of the invention provides formulations comprising a compound of any formulae I-VI and another molecule, which may be a biologically active molecule. The biologically active molecule may be (a) selected from the group consisting of: ribosomal RNA; antisense polynucleotides of RNA or DNA; ribozymes; siRNA; shRNA; miRNA; and polynucleotides of genomic DNA, cDNA, or mRNA that encode for a therapeutically useful protein; or (b) proteins, peptides, cholesterol, hormones, small molecules such as antivirals or chemotherapeutics, vitamins, and co-factors.

In a related aspect, the invention provides formulations comprising a compound of any formulae I-VI and an aptamer. In these formulations, the aptamer is not covalently bound to the compound. Thus, where the compound contains a targeting ligand, T, the resulting formulation may include a covalently bound targeting ligand and a aptamer that is not covalently bound. In these formulations, the aptamers and targeting ligands may be the same or different.

Another aspect of the invention provides formulations comprising particles formed by the compounds of any formula I-VI and another molecule, which may be a biologically active molecule. In this aspect, the invention provides stable particles useful for encapsulating, e.g., one or more siRNA molecules.

One aspect of the invention provides a method of introducing siRNA into a cell, comprising contacting the cell with a formulation of the invention.

One aspect of the invention provides a method of modulating expression of a target sequence, said method comprising administering to a mammalian subject a therapeutically effective amount of a formulation of the invention.

Another aspect of the invention provides a method for in vivo delivery of siRNA, said method comprising administering to a mammalian subject a therapeutically effective amount of a formulation of the invention.

Another aspect of the invention provides a method for in vivo delivery of plasmid DNA, said method comprising administering to a mammalian subject a therapeutically effective amount of a formulation of the invention.

In yet another aspect of the invention provides a method of treating or preventing a disease in a mammalian subject, said method comprising administering to said subject a therapeutically effective amount of a formulation of the invention.

It has been surprisingly discovered that formulations and delivery systems made using compounds of the invention, for example, dioleoyl monoamine, are both efficacious for transcript specific knockdown and are relatively non-toxic.

It has also been surprisingly discovered that the use of formulations and delivery systems of the invention results in preferential uptake of a drug by lung tissue and also leads to preferential transcript knockdown in lung relative to other tissues such as liver.

DETAILED DESCRIPTION OF THE INVENTION

Figure 1:
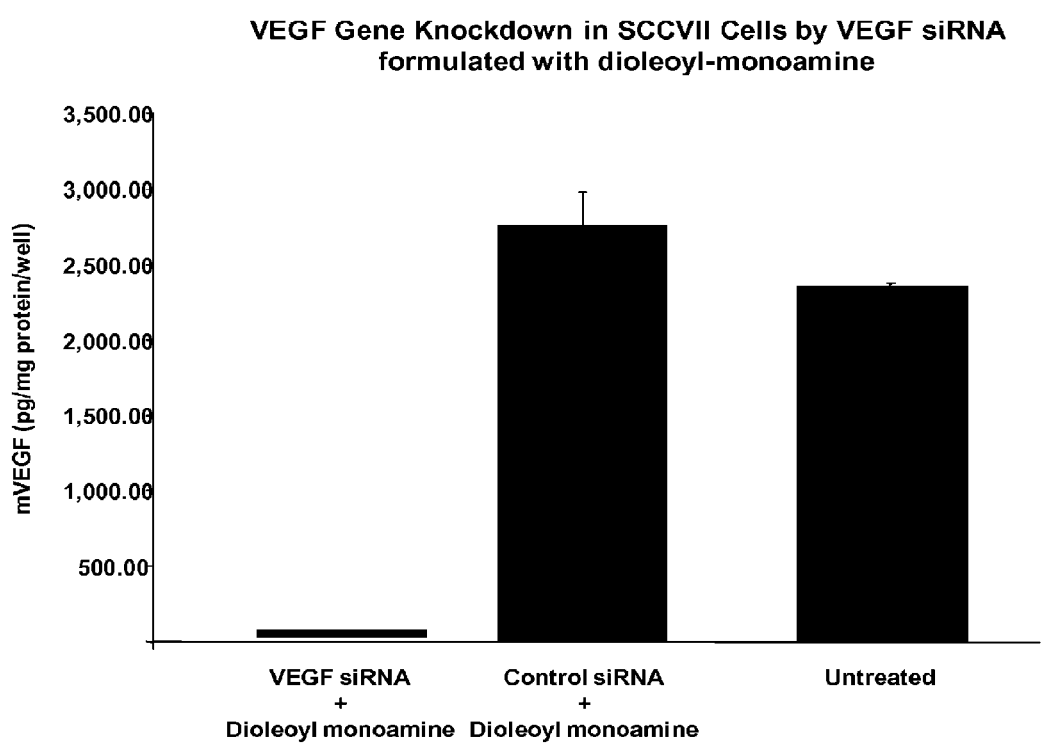
FIG. 1 is a graph showing protein expression levels of VEGF in cell culture medium following an in vitro transfection using murine squamous cell carcinoma VII (SCCVII) cells. Cells were transfected with siRNA formulated with dioleoyl monoamine.

One aspect of the invention provides compounds of formula I,

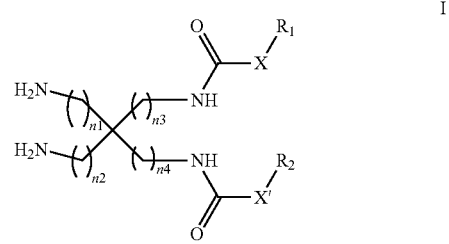

and the pharmaceutically acceptable salts thereof, wherein n1, n2, n3, and n4 are independently 1, 2, 3, or 4;

X and X' are independently a bond, oxygen, or nitrogen; and $R_1$ and $R_2$ are independently $C_8$-$C_{25}$ hydrocarbon groups optionally containing from 1-4 double or triple bonds.

In one embodiment, the invention provides compounds of formula I wherein n1, n2, n3, and n4 are all 1, and X and X' are bonds.

In one embodiment, the invention provides compounds of formula I wherein at least one of $R_1$ and $R_2$ is a $C_8$-$C_{25}$ hydrocarbon group containing from 1-4 double bonds.

In another embodiment, the invention provides compounds of formula I wherein both of $R_1$ and $R_2$ are $C_8$-$C_{25}$ hydrocarbon groups containing from 1-4 double bonds.

In yet another embodiment, the invention provides compounds of formula I wherein $R_1$ and $R_2$ are independently $C_8$-$C_{25}$ hydrocarbon groups containing 1 or 2 double bonds.

In one embodiment, the invention provides compounds of formula I wherein $R_1$ and $R_2$ are independently $C_8$-$C_{25}$ hydrocarbon groups containing 1 double bond.

In one embodiment, the invention provides compounds of formula I wherein $R_1$ and $R_2$ are independently $C_{14}$-$C_{20}$ hydrocarbon groups containing 1 or 2 double bonds.

In yet another embodiment, the invention provides compounds of formula I, wherein $R_1$ and $R_2$ are independently $C_{14}$-$C_{20}$ hydrocarbon groups containing 1 double bond.

In one embodiment, the invention provides compounds of formula I wherein both of —C(O)X—$R_1$ and —C(O)X'—$R_2$ represent oleoyl groups.

In another embodiment, the invention provides compounds of formula I wherein n1, n2, n3, and n4 are the same and are 1 or 2; X and X' are bonds; and at least one of $R_1$ and $R_2$ is a $C_8$-$C_{25}$ hydrocarbon group containing from 1-4 double bonds.

In still another embodiment, the invention provides compounds of formula I wherein n1, n2, n3, and n4 are the same and are 1 or 2; X and X' are bonds; and $R_1$ and $R_2$ are the same and represent $C_8$-$C_{25}$ hydrocarbon groups containing from 1-4 double bonds.

In yet another embodiment, the invention provides compounds of formula I wherein n1, n2, n3, and n4 are the same and are 1 or 2; X and X' are bonds; and $R_1$ and $R_2$ are the same and represent a $C_8$-$C_{25}$ hydrocarbon group containing from 1-2, preferably 1, double bonds.

In yet another embodiment, the invention provides compounds of formula I wherein n1, n2, n3, and n4 are 1; X and X' are bonds; and $R_1$ and $R_2$ are the same and represent a $C_{14}$-$C_{20}$ hydrocarbon group containing from 1-2, preferably 1, double bonds.

Another aspect of the invention provides compounds of formula II,

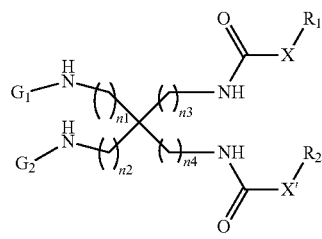

wherein
n1, n2, n3, and n4 are independently 1, 2, 3, or 4;
X and X' are independently a bond, oxygen, or nitrogen; and
$R_1$ and $R_2$ are independently $C_8$-$C_{25}$ hydrocarbon groups optionally containing from 1-4 double or triple bonds; and
$G_1$ and $G_2$ are independently hydrogen or a polymer moiety.

In one embodiment, the invention provides compounds of formula II wherein n1, n2, n3, and n4 are all 1, and X and X' are both bonds.

In one embodiment, the invention provides compounds of formula II wherein at least one of $R_1$ and $R_2$ is a $C_8$-$C_{25}$ hydrocarbon group containing from 1-4 double bonds.

In another embodiment, the invention provides compounds of formula II wherein both of $R_1$ and $R_2$ are $C_8$-$C_{25}$ hydrocarbon groups containing from 1-4 double bonds.

In yet another embodiment, the invention provides compounds of formula II wherein $R_1$ and $R_2$ are independently $C_8$-$C_{25}$ hydrocarbon groups containing 1 or 2 double bonds.

In yet another embodiment, the invention provides compounds of formula II wherein $R_1$ and $R_2$ are independently $C_8$-$C_{25}$ hydrocarbon groups containing 1 double bond.

In one embodiment, the invention provides compounds of formula II wherein $R_1$ and $R_2$ are independently $C_{14}$-$C_{20}$ hydrocarbon groups containing 1 or 2 double bonds.

In yet another embodiment, the invention provides compounds of formula II wherein $R_1$ and $R_2$ are independently $C_{14}$-$C_{20}$ hydrocarbon groups containing 1 double bond.

In one embodiment, the invention provides compounds of formula II wherein both of —C(O)X—$R_1$ and —C(O)X'—$R_2$ represent oleoyl groups.

In one embodiment, the invention provides compounds of formula II where one of $G_1$ and $G_2$ is a polymer moiety and the other is hydrogen.

In one embodiment, the invention provides compounds of formula II wherein one of $G_1$ and $G_2$ is a polyoxyalkylene, polyvinylpyrrolidone, polyacrylamide, polydimethylacrylamide, polyvinyl alcohol, dextran, poly(L-glutamic acid), styrene maleic anhydride, poly-N-(2-hydroxypropyl)methacrylamide, or polydivinylether maleic anhydride.

In another embodiment, the invention provides compounds of formula II wherein the polymer comprises at least one linker group between polymer units.

In yet another embodiment, the invention provides compounds of formula II where the polymer moiety is a polyoxyalkylene.

In yet another embodiment, the invention provides compounds of formula II where the molecular weight of the polymer is from about 200-10,000 Da. Preferred polymers have molecular weights ranging from about 1,000-5,000 Da.

In one embodiment, the invention provides compounds of formula II where the polymer moiety comprises at least one linker selected from —C(O)—, —O—, —O—C(O)O—, —C(O)CH$_2$CH$_2$C(O)—, —S—S—, —NR$^3$—, —NR$^3$C(O)O—, —OC(O)NR$^3$—, —NR$^3$C(O)—, —C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)—, -alkylene-C(O)NR$^3$—, —NR$^3$C(O)O-alkylene-, —NR$^3$C(O)NR$^3$-alkylene-, —OC(O)NR$^3$-alkylene, —NR$^3$-alkylene-, —O-alkylene-, —NR$^3$C(O)-alkylene-, —C(O)NR$^3$-alkylene-, -alkylene-NR$^3$C(O)O-alkylene-, -alkylene-NR$^3$C(O)NR$^3$-alkylene-, -alkylene-OC(O)NR$^3$-alkylene-, -alkylene-NR$^3$-alkylene-, -alkylene-O-alkylene-, -alkylene-NR$^3$C(O)-alkylene-, —C(O)NR$^3$-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —C(O)NR$^3$-alkyleneoxy-, and -alkyleneoxy-NR$^3$C(O)O-alkyleneoxy-, where $R^3$ is hydrogen, or optionally substituted alkyl, and

where

is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR$^3$—, —NR$^3$C(O)O—, —OC(O)

NR³—, —NR³C(O)—, —C(O)NR³—, —NR³C(O)NR³—, -alkylene-NR³C(O)O—, -alkylene-NR³C(O)NR³—, -alkylene-OC(O)NR³-alkylene-NR³—, -alkylene-O—, -alkylene-NR³C(O)—, alkylene-C(O)NR³—, —NR³C(O)O-alkylene-, —NR³C(O)NR³-alkylene-, —OC(O)NR³-alkylene-, —NR³-alkylene-, —O-alkylene-, —NR³C(O)-alkylene-, —NR³C(O)O-alkyleneoxy-, —NR³C(O)NR³-alkyleneoxy-, —OC(O)NR³-alkyleneoxy, —NR³-alkyleneoxy-, —O-alkyleneoxy-, —NR³C(O)-alkyleneoxy-, —C(O)NR³-alkyleneoxy-, -alkyleneoxy-NR³C(O)O-alkyleneoxy-, —C(O)NR³-alkylene-, -alkylene-NR³C(O)O-alkylene-, -alkylene-NR³C(O)NR³-alkylene-, -alkylene-OC(O)NR³-alkylene-, -alkylene-NR³-alkylene-, alkylene-O-alkylene-, -alkylene-NR³C(O)-alkylene-, and —C(O)NR³-alkylene-, where R³ is as defined above.

In one embodiment, the invention provides compounds of formula II wherein the polymer is a polyoxyethylene where the oxyalkylene groups are independently straight or branched chain polyoxyalkylene groups having from 2-5 carbon atoms in their repeating units.

In one embodiment, the invention provides compounds of formula II wherein the polyoxyalkylene is a polyoxyethylene, a straight or branched chain polyoxypropylene, or a straight or branched chain polyoxybutylene.

In one embodiment, the invention provides compounds of formula II wherein the polyoxyalkylene is a polyoxyethylene.

In another embodiment, the invention provides compounds of formula II where n1, n2, n3, and n4 are all the same and are 1 or 2; X and X' are both bonds; and at least one of $R_1$ and $R_2$ is a $C_8$-$C_{25}$ hydrocarbon group containing from 1-4 double bonds.

In another embodiment, the invention provides compounds of formula II where n1, n2, n3, and n4 are all the same and are 1 or 2; X and X' are both bonds; and $R_1$ and $R_2$ are identical and represent $C_8$-$C_{25}$ hydrocarbon groups containing from 1-4 double bonds.

In another embodiment, the invention provides compounds of formula II where n1, n2, n3, and n4 are all the same and are 1; X and X' are both bonds; and $R_1$ and $R_2$ are identical and represent $C_8$-$C_{25}$ hydrocarbon groups containing from 1-4 double bonds.

In still another embodiment, the invention provides compounds of formula II where n1, n2, n3, and n4 are all the same and are 1; X and X' are both bonds; and $R_1$ and $R_2$ are identical and represent $C_{14}$-$C_{20}$ hydrocarbon groups containing from 1-4 double bonds.

In yet another embodiment, the invention provides compounds of formula II where n1, n2, n3, and n4 are all the same and are 1; X and X' are both bonds; and $R_1$ and $R_2$ are identical and represent $C_{14}$-$C_{20}$ hydrocarbon groups containing 1 or 2 double bonds.

Another aspect of the invention provides compounds of formula III,

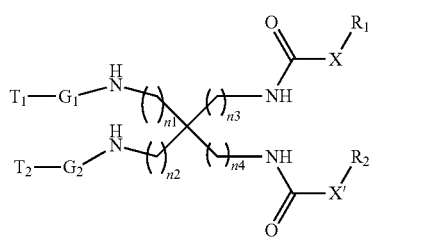

wherein
n1, n2, n3, and n4 are independently 1, 2, 3, or 4;
X and X' are independently a bond, oxygen, or nitrogen;
$R_1$ and $R_2$ are independently $C_8$-$C_{25}$ hydrocarbon groups optionally containing from 1-4 double or triple bonds; and
$T_1$ and $T_2$ are independently hydrogen or a targeting ligand;

$G_1$ and $G_2$ are independently bond or a polymer moiety, where at least one of $T_1$ and $T_2$ is a targeting ligand.

In one embodiment, the invention provides compounds of formula III wherein n1, n2, n3, and n4 are all 1, and both X and X' are bonds.

In one embodiment, the invention provides compounds of formula III wherein at least one of $R_1$ and $R_2$ is a $C_8$-$C_{25}$ hydrocarbon group containing from 1-4 double bonds.

In one embodiment, the invention provides compounds of formula III wherein both of $R_1$ and $R_2$ are $C_8$-$C_{25}$ hydrocarbon groups containing from 1-4 double bonds.

In another embodiment, the invention provides compounds of formula III wherein $R_1$ and $R_2$ are independently $C_8$-$C_{25}$ hydrocarbon groups containing 1 or 2 double bonds.

In yet another embodiment, the invention provides compounds of formula III wherein $R_1$ and $R_2$ are independently $C_8$-$C_{25}$ hydrocarbon groups containing 1 double bond.

In yet another embodiment, the invention provides compounds of formula III wherein $R_1$ and $R_2$ are independently $C_{14}$-$C_{20}$ hydrocarbon groups containing 1 or 2 double bonds.

In one embodiment, the invention provides compounds of formula III wherein $R_1$ and $R_2$ are independently $C_{14}$-$C_{20}$ hydrocarbon groups containing 1 double bond.

In one embodiment, the invention provides compounds of formula III wherein both of —C(O)X—$R_1$ and —C(O)X'—$R_2$ represent oleoyl groups.

In one embodiment, the invention provides compounds of formula III where one of $G_1$ and $G_2$ is a polymer moiety and the other is hydrogen.

In yet another embodiment, the invention provides compounds of formula III wherein the one of $G_1$ and $G_2$ is a polyoxyalkylene, polyvinylpyrrolidone, polyacrylamide, polydimethylacrylamide, polyvinyl alcohol, dextran, poly(L-glutamic acid), styrene maleic anhydride, poly-N-(2-hydroxypropyl)methacrylamide, or polydivinylether maleic anhydride.

In another embodiment, the invention provides compounds of formula III wherein the polymer comprises at least one linker group between polymer units.

In yet another embodiment, the invention provides compounds of formula III where the polymer moiety is a polyoxyalkylene.

In one embodiment, the invention provides compounds of formula III where the molecular weight of the polymer is from about 200-10,000 Da. Preferred polymers have molecular weights ranging from about 1,000-5,000 Da.

In one embodiment, the invention provides compounds of formula III where the polymer moiety comprises at least one linker selected from —C(O)—, —O—, —O—C(O)O—, —C(O)CH₂CH₂C(O)—, —S—S—, —NR³C(O)O—, —OC(O)NR³—, —NR³C(O)—, —C(O)NR³—, —NR³C(O)NR³—, -alkylene-NR³C(O)O—, -alkylene-NR³C(O)NR³—, -alkylene-OC(O)NR³—, -alkylene-NR³—, -alkylene-O—, -alkylene-NR³C(O)—, -alkylene-C(O)NR³—, —NR³C(O)O-alkylene-, —NR³C(O)NR³-alkylene-, —OC(O)NR³-alkylene, —NR³-alkylene-, —O-alkylene-, —NR³C(O)-alkylene-, —C(O)NR³-alkylene-, -alkylene-NR³C(O)O-alkylene-, -alkylene-NR³C(O)NR³-alkylene-, -alkylene-OC(O)NR³-alkylene-, -alkylene-NR³-alkylene-, -alkylene-O-alkylene-, -alkylene-NR³C(O)-alkylene-, —C(O)NR-alkylene-, —NR³C(O)O-alkyleneoxy-, —NR³C(O)NR³-alkyleneoxy-, —OC(O)NR³-alkyleneoxy, —NR³-alkyleneoxy-, —O-alkyleneoxy-, —NR³C(O)-alkyleneoxy-, —C(O)NR³-alkyleneoxy-, and -alkyleneoxy-NR³C(O)O-alkyleneoxy-, where R³ is as defined above and

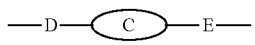

where

is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR³—, —NR³C(O)O—, —OC(O) NR³—, —NR³C(O)—, —C(O)NR³—, —NR³C(O)NR³—, -alkylene-NR³C(O)O—, -alkylene-NR³C(O)NR³—, -alkylene-OC(O)NR³—, -alkylene-NR³—, -alkylene-O—, -alkylene-NR³C(O)—, alkylene-C(O)NR³—, —NR³C(O)O-alkylene-, —NR³C(O)NR³-alkylene-, —OC(O)NR³-alkylene-, —NR³-alkylene-, —O-alkylene-, —NR³C(O)-alkylene-, —NR³C(O)O-alkyleneoxy-, —NR³C(O)NR³-alkyleneoxy-, —OC(O)NR³-alkyleneoxy, —NR³-alkyleneoxy-, —O-alkyleneoxy-, —NR³C(O)-alkyleneoxy-, —C(O)NR³-alkyleneoxy-, -alkyleneoxy-NR³C(O)O-alkyleneoxy-, —C(O)NR³-alkylene-, -alkylene-NR³C(O)O-alkylene-, -alkylene-NR³C(O)NR³-alkylene-, -alkylene-OC(O)NR³-alkylene-, -alkylene-NR³-alkylene-, alkylene-O-alkylene-, -alkylene-NR³C(O)-alkylene-, and —C(O)NR³-alkylene-, where R³ is as defined above.

In one embodiment, the invention provides compounds of formula III wherein the polymer is a polyoxyethylene where the oxyalkylene groups are independently straight or branched chain polyoxyalkylene groups having from 2-5 carbon atoms in their repeating units.

In another embodiment, the invention provides compounds of formula III wherein the polyoxyalkylene is a polyoxyethylene, a straight or branched chain polyoxypropylene, or a straight or branched chain polyoxybutylene.

In one embodiment, the invention provides compounds of formula III wherein the polyoxyalkylene is a polyoxyethylene and the targeting ligand is a pharmacologically active small molecule, an endosomolytic agent, a fusogenic peptide, a cell membrane permeating agent, a charge masking agent, a nucleic acid, or a cell receptor ligand.

In one embodiment, the invention provides compounds of formula III wherein the targeting ligand is a pharmacologically active small molecule that has anti-proliferative activity.

In one embodiment, the invention provides compounds of formula III wherein the polyoxyalkylene is a polyoxyethylene and the targeting ligand is a pharmacologically active small molecule that has anti-proliferative activity.

In one embodiment, the invention provides compounds of formula III wherein the targeting ligand is a folic acid group.

In one embodiment, the invention provides compounds of formula III wherein the polyoxyalkylene is a polyoxyethylene and the targeting ligand is a folic acid group.

In one embodiment, the invention provides compounds of formula III wherein the targeting ligand is a fusogenic peptide.

In one embodiment, the invention provides compounds of formula III wherein the polyoxyalkylene is a polyoxyethylene and the targeting ligand is a fusogenic peptide.

In one embodiment, the invention provides compounds of formula III wherein the targeting ligand is selected from the group consisting of biotin, galactose, acetylsalicylic acid, naproxen, and a cell receptor ligand.

In one embodiment, the invention provides compounds of formula III wherein the polyoxyalkylene is a polyoxyethylene and the targeting ligand is selected from the group consisting of biotin, galactose, acetylsalicylic acid, naproxen, and a cell receptor ligand.

In another embodiment, the invention provides compounds of formula III where n1, n2, n3, and n4 are the same and are 1 or 2; both X and X' are bonds; and at least one of $R_1$ and $R_2$ is a $C_8$-$C_{25}$ hydrocarbon group containing from 1-4 double bonds.

In another embodiment, the invention provides compounds of formula III where n1, n2, n3, and n4 are the same and are 1 or 2; both X and X' are bonds; and $R_1$ and $R_2$ are the same and represent a $C_8$-$C_{25}$ hydrocarbon group containing from 1-4 double bonds.

In another embodiment, the invention provides compounds of formula III where n1, n2, n3, and n4 are 1; both X and X' are bonds; and $R_1$ and $R_2$ are the same and represent a $C_8$-$C_{25}$ hydrocarbon group containing from 1-4 double bonds.

In another embodiment, the invention provides compounds of formula III where n1, n2, n3, and n4 are 1; both X and X' are bonds; and $R_1$ and $R_2$ are the same and represent a $C_8$-$C_{25}$ hydrocarbon group containing from 1-2 double bonds.

In another embodiment, the invention provides compounds of formula III where n1, n2, n3, and n4 are 1; both X and X' are bonds; and $R_1$ and $R_2$ are the same and represent a $C_{14}$-$C_{20}$ hydrocarbon group containing 1 double bond.

One aspect of the invention provides compounds of formula IV,

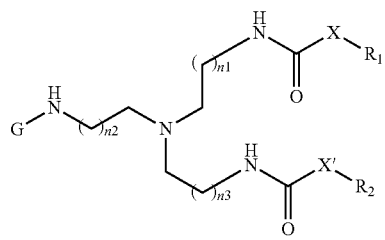

IV and the pharmaceutically acceptable salts thereof, wherein n1, n2, and n3 are independently 1, 2, 3, or 4;
X and X' are independently a bond, oxygen, or nitrogen;
$R_1$ and $R_2$ are independently $C_8$-$C_{25}$ hydrocarbon groups optionally containing from 1-4 double or triple bonds; and
G is hydrogen or a polymer moiety.

In one embodiment, the invention provides compounds of formula IV wherein n1, n2, and n3 are all 1, and X and X' are bonds.

In one embodiment, the invention provides compounds of formula IV wherein at least one of $R_1$ and $R_2$ is a $C_8$-$C_{25}$ hydrocarbon group containing from 1-4 double bonds.

In another embodiment, the invention provides compounds of formula IV wherein both of $R_1$ and $R_2$ are $C_8$-$C_{25}$ hydrocarbon groups containing from 1-4 double bonds.

In yet another embodiment, the invention provides compounds of formula IV wherein $R_1$ and $R_2$ are independently $C_8$-$C_{25}$ hydrocarbon groups containing 1 or 2 double bonds.

In another embodiment, the invention provides compounds of formula IV wherein $R_1$ and $R_2$ are independently $C_8$-$C_{25}$ hydrocarbon groups containing 1 double bond.

In one embodiment, the invention provides compounds of formula IV wherein $R_1$ and $R_2$ are independently $C_{14}$-$C_{20}$ hydrocarbon groups containing 1 or 2 double bonds.

In another embodiment, the invention provides compounds of formula IV wherein $R_1$ and $R_2$ are independently $C_{14}$-$C_{20}$ hydrocarbon groups containing 1 double bond.

In one embodiment, the invention provides compounds of formula IV wherein both of —C(O)X—$R_1$ and —C(O)X'—$R_2$ represent oleoyl groups.

In one embodiment, the invention provides compounds of formula IV where X is oxygen.

In one embodiment, the invention provides compounds of formula IV where X is nitrogen.

In one embodiment, the invention provides compounds of formula IV wherein G is a polyoxyalkylene, polyvinylpyrrolidone, polyacrylamide, polydimethylacrylamide, polyvinyl alcohol, dextran, poly(L-glutamic acid), styrene maleic anhydride, poly-N-(2-hydroxypropyl)methacrylamide, or polydivinylether maleic anhydride.

In another embodiment, the invention provides compounds of formula IV wherein the polymer comprises at least one linker group between polymer units.

In yet another embodiment, the invention provides compounds of formula IV where the polymer moiety is a polyoxyalkylene.

In yet another embodiment, the invention provides compounds of formula IV where the molecular weight of the polymer is from about 200-10,000 Da. Preferred polymers have molecular weights ranging from about 1,000-5,000 Da.

In one embodiment, the invention provides compounds of formula IV where the polymer moiety comprises at least one linker selected from —C(O)—, —O—, —O—C(O)O—, —C(O)CH$_2$CH$_2$C(O)—, —S—S—, —NR$^3$—, —NR$^3$C(O)O—, —O—C(O)NR$^3$—, —NR$^3$C(O)—C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)—, -alkylene-C(O)NR$^3$—, —NR$^3$C(O)O-alkylene-, —NR$^3$C(O)NR$^3$-alkylene-, —OC(O)NR$^3$-alkylene, —NR$^3$-alkylene-, —O-alkylene-, —NR$^3$C(O)-alkylene-, —C(O)NR$^3$-alkylene-, -alkylene-NR$^3$C(O)O-alkylene-, -alkylene-NR$^3$C(O)NR$^3$-alkylene-, -alkylene-OC(O)NR$^3$-alkylene-, -alkylene-NR$^3$-alkylene-, -alkylene-O-alkylene-, -alkylene-NR$^3$C(O)-alkylene-, —C(O)NR$^3$-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —C(O)NR$^3$-alkyleneoxy-, and -alkyleneoxy-NR$^3$C(O)O-alkyleneoxy-, where $R^3$ is as defined above and

where

is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR$^3$—, —NR$^3$C(O)O—, —OC(O)NR$^3$—, —NR$^3$C(O)—C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)—, alkylene-C(O)NR$^3$—, —NR$^3$C(O)O-alkylene-, —NR$^3$C(O)NR$^3$-alkylene-, —OC(O)NR$^3$-alkylene-, —NR$^3$-alkylene-, —O-alkylene-, —NR$^3$C(O)-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —C(O)NR$^3$-alkyleneoxy-, -alkyleneoxy-NR$^3$C(O)O-alkyleneoxy-, -alkylene-NR$^3$C(O)NR$^3$-alkylene-, -alkylene-OC(O)NR$^3$-alkylene-, -alkylene-NR$^3$-alkylene-, alkylene-O-alkylene-, -alkylene-NR$^3$C(O)-alkylene-, and —C(O)NR$^3$-alkylene-, where $R^3$ is as defined above.

In one embodiment, the invention provides compounds of formula IV wherein the polymer is a polyoxyethylene where the oxyalkylene groups are independently straight or branched chain polyoxyalkylene groups having from 2-5 carbon atoms in their repeating units.

In another embodiment, the invention provides compounds of formula IV wherein the polyoxyalkylene is a polyoxyethylene, a straight or branched chain polyoxypropylene, or a straight or branched chain polyoxybutylene.

In yet another embodiment, the invention provides compounds of formula IV wherein the polyoxyalkylene is a polyoxyethylene.

In another embodiment, the invention provides compounds of formula IV wherein n1, n2, and n3 are the same and are 1 or 2; X and X' are bonds; and at least one of $R_1$ and $R_2$ is a $C_8$-$C_{25}$ hydrocarbon group containing from 1-4 double bonds.

In another embodiment, the invention provides compounds of formula IV wherein n1, n2, and n3 are the same and are 1 or 2; X and X' are bonds; and both of $R_1$ and $R_2$ are $C_8$-$C_{25}$ hydrocarbon groups containing from 1-4 double bonds.

In another embodiment, the invention provides compounds of formula IV wherein n1, n2, and n3 are the same and are 1 or 2; X and X' are bonds; and $R_1$ and $R_2$ are the same and represent $C_8$-$C_{25}$ hydrocarbon groups containing from 1-4 double bonds.

In yet another embodiment, the invention provides compounds of formula IV wherein n1, n2, and n3 are the same and are 1 or 2; X and X' are bonds; and $R_1$ and $R_2$ are the same and represent $C_8$-$C_{25}$ hydrocarbon groups containing from 1-2 double bonds.

In yet another embodiment, the invention provides compounds of formula IV wherein n1, n2, and n3 are 1; X and X' are bonds; and $R_1$ and $R_2$ are the same and represent $C_{14}$-$C_{20}$ hydrocarbon groups containing 1 double bond.

Another aspect of the invention provides compounds of formula V,

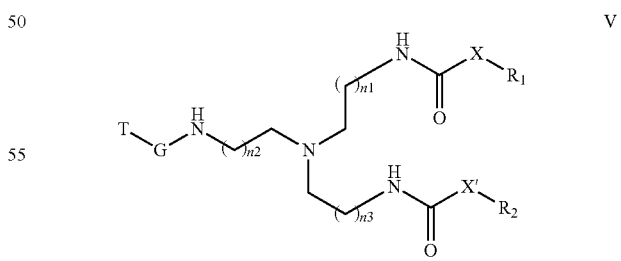

wherein
n1, n2, and n3 are independently 1, 2, 3, or 4;
X and X' are independently a bond, oxygen, or nitrogen;
$R_1$ and $R_2$ are independently $C_8$-$C_{25}$ hydrocarbon groups
  optionally containing from 1-4 double or triple bonds; and
T is a targeting ligand; and
G is a bond, or a polymer moiety.

In one embodiment, the invention provides compounds of formula V wherein n1, n2, and n3 are all 1, and both X and X' are bonds.

In one embodiment, the invention provides compounds of formula V wherein at least one of $R_1$ and $R_2$ is a $C_8$-$C_{25}$ hydrocarbon group containing from 1-4 double bonds.

In another embodiment, the invention provides compounds of formula V wherein both of $R_1$ and $R_2$ are $C_8$-$C_{25}$ hydrocarbon groups containing from 1-4 double bonds.

In yet another embodiment, the invention provides compounds of formula V wherein $R_1$ and $R_2$ are independently $C_8$-$C_{25}$ hydrocarbon groups containing 1 or 2 double bonds.

In yet another embodiment, the invention provides compounds of formula V wherein $R_1$ and $R_2$ are independently $C_8$-$C_{25}$ hydrocarbon groups containing 1 double bond.

In one embodiment, the invention provides compounds of formula V wherein $R_1$ and $R_2$ are independently $C_{14}$-$C_{20}$ hydrocarbon groups containing 1 or 2 double bonds.

In yet another embodiment, the invention provides compounds of formula V wherein $R_1$ and $R_2$ are independently $C_{14}$-$C_{20}$ hydrocarbon groups containing 1 double bond.

In one embodiment, the invention provides compounds of formula V wherein both of —C(O)X—$R_1$ and —C(O)X'—$R_2$ represent oleoyl groups.

In another embodiment, the invention provides compounds of formula V wherein G is a polymer moiety.

In yet another embodiment, the invention provides compounds of formula V wherein G is a polyoxyalkylene, polyvinylpyrrolidone, polyacrylamide, polydimethylacrylamide, polyvinyl alcohol, dextran, poly(L-glutamic acid, styrene maleic anhydride, poly-N-(2-hydroxypropyl)methacrylamide, or polydivinylether maleic anhydride.

In yet another embodiment, the invention provides compounds of formula V wherein the polymer comprises at least one linker group between polymer units.

In one embodiment, the invention provides compounds of formula V where the polymer moiety is a polyoxyalkylene.

In another embodiment, the invention provides compounds of formula V where the molecular weight of the polymer is from about 200-10,000 Da. The preferred molecular weight of the polymer is from about 1,000-5,000 Da.

In one embodiment, the invention provides compounds of formula V where the polymer moiety comprises at least one linker selected from —C(O)—, —O—, —O—C(O)O—, —C(O)CH$_2$CH$_2$C(O)—, —S—S—, —NR$^3$—, —NR$^3$C(O)O—, —OC(O)NR$^3$—, —NR$^3$C(O)—, —C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)—, -alkylene-C(O)NR$^3$—, —NR$^3$C(O)O-alkylene-, —NR$^3$C(O)NR$^3$-alkylene-, —OC(O)NR$^3$-alkylene, —NR$^3$-alkylene-, —O-alkylene-, —NR$^3$C(O)-alkylene-, —C(O)NR$^3$-alkylene-, -alkylene-NR$^3$C(O)O-alkylene-, -alkylene-NR$^3$C(O)NR$^3$-alkylene-, -alkylene-OC(O)NR$^3$-alkylene-, -alkylene-NR$^3$-alkylene-, -alkylene-O-alkylene-, -alkylene-NR$^3$C(O)-alkylene-, —C(O)NR$^3$-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —C(O)NR$^3$-alkyleneoxy-, and -alkyleneoxy-NR$^3$C(O)O-alkyleneoxy-, where R$^3$ is as defined above and

—D—◯C◯—E— where

◯C◯ is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR$^3$—, —NR$^3$C(O)O—, —OC(O)NR$^3$—, —NR$^3$C(O)—, —C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)—, alkylene-C(O)NR$^3$—, —NR$^3$C(O)O-alkylene-, —NR$^3$C(O)NR$^3$-alkylene-, —OC(O)NR$^3$-alkylene-, —NR$^3$-alkylene-, —O-alkylene-, —NR$^3$C(O)-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —O(O)NR$^3$-alkyleneoxy-, -alkyleneoxy-NR$^3$C(O)O-alkyleneoxy-, —C(O)NR$^3$-alkylene-, -alkylene-NR$^3$C(O)O-alkylene-, -alkylene-NR$^3$C(O)NR$^3$-alkylene-, -alkylene-OC(O)NR$^3$-alkylene-, -alkylene-NR$^3$-alkylene-, alkylene-O-alkylene-, -alkylene-NR$^3$C(O)-alkylene-, and —C(O)NR$^3$-alkylene-, where R$^3$ is as defined above.

In another embodiment, the invention provides compounds of formula V wherein the polymer is a polyoxyethylene where the oxyalkylene groups are independently straight or branched chain polyoxyalkylene groups having from 2-5 carbon atoms in their repeating units.

In yet another embodiment, the invention provides compounds of formula V wherein the polyoxyalkylene is a polyoxyethylene, a straight or branched chain polyoxypropylene, or a straight or branched chain polyoxybutylene.

In one embodiment, the invention provides compounds of formula V wherein the polyoxyalkylene is a polyoxyethylene and the targeting ligand is a pharmacologically active small molecule, an endosomolytic agent, a fusogenic peptide, a cell membrane permeating agent, a charge masking agent, or a nucleic acid.

In one embodiment, the invention provides compounds of formula V wherein the targeting ligand is a pharmacologically active small molecule that has anti-proliferative activity.

In one embodiment, the invention provides compounds of formula V wherein the polyoxyalkylene is a polyoxyethylene and the targeting ligand is a pharmacologically active small molecule that has anti-proliferative activity.

In yet another embodiment, the invention provides compounds of formula V wherein the targeting ligand is a folic acid group.

In yet another embodiment, the invention provides compounds of formula V wherein the polyoxyalkylene is a polyoxyethylene and the targeting ligand is a folic acid group.

In one embodiment, the invention provides compounds of formula V wherein the targeting ligand is a fusogenic peptide.

In one embodiment, the invention provides compounds of formula V wherein the polyoxyalkylene is a polyoxyethylene and the targeting ligand is a fusogenic peptide.

In one embodiment, the invention provides compounds of formula V wherein the targeting ligand is selected from the group consisting of biotin, galactose, acetylsalicylic acid, and naproxen.

In one embodiment, the invention provides compounds of formula V wherein the polyoxyalkylene is a polyoxyethylene and the targeting ligand is selected from the group consisting of biotin, galactose, acetylsalicylic acid, and naproxen.

In another embodiment, the invention provides compounds of formula V wherein n1, n2, and n3 are the same and are 1 or 2; X and X' are bonds; and at least one of $R_1$ and $R_2$ is a $C_8$-$C_{25}$ hydrocarbon group containing from 1-4 double bonds.

In another embodiment, the invention provides compounds of formula V wherein n1, n2, n3, and n4 are the same and are 1 or 2; X and X' are bonds; and both of $R_1$ and $R_2$ are $C_8$-$C_{25}$ hydrocarbon groups containing from 1-4 double bonds.

In another embodiment, the invention provides compounds of formula V wherein n1, n2, and n3 are the same and are 1 or 2; X and X' are bonds; and $R_1$ and $R_2$ are the same and represent $C_8$-$C_{25}$ hydrocarbon groups containing from 1-4 double bonds.

In yet another embodiment, the invention provides compounds of formula V wherein n1, n2, and n3 are the same and are 1 or 2; X and X' are bonds; and $R_1$ and $R_2$ are the same and represent $C_{14}$-$C_{20}$ hydrocarbon groups containing from 1-2 double bonds.

In yet another embodiment, the invention provides compounds of formula V wherein n1, n2, and n3 are 1; X and X' are bonds; and $R_1$ and $R_2$ are the same and represent $C_8$-$C_{25}$ hydrocarbon groups containing 1 double bond.

Another aspect of the invention provides compounds of formula VI

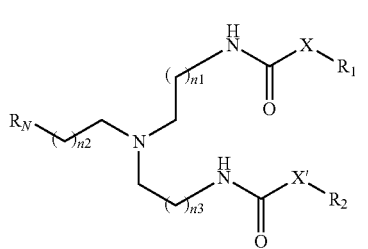

VI wherein
n1, n2, and n3 are independently 1, 2, 3, or 4;
X and X' are independently a bond, oxygen, or nitrogen;
$R_1$ and $R_2$ are independently $C_8$-$C_{25}$ hydrocarbon groups optionally containing from 1-4 double or triple bonds; and
$R_N$ represents $NHR_4$, $NR_4R_5$, or $N^1R_4R_5R_6$; where
$R_4$, $R_5$, and $R_6$ independently represent $C_1$-$C_6$ alkyl groups.

In one embodiment, the invention provides compounds of formula VI wherein n1, n2, and n3 are all 1, and both X and X' are bonds.

In one embodiment, the invention provides compounds of formula VI wherein at least one of $R_1$ and $R_2$ is a $C_8$-$C_{25}$ hydrocarbon group containing from 1-4 double bonds.

In another embodiment, the invention provides compounds of formula VI wherein both of $R_1$ and $R_2$ are $C_8$-$C_{25}$ hydrocarbon groups containing from 1-4 double bonds.

In yet another embodiment, the invention provides compounds of formula VI wherein $R_1$ and $R_2$ are independently $C_8$-$C_{25}$ hydrocarbon groups containing 1 or 2 double bonds.

In yet another embodiment, the invention provides compounds of formula VI wherein $R_1$ and $R_2$ are independently $C_8$-$C_{25}$ hydrocarbon groups containing 1 double bond.

In one embodiment, the invention provides compounds of formula VI wherein $R_1$ and $R_2$ are independently $C_{14}$-$C_{20}$ hydrocarbon groups containing 1 or 2 double bonds.

In yet another embodiment, the invention provides compounds of formula VI wherein $R_1$ and $R_2$ are independently $C_{14}$-$C_{20}$ hydrocarbon groups containing 1 double bond.

In one embodiment, the invention provides compounds of formula VI wherein both of —C(O)X—$R_1$ and —C(O)X'—$R_2$ represent oleoyl groups.

In another embodiment, the invention provides compounds of formula VI wherein $R_N$ represents $NHR_4$ where $R_4$ represents a $C_1$-$C_2$ alkyl group.

In another embodiment, the invention provides compounds of formula VI wherein $R_N$ represents $NR_4R_5$ where $R_4$ and $R_5$ independently represent $C_1$-$C_2$ alkyl groups.

In another embodiment, the invention provides compounds of formula VI wherein $R_N$ represents $N^+R_4R_5R_6$ where $R_4$, $R_5$, and $R_6$ independently represents $C_1$-$C_2$ alkyl groups.

In another embodiment, the invention provides compounds of formula VI wherein n1, n2, and n3 are the same and are 1 or 2; X and X' are bonds; and at least one of $R_1$ and $R_2$ is a $C_8$-$C_{25}$ hydrocarbon group containing from 1-4 double bonds.

In another embodiment, the invention provides compounds of formula VI wherein n1, n2, n3, and n4 are the same and are or 2; X and X' are bonds; and both of $R_1$ and $R_2$ are $C_8$-$C_{25}$ hydrocarbon groups containing from 1-4 double bonds.

In another embodiment, the invention provides compounds of formula VI wherein n1, n2, and n3 are the same and are 1 or 2; X and X' are bonds; and $R_1$ and $R_2$ are the same and represent $C_8$-$C_{25}$ hydrocarbon groups containing from 1-4 double bonds.

In yet another embodiment, the invention provides compounds of formula VI wherein n1, n2, and n3 are the same and are 1 or 2; X and X' are bonds; and $R_1$ and $R_2$ are the same and represent $C_{14}$-$C_{20}$ hydrocarbon groups containing from 1-2 double bonds.

In yet another embodiment, the invention provides compounds of formula VI wherein n1, n2, and n3 are 1; X and X' are bonds; and $R_1$ and $R_2$ are the same and represent $C_8$-$C_{25}$ hydrocarbon groups containing 1 double bond.

In yet another embodiment, the invention provides compounds of formula VI wherein n1, n2, and n3 are 1; X and X' are bonds; $R_1$ and $R_2$ are the same and represent $C_8$-$C_{25}$ hydrocarbon groups containing 1 double bond; and $R_N$ is represents $N^+R_4R_5R_6$ where $R_4$, $R_5$, and $R_6$ independently represents $C_1$-$C_6$ alkyl groups.

In yet another embodiment, the invention provides compounds of formula VI wherein n1, n2, and n3 are 1; X and X' are bonds; $R_1$ and $R_2$ are the same and represent $C_8$-$C_{25}$ hydrocarbon groups containing 1 double bond; and $R_N$ is represents $N^+R_4R_5R_6$ where $R_4$, $R_5$, and $R_6$ independently represents $C_1$-$C_2$ alkyl groups.

In another embodiment of compounds of formulae I-VI where X and X' both represent a bond, suitable $C(O)XR_1$ and $C(O)X'R_2$ moieties include groups derived from saturated, monounsaturated, and polyunsaturated fatty acids having from 10-22 carbon atoms, preferably from 12-20 carbon atoms, and more preferably from 14-18 carbon atoms. Representative $C(O)XR_1$ and $C(O)X'R_2$ moieties include those derived from, for example, myristoleic acid, palmitoleic acid, oleic acid, linoleic acid, linolenic acid, arachidonic acid, eicosapentaenoic acid, erucic acid, docosahexaenoic acid, isostearic acid, elaidic acid, petroselinic acid, eleostearic acid, or lauroleic acid.

In another embodiment of compounds of formulae I-VI where X and X' independently both represent a nitrogen or oxygen, suitable $R_1$ and $R_2$ moieties include groups derived from saturated and polyunsaturated fatty acids having from 10-22 carbon atoms, preferably from 12-20 carbon atoms, and more preferably from 14-18 carbon atoms. Representative $R_1$ and $R_2$ moieties include those derived from, for example, such as those derived from myristoleic acid, palmitoleic acid, oleic acid, linoleic acid, linolenic acid, arachidonic acid, eicosapentaenoic acid, erucic acid, docosahexaenoic acid, isostearic acid, elaidic acid, petroselinic acid, eleostearic acid, or lauroleic acid.

One aspect of the invention provides formulations comprising a compound of any of formulae I-VI.

One aspect of the invention provides formulations comprising a compound of any of formulae I-VI and another molecule, which may be a biologically active molecule, where the molecule is selected from the group consisting of: ribosomal RNA; antisense polynucleotides of RNA or DNA; ribozymes; siRNA; shRNA; miRNA; and polynucleotides of genomic DNA, cDNA, or mRNA that encode for a therapeutically useful protein.

Another aspect of the invention provides formulations comprising particles formed by the compounds of any of formula I-VI and the biologically active molecule.

Another aspect of the invention provides a formulation comprising the compounds of any of formula I-VI and a biologically active molecule, where the biologically active molecule and the compound form a lipoplex.

Another aspect of the invention provides a formulation comprising the compounds of any of formula I-VI and a biologically active molecule, where the biologically active molecule is at least partially within a liposome formed by the compound.

Another aspect of the invention provides a formulation comprising the compounds of any of formula I-VI and a biologically active molecule, where the biologically active molecule is encapsulated within the liposome.

In one embodiment, the invention provides formulations where the particles have a median diameter of less than about 500 nm.

One aspect of the invention provides methods of introducing siRNA into a cell, comprising contacting the cell with a formulation of the invention, where the formulation comprises a compound of any of Formulae I-VI and a siRNA.

Another aspect of the invention provides methods of introducing synthetic shRNA into a cell, comprising contacting the cell with a formulation of the invention, where the formulation comprises a compound of any of Formulae I-VI and a shRNA.

In yet another aspect of the invention provides methods of introducing miRNA into a cell, comprising contacting the cell with a formulation of the invention, where the formulation comprises a compound of any of Formulae I-VI and a miRNA.

Another aspect of the invention provides methods of introducing antisense nucleic acid into a cell, comprising contacting the cell with a formulation of the invention, where the formulation comprises a compound of any of Formulae I-VI and an antisense nucleic acid.

One aspect of the invention provides methods of modulating expression of a target sequence, said method comprising administering to a mammalian subject a therapeutically effective amount of a formulation comprising a compound of any of formulae I-VI and a biologically active molecule.

Another aspect of the invention provides methods for in vivo delivery of siRNA, said method comprising administering to a mammalian subject a therapeutically effective amount of a formulation of the invention.

Another aspect of the invention provides methods of treating or preventing a disease in a mammalian subject, said method comprising administering to said subject a therapeutically effective amount of a formulation comprising a compound of any of formulae I-VI and a biologically active molecule.

Another aspect of the invention provides methods for inhibiting expression of a gene, comprising contacting a cell with a formulation comprising a biologically active molecule capable of inhibiting expression of the gene and a compound of any of formulae I-VI. In one embodiment, the cell is a mammalian cell, preferably a human cell. Further, these methods may be carried out in vivo or in vitro. In one embodiment, the biologically active molecule is selected from the group consisting of, for example, siRNA, shRNA, miRNA, antisense nucleic acid, ribosomal RNA, antisense polynucleotides of RNA or DNA, ribozymes, and polynucleotides of genomic DNA, cDNA, or mRNA that encode for a therapeutically useful protein. Such formulations may also include cholesterol, hormones, antivirals, peptides, chemotherapeutics, small molecules, vitamins, co-factors, or proteins such as antibodies.

In another aspect of the invention, biologically active molecules that do not inhibit gene expression, e.g., various small molecule pharmaceutical compounds, can be contained in formulations with compounds of the invention for use in therapies other than those involving inhibition of gene expression.

In another embodiment, the invention provides implantable or injectable devices containing a formulation of (i) one or more of the compounds of any of formula I-VI and (ii) one or more biologically active molecules. In these devices, the formulation is entrapped or encapsulated within the device and the device, in addition to the formulation, comprises a biodegradable and/or biocompatible drug release material. The device will be of a size and shape suitable for injection into or implantation within the body of a subject, preferably a mammalian, more preferably a human, subject.

As noted above, particular compounds of the invention include a polymer moiety, G, $G_1$, or $G_2$. These polymer groups have molecular weights ranging from about 200 Da to about 10,000 Da.

The polymer moieties are preferably polyoxyalkylenes or comprise two or more polyoxyalkylene groups or units. A polyoxyalkylene group is formed by polymerizing alkylene oxide monomers to provide polymer moieties of desired size and weight. Where the polymer moiety comprises two or more polyoxyalkylene groups, the individual polyoxyalkylene groups are connected to each other by linker groups. Examples of suitable linker groups are:

—C(O)—, —O—, —O—C(O)O—, —C(O)CH$_2$CH$_2$C(O)—, —S—S—, —NR$^3$—, —NR$^3$C(O)O—, —OC(O)NR$^3$—, —NR$^3$C(O)—, —C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)—, -alkylene-C(O)NR$^3$—, —NR$^3$C(O)O-alkylene-, —NR$^3$C(O)NR$^3$-alkylene-, —OC(O)NR$^3$-alkylene, —NR$^3$-alkylene-, —O-alkylene-, —NR$^3$C(O)-alkylene-, —C(O)NR$^3$-alkylene-, -alkylene-NR$^3$C(O)O-alkylene-, -alkylene-NR$^3$C(O)NR$^3$-alkylene-, -alkylene-OC(O)NR$^3$-alkylene-, -alkylene-NR$^3$-alkylene-, -alkylene-O-alkylene-, -alkylene-NR$^3$C(O)-alkylene-, —C(O)NR$^3$-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —C(O)NR$^3$-alkyleneoxy-, and -alkyleneoxy-NR$^3$C(O)O-alkyleneoxy-, where R$^3$ is hydrogen, or optionally substituted alkyl, and

where

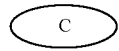

is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR³—, —NR³C(O)O—, —OC(O)NR³—, —NR³C(O)—, —C(O)NR³—, —NR³C(O)NR³—, -alkylene-NR³C(O)O—, -alkylene-NR³C(O)NR³—, -alkylene-OC(O)NR³—, -alkylene-NR³—, -alkylene-O—, -alkylene-NR³C(O)—, -alkylene-C(O)NR³—, —NR³C(O)O-alkylene-, —NR³C(O)NR³-alkylene-, —OC(O)NR³-alkylene-, —NR³-alkylene-, —O-alkylene-, —NR³C(O)-alkylene-, —NR³C(O)O-alkyleneoxy-, —NR³C(O)NR³-alkyleneoxy-, —OC(O)NR³-alkyleneoxy, —NR³-alkyleneoxy-, —O-alkyleneoxy-, —NR³C(O)-alkyleneoxy-, —C(O)NR³-alkyleneoxy-, -alkyleneoxy-NR³C(O)O-alkyleneoxy-, —C(O)NR³-alkylene-, -alkylene-NR³C(O)O-alkylene-, -alkylene-NR³C(O)NR³-alkylene-, -alkylene-OC(O)NR³-alkylene-, -alkylene-NR³-alkylene-, -alkylene-O-alkylene-, -alkylene-NR³C(O)-alkylene-, and —C(O)NR³-alkylene-, where R³ is as defined above.

Preferred linker groups are —C(O)—, —O—, —NR³—, —NR³C(O)O—, —OC(O)NR³—, —NR³C(O)—, and —C(O)NR³—, where each R³ is as defined above.

Where G, $G_1$, or $G_2$ is formed from independent units linked by, for example, amide groups, the units may be selected from shorter chain polymers or units having a wide range of sizes and molecular weights. As noted above, polymers G, $G_1$, and $G_2$, may have molecular weights of from about 200-10,000 Da; any of these polymers may be formed from several shorter, independently-sized units. The units may have molecular weights independently ranging from about 50 (i.e., one repeating unit of a polyethylene glycol), 200, or 500 Da up to about 3000, 4000 or 5000 Da.

Thus, where a compound includes a polymer moiety G, $G_1$, or $G_2$, having a molecular weight of about 3000 Da, the polymer may, for example, (a) be a polyoxyethylene group having a molecular weight of about 3000 Da;
(b) consist of four polyoxyethylene groups covalently bound to each other by three amide linker (—C(O)NH—) groups, where each of the polyoxyalkylene groups has a molecular weight of about 750 Da, such that the polymer moiety has molecular weight of about 3000 Da; or
(c) consist of five polyoxyethylene groups covalently bound to each other by four amide linker (—C(O)NH—) groups, where the five polyoxyalkylene groups have molecular weights of about 500, 1000, 250, 1000, and 250 Da, respectively.

These polymer moieties are included only as examples; those skilled in the art will recognize other polymer moieties that can be suitably employed in the compounds of the invention.

Non-limiting examples of reagents useful for making the polymer moieties of the invention include the following:

| | |
|---|---|
| HO(alkylene-O)$_{pp}$R$^{bb}$ | mono-capped mono-hydroxy PEG (mPEG) |
| H$_2$N(alkylene-O)$_{pp}$R$^{bb}$ | mono-capped mono-amino PEG |
| HO(alkylene-O)$_{pp}$R—OH | non-capped di-hydroxy PEG |
| H$_2$N(alkylene-O)$_{pp}$R—OH | non-capped mono-amino PEG | where pp and alkylene are as defined herein and $R^{bb}$ is preferably selected from the group consisting of alkyl and substituted alkyl.

Specific examples of such reagents include:

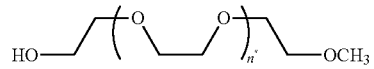

mono-capped mono-hydroxy PEG (mPEG),

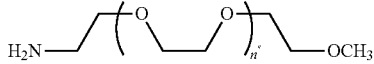

mono-capped mono-amine PEG, and

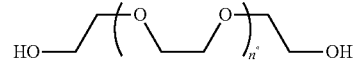

non-capped di-hydroxy PEG.

In some embodiments, the particles are made by providing an aqueous solution in a first reservoir and an organic lipid solution (i.e., a solution of a compound of the invention in water) in a second reservoir and mixing the aqueous solution with the organic lipid solution so as to substantially instantaneously produce a liposome encapsulating, e.g., an interfering RNA. In some embodiments, the particles are made by formation of hydrophobic intermediate complexes in either detergent-based or organic solvent-based systems, followed by removal of the detergent or organic solvent. Preferred embodiments are charge-neutralized.

In one embodiment, the interfering RNA is transcribed from a plasmid and the plasmid is combined with cationic lipids in a detergent solution to provide a coated nucleic acid-lipid complex. The complex is then contacted with non-cationic lipids to provide a solution of detergent, a nucleic acid-lipid complex and non-cationic lipids, and the detergent is then removed to provide a solution of serum-stable nucleic acid-lipid particles, in which the plasmid comprising an interfering RNA template is encapsulated in a lipid bilayer. The particles thus formed have a size of about 50-500 nm.

In another embodiment, stable lipid particles are formed by preparing a mixture of cationic lipids and non-cationic lipids in an organic solvent; contacting an aqueous solution of nucleic acids comprising, e.g., interfering RNA with the mixture of cationic and non-cationic lipids to provide a clear single phase; and removing the organic solvent to provide a suspension of nucleic acid-lipid particles, in which the nucleic acid is encapsulated in a lipid bilayer, and the particles are stable in serum and have a size of about 50-500 nm.

Particles and complexes of the invention, e.g., complexes of a compound of any of formula I-VI with a siRNA, having desired sizes and/or charge can be obtained by passing mixtures prepared as above through suitable filters. See, e.g., Examples 32 and 33 below.

The lipid particles of the invention are useful for the therapeutic delivery of nucleic acids comprising a siRNA sequence. In particular, it is an object of this invention to provide in vitro and in vivo methods for treatment of a disease in a mammal by downregulating or silencing the translation of a target nucleic acid sequence. In these methods, a siRNA molecule is formulated into a nucleic acid-lipid particle, and the particles are administered to patients requiring such treatment (e.g., a patient diagnosed with a disease or disorder associated with the expression or overexpression of a gene comprising the target nucleic acid sequence). Alternatively, cells are removed from a patient, the siRNA is delivered in vitro, and the cells are reinjected into the patient. In one embodiment, the present invention provides for a method of introducing a siRNA molecule into a cell by contacting a cell with a nucleic acid-lipid particle comprising of a cationic lipid, a non-cationic lipid, a conjugated lipid that inhibits aggregation, and a siRNA. In another embodiment, the present invention provides for a method of introducing a siRNA molecule into a cell by contacting a cell with a nucleic acid-lipid particle comprising of a cationic lipid, a conjugated lipid that inhibits aggregation, and a siRNA. In yet another embodiment, the present invention provides for a method of introducing a siRNA molecule into a cell by contacting a cell with a nucleic acid-lipid particle comprising of a cationic lipid, and a siRNA.

The lipid particle may be administered, e.g., intravenously, or intraperitoneally. In one embodiment, at least about 10% of the total administered dose of the nucleic acid-lipid particles is present in plasma about 1, 6, 12, 24, 36, 48, 60, 72, 84, or 96 hours after injection. In other embodiments, more than 20%, 30%, 40% and as much as 60%, 70% or 80% of the total injected dose of the nucleic acid-lipid particles is present in plasma 1, 6, 12, 24, 36, 48, 60, 72, 84, or 96 hours after injection. In one embodiment, the presence of a siRNA in cells in a target tissue (i.e., lung, liver, tumor, vascular endothelium or at a site of inflammation) is detectable at 24, 48, 72 and 96 hours after administration. In one embodiment, downregulation of expression of the target sequence is detectable at 24, 48, 72 and 96 hours after administration. In one embodiment, downregulation of expression of the target sequence occurs preferentially in tumor cells or in cells at a site of inflammation or any other disease tissue. In one embodiment, the presence of a siRNA in cells at a site distal to the site of administration is detectable at least four days after intravenous injection of the nucleic acid-lipid particle. In another embodiment, the presence of a siRNA in of cells in a target tissue (i.e., lung, liver, tumor or at a site of inflammation) is detectable at least four days after injection of the nucleic acid-lipid particle.

The particles are suitable for use in intravenous nucleic acid transfer as they are stable in circulation, of a size required for pharmacodynamic behavior resulting in access to extravascular sites and target cell populations. The invention also provides for pharmaceutically acceptable compositions comprising a lipid particle.

The particles are suitable for use in intravenous nucleic acid transfer as they are stable in circulation, of a size required for pharmacodynamic behavior resulting in access to extravascular sites and target cell populations.

The stable nucleic acid-lipid particles described herein typically comprise a nucleic acid (e.g., a siRNA sequence or a DNA sequence encoding a siRNA sequence), a cationic lipid, a noncationic lipid and a bilayer stabilizing component such as, e.g., a conjugated lipid that inhibits aggregation of the lipid particles. The lipid particles of the present invention have a mean diameter of less than about 500 nm and are substantially nontoxic. In addition, nucleic acids encapsulated in the lipid particles of the present invention are resistant in aqueous solution to degradation with a nuclease.

The nucleic acid component of the nucleic acid-lipid particles typically comprise an interfering RNA (i.e., siRNA), which can be provided in several forms including, e.g. as one or more isolated small-interfering RNA (siRNA) duplexes, longer double-stranded RNA (dsRNA) or as siRNA or dsRNA transcribed from a transcriptional cassette in a DNA plasmid.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected etc.), or can represent a single target sequence. RNA can be naturally occurring, e.g., isolated from tissue or cell samples, synthesized in vitro, e.g., using T7 or SP6 polymerase and PCR products or a cloned cDNA; or chemically synthesized.

To form a long dsRNA, for synthetic RNAs, the complement is also transcribed in vitro and hybridized to form a ds RNA. If a naturally occurring RNA population is used, the RNA complements are also provided (e.g., to form dsRNA for digestion by E. coli RNAse III or Dicer), e.g., by transcribing cDNAs corresponding to the RNA population, or by using RNA polymerases. The precursor RNAs are then hybridized to form double stranded RNAs for digestion. The dsRNAs can be directly encapsulated in the nucleic acid-lipid particles or can be digested in vitro prior to encapsulation.

Alternatively, one or more DNA plasmids encoding one or more siRNA templates are encapsulated in a nucleic acid-lipid particle. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp, et al., Science 296: 550 (2002); Donze, et al., Nucleic Acids Res. 30:e46 (2002); Paddison, et al., Genes Dev. 16:948 (2002); Yu, et al., Proc. Natl. Acad. Sci. 99:6047 (2002); Lee, et al., Nat. Biotech. 20:500 (2002); Miyagishi, et al., Nat. Biotech. 20:497 (2002); Paul, et al., Nat. Biotech. 20:505 (2002); and Sui, et al., Proc. Natl. Acad. Sci. 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp, Science, supra). The selected promoter can provide for constitutive or inducible transcription. Compositions and methods for DNA-directed transcription of RNA interference molecules is described in detail in U.S. Pat. No. 6,573,099, incorporated herein by reference. Preferably, the synthesized or transcribed siRNA have 3' overhangs of about 1-4 nucleotides, preferably of about 2-3 nucleotides and 5' phosphate termini (Elbashir, et al., Genes Dev. 15:188 (2001); Nykanen, et al., Cell 107:309 (2001)). The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488, both of which are incorporated herein by reference. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler & Hoffman, Gene 25:263-269 (1983); Sambrook et al., supra; Ausubel et al., supra), as are PCR methods (see U.S. Pat. Nos. 4,683,195 and 4,683,202; PCR Protocols: A Guide to Methods and Applications (Innis et al., eds, 1990)). Expression libraries are also well known to those of skill in the art. Additional basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

Generally, it is desired to deliver the nucleic acid-lipid particles to downregulate or silence the translation (i.e., expression) of a gene product of interest. Suitable classes of gene products include, but are not limited to, genes associated with viral infection and survival, genes associated with metabolic diseases and disorders (e.g., diseases and disorders in which the liver is the target, and liver diseases and disorders) and disorders, genes associated with tumorigenesis and cell transformation, angiogenic genes, immunomodulator genes, such as those associated with inflammatory and autoimmune responses, ligand receptor genes, and genes associated with neurodegenerative disorders.

Genes associated with viral infection and survival include those expressed by a virus in order to bind, enter and replicate in a cell. Of particular interest are viral sequences associated with chronic viral diseases. Viral sequences of particular interest include sequences of Hepatitis viruses (Hamasaki, et al., FEBS Lett. 543:51 (2003); Yokota, et al., EMBO Rep. 4:602 (2003); Schlomai, et al., Hepatology 37:764 (2003); Wilson, et al., Proc. Natl. Acad. Sci. 100:2783 (2003); Kapadia, et al., Proc. Natl. Acad. Sci. 100:2014 (2003); and FIELDS VIROLOGY (Knipe et al. eds. 2001)), Human Immunodeficiency Virus (HIV) (Banerjea, et al., Mol. Ther. 8:62 (2003); Song, et al., J. Virol. 77:7174 (2003); Stephenson JAMA 289:1494 (2003); Qin, et al., Proc. Natl. Acad. Sci. 100:183 (2003)), Herpes viruses (Jia, et al., J. Viral. 77:3301 (2003)), and Human Papilloma Viruses (HPV) (Hall, et al., J. Viral. 77:6066 (2003); Jiang, et al., Oncogene 21:6041 (2002)). Exemplary hepatitis viral nucleic acid sequences that can be silenced include but are not limited to: nucleic acid sequences involved in transcription and translation (e.g., En1, En2, X, P), nucleic acid sequences encoding structural proteins (e.g., core proteins including C and C-related proteins; capsid and envelope proteins including S, M, and/or L proteins, or fragments thereof) (see, e.g., FIELDS VIROLOGY, 2001, supra). Exemplary Hepatitis C nucleic acid sequences that can be silenced include but are not limited to: serine proteases (e.g., NS3/NS4), helicases (e.g. NS3), polymerases (e.g., NS5B), and envelope proteins (e.g., E1, E2, and p7). Hepatitis A nucleic acid sequences are set forth in e.g., Genbank Accession No. NC_001489; Hepatitis B nucleic acid sequences are set forth in, e.g., Genbank Accession No. NC_003977; Hepatitis C nucleic acid sequences are set forth in, e.g., Genbank Accession No. NC_004102; Hepatitis D nucleic acid sequence are set forth in, e.g., Genbank Accession No. NC_001653; Hepatitis E nucleic acid sequences are set forth in e.g., Genbank Accession No. NC_001434; and Hepatitis G nucleic acid sequences are set forth in e.g., Genbank Accession No. NC_001710. Silencing of sequences that encode genes associated with viral infection and survival can conveniently be used in combination with the administration of conventional agents used to treat the viral condition.

Genes associated with metabolic diseases and disorders (e.g., disorders in which the liver is the target and liver diseases and disorders) include, for example genes expressed in, for example, dyslipidemia (e.g., liver X receptors (e.g., LXRα and LXRβ, Genback Accession No. NM_007121), farnesoid X receptors (FXR) (Genback Accession No. NM_005123), sterol-regulatory element binding protein (SREBP), Site-1 protease (S1P), 3-hydroxy-3-methylglutaryl coenzyme-A reductase (HMG coenzyme-A reductase), Apolipoprotein (ApoB), and Apolipoprotein (ApoE)) and diabetes (e.g., Glucose 6-phosphatase) (see, e.g., Forman et al., Cell 81:687 (1995); Seol et al., Mol. Endocrinol. 9:72 (1995), Zavacki et al., PNAS USA 94:7909 (1997); Sakai, et al., Cell 85:1037-1046 (1996); Duncan, et al., J. Biol. Chem. 272:12778-12785 (1997); Willy, et al., Genes Dev. 9(9):1033-45 (1995); Lehmann, et al., J. Biol. Chem. 272(6): 3137-3140 (1997); Janowski, et al., Nature 383:728-731 (1996); Peet, et al., Cell 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder.

Examples of gene sequences associated with tumorigenesis and cell transformation include translocation sequences such as MLL fusion genes, BCR-ABL (Wilda, et al., Oncogene, 21:5716 (2002); Scherr, et al., Blood 101: 1566), TEL-AML1, EWS-FLI1, TLS-FUS, PAX3-FKHR, BCL-2, AML1-ETO and AML1-MTG8 (Heidenreich, et al., Blood 101:3157 (2003)); overexpressed sequences such as multidrug resistance genes (Nieth, et al., FEBS Lett. 545:144 (2003); Wu, et al, Cancer Res. 63:1515 (2003)), cyclins (Li, et al., Cancer Res. 63:3593 (2003); Zou, et al., Genes Dev. 16:2923 (2002)), beta-Catenin (Verma, et al., Clin Cancer Res. 9:1291 (2003)), telomerase genes (Kosciolek, et al., Mol Cancer Ther. 2:209 (2003)), c-MYC, N-MYC, BCL-2, ERBB1 and ERBB2 (Nagy, et al. Exp. Cell Res. 285:39 (2003)); and mutated sequences such as RAS (reviewed in Tuschl and Borkhardt, Mol. Interventions, 2:158 (2002)). Silencing of sequences that encode DNA repair enzymes find use in combination with the administration of chemotherapeutic agents (Collis, et al., Cancer Res. 63:1550 (2003)). Genes encoding proteins associated with tumor migration are also target sequences of interest, for example, integrins, selectins and metalloproteinases. The foregoing examples are not exclusive. Any whole or partial gene sequence that facilitates or promotes tumorigenesis or cell transformation, tumor growth or tumor migration can be included as a template sequence Angiogenic genes are able to promote the formation of new vessels. Of particular interest is Vascular Endothelial Growth Factor (VEGF) (Reich, et al., Mol. Vis. 9:210 (2003)).

Immunomodulator genes are genes that modulate one or more immune responses. Examples of immunomodulator genes include cytokines such as growth factors (e.g., TGF-α, TGF-β, EGF, FGF, IGF, NGF, PDGF, CGF, GM-CSF, SCF, etc.), interleukins (e.g., IL-2, IL-4, IL-12 (Hill, et al., J. Immunol. 171:691 (2003)), IL-15, IL-18, IL-20, etc.), interferons (e.g., IFN-α, IFN-β, IFN-γ, etc.) and TNF. Fas and Fas Ligand genes are also immunomodulator target sequences of Interest (Song, et al., Nat. Med. 9:347 (2003)). Genes encoding secondary signaling molecules in hematopoietic and lymphoid cells are also included in the present invention, for example, Tec family kinases, such as Bruton's tyrosine kinase (Btk) (Heinonen, et al., FEBS Lett. 527:274 (2002)).

Cell receptor ligands of the invention can be proteins or steroid molecules. Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell surface receptor ligands include cytokines, growth factors, interleukins, interferons, erythropoietin (EPO), insulin, glucagon, G-protein coupled receptor ligands, etc.). Templates coding for an expansion of trinucleotide repeats (e.g., CAG repeats), find use in silencing pathogenic sequences in neurodegenerative disorders caused by the expansion of trinucleotide repeats, such as spinobulbular muscular atrophy and Huntington's Disease (Caplen, et al., Hum. Mol. Genet. 11:175 (2002)). Cell receptor ligands also include ligands that do not bind to cell surface receptors but to intracellular receptors (e.g., steroid receptors located in the nucleus, and cytoplasm, inositol phosphate receptors located in the endoplasmic reticulum). Examples of intracellular receptor ligands include lipophilic hormones like steroid hormones, inositol trisphosphate, and intracrine peptide hormones.

DEFINITIONS

As used herein, the term "alkyl" includes those alkyl groups containing from 1 to 10 carbon atoms. Alkyl groups may be straight, or branched. Examples of "alkyl" include methyl, ethyl, propyl, isopropyl, butyl, iso-, sec- and tert-butyl, pentyl, isopentyl, hexyl, 3-methylhexyl, heptyl, octyl, nonyl, 3-ethylbutyl, and the like. A preferred alkyl group is $C_1$-$C_6$ alkyl. The alkyl groups of the invention may be optionally substituted with various groups as provided herein. Thus, any carbon atom available for substitution may be further bonded to a variety of substituents, such as, for example, halogen, OH, $NO_2$, CN, $NH_2$, $C_1$-$C_8$ alkyl, $C_1$-$C_8$ alkoxy, NH($C_1$-$C_8$ alkyl). N($C_1$-$C_8$ alkyl) ($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_8$)alkoxy, oxo, amino($C_1$-$C_8$)alkyl, mono- and di($C_1$-$C_8$ alkyl)amino($C_1$-$C_8$)alkyl, $C_1$-$C_8$ acyl, $C_1$-$C_8$ acyloxy, $C_1$-$C_8$ sulfonyl, $C_1$-$C_8$ thio, $C_1$-$C_8$ sulfonamido, and $C_1$-$C_8$ aminosulfonyl.

The term "alkylene" refers to divalent saturated aliphatic hydrocarbyl groups preferably having from 1 to 5 and more preferably 1 to 3 carbon atoms which are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) and the like.

The term "alkyleneoxy" refers to divalent saturated aliphatic hydrocarbyl groups bound to an oxygen, where the aliphatic hydrocarbyl groups preferably have from 1 to 5 and more preferably 1 to 3 carbon atoms which are either straight-chained or branched.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, anthracenyl 1,2,3,4-tetrahydronaphthalene, indenyl, 2,3-dihydroindenyl, and biphenyl. Preferred examples of aryl groups include phenyl, naphthyl, 1,2,3,4-tetrahydronaphthalene, and 2,3-dihydroindenyl. More preferred aryl groups are phenyl and naphthyl. Most preferred is phenyl. The aryl groups of the invention may be optionally substituted with various groups as provided herein. Thus, any carbon atom present within an aryl ring system and available for substitution may be further bonded to a variety of ring substituents, such as, for example, halogen, OH, $NO_2$, CN, $NH_2$, $C_1$-$C_8$ alkyl, $C_1$-$C_8$ alkoxy, NH($C_1$-$C_8$ alkyl), N($C_1$-$C_8$ alkyl) ($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_8$) alkoxy, oxo, amino($C_1$-$C_8$)alkyl, mono- and di($C_1$-$C_8$ alkyl)amino($C_1$-$C_8$)alkyl, $C_1$-$C_8$ acyl, $C_1$-$C_8$ acyloxy, $C_1$-$C_8$ sulfonyl, $C_2$-$C_8$ thio, $C_1$-$C_8$ sulfonamido, and $C_1$-$C_8$ aminosulfonyl.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl. More preferred are $C_3$-$C_6$ cycloalkyl groups. The cycloalkyl groups of the invention may be optionally substituted with various groups as provided herein. Thus, any carbon atom present within a cycloalkyl ring system and available for substitution may be further bonded to a variety of ring substituents, such as, for example, halogen, OH, $NO_2$, CN, NH, $C_1$-$C_8$ alkyl, $C_1$-$C_8$ alkoxy, NH($C_1$-$C_3$ alkyl), N($C_1$-$C_8$ alkyl)($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_3$)alkoxy, oxo, amino($C_1$-$C_3$)alkyl, mono- and di($C_1$-$C_8$alkyl)amino($C_1$-$C_8$) alkyl.

The term "heterocycloalkyl" refers to a ring or ring system containing at least one heteroatom selected from nitrogen, oxygen, and sulfur, wherein said heteroatom is in a non-aromatic ring and the ring system is attached to the parent group by a member of (one of) the non-aromatic ring(s). The heterocycloalkyl ring is optionally fused to other heterocycloalkyl rings and/or non-aromatic hydrocarbon rings, and/or phenyl rings. Thus, heterocycloalkyl groups suitable for the invention have at least 3 members, and may have up to 20 members. Preferred heterocycloalkyl groups have from 3 to 10 members. Certain more preferred heterocycloalkyl groups have from 8-10 members. Other more preferred heterocycloalkyl groups have 5 or 6 members. Examples of heterocycloalkyl groups include, for example, 1,2,3,4-tetrahydroisoquinolinyl, 1,2-dihydroquinolinyl, 1,2,3,4-tetrahydroquinolinyl, benzo[1,4]oxazinyl, 2,3-dihydrobenzo [1,4]oxazinyl, indolinyl, benzo[1,3]dioxolyl, 2H-chromenyl, piperazinyl, morpholinyl, piperidinyl, piperazinyl, tetrahydrofuranyl, pyrrolidinyl, pyridinonyl, azetidinyl, aziridinyl, and pyrazolidinyl. Preferred heterocycloalkyl groups includepiperidinyl, piperazinyl, morpholinyl, pyrrolidinyl, pyridinonyl, dihydropyrrolidinyl, azetidinyl, aziridinyl, 2,3, 4-tetrahydroquinolinyl, 2,3-dihydrobenzo[1,4]oxazinyl, indolinyl, benzo[1,3]dioxolyl, and pyrrolidinonyl. More preferred heterocycloalkyl groups are pyrrolidinly, piperidinyl, azetidinyl, aziridinyl, piperazinyl, morpholinyl, 1,2,3,4-tetrahydroquinolinyl, 2,3-dihydrobenzo[1,4]oxazinyl, indolinyl, and benzo[1,3]dioxolyl. The heterocycloalkyl groups of the invention may be optionally substituted with various groups as provided herein. Thus, any atom present within a heterocycloalkyl ring and available for substitution may be further bonded to a variety of ring substituents, such as, for example, halogen, OH, $NO_2$, CN, $NH_2$, $C_1$-$C_8$ alkyl, $C_1$-$C_8$ alkoxy, NH($C_1$-$C_8$ alkyl), N($C_1$-$C_8$ alkyl) ($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_8$)alkoxy, oxo, amino($C_1$-$C_8$)alkyl and mono- and di($C_1$-$C_8$ alkyl)amino($C_1$-$C_8$)alkyl.

The term "heteroaryl" refers to an aromatic ring system containing at least one heteroatom selected from nitrogen, oxygen, and sulfur and the ring system is attached to the parent group by a member of (one of) the aromatic ring(s). The heteroaryl ring may be fused to one or more heteroaryl rings, aromatic or non-aromatic hydrocarbon rings or heterocycloalkyl rings. Thus, heteroaryl groups suitable for the invention have at least 5 members, and may have up to 20 members. Examples of heteroaryl groups include, for example, pyridine, furan, thienyl, 5,6,7,8-tetrahydroisoquinolinyl and pyrimidinyl. Preferred heteroaryl groups include thienyl, benzothienyl, pyridyl, quinolinyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, 5,6-dihydroquinazolinyl, 4,5,6,7-tetrahydroindolyl, 4,5-dihydro-2H-indazolyl, 5,6-dihydroquinolinyl, pyrazolyl, and benzopyrazolyl. More preferred heteroaryl groups are benzothiazolyl, pyridyl, pyrazolyl, and quinolinyl. The heteroaryl groups of the invention may be optionally substituted with various groups as provided herein. Thus, any carbon atom present within an heteroaryl ring system and available for substitution may be further bonded to a variety of ring substituents, such as, for example, halogen, OH, $NO_2$, CN, $NH_2$, $C_1$-$C_8$ alkyl, $C_1$-$C_8$ alkoxy, $NH(C_1$-$C_8$ alkyl), $N(C_1$-$C_8$ alkyl)($C_1$-$C_8$ alkyl), $C_3$-$C_{10}$ cycloalkyl, ($C_3$-$C_{10}$ cycloalkyl)alkyl, ($C_3$-$C_{10}$ cycloalkyl)alkoxy, $C_2$-$C_9$ heterocycloalkyl, $C_1$-$C_8$ alkenyl, $C_1$-$C_8$ alkynyl, halo($C_1$-$C_8$)alkyl, halo($C_1$-$C_8$)alkoxy, oxo, amino($C_1$-$C_8$)alkyl and mono- and di($C_1$-$C_8$ alkyl)amino($C_1$-$C_8$)alkyl.

By "anti-proliferative activity" as used herein is meant biological activity against any disease, condition, trait, genotype or phenotype characterized by unregulated cell growth or replication as is known in the art; including leukemias, for example, acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and any other cancer or proliferative disease, condition, trait, genotype or phenotype that can respond to the modulation of disease related gene expression in a cell or tissue, alone or in combination with other therapies.

The term "aptamer" means a nucleic acid that binds to another molecule. This binding interaction does not encompass standard nucleic acid/nucleic acid hydrogen bond formation exemplified by Watson-Crick basepair formation (e.g., A binds to U or T and G binds to C), but encompasses all other types of non-covalent (or in some cases covalent) binding. Non-limiting examples of non-covalent binding include hydrogen bond formation, electrostatic interaction, Van der Waals interaction and hydrophobic interaction. An aptamer may bind to another molecule by any or all of these types of interaction, or in some cases by covalent interaction. Covalent binding of an aptamer to another molecule may occur where the aptamer or target molecule contains a chemically reactive or photoreactive moiety. The term "aptamer" refers to a nucleic acid that is capable of forming a complex with an intended target substance. "Target-specific" means that the aptamer binds to a target analyte with a much higher degree of affinity than it binds to contaminating materials.

The term "biologically active molecule" as used herein refers to compounds or molecules that are capable of eliciting or modifying a biological response in a system. Non-limiting examples of biologically active molecules include antibodies (e.g., monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids (e.g., ribozymes, etc.), antisense nucleic acids, triplex forming oligonucleotides, 2,5-A chimeras, dsRNA, (e.g., siNA, siRNA, etc.), allozymes, aptamers, decoys, ribosomal RNA, antisense polynucleotides of RNA or DNA or combinations of RNA and DNA, miRNA, shRNA, and polynucleotides of genomic DNA, cDNA, or mRNA that encode for a therapeutically useful protein, and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers. In certain embodiments, the term biologically active molecule is used interchangeably with the term "molecule" or "molecule of interest" herein.

By "cationic lipid" as used herein is meant any lipophilic compound having a net positive charge at about physiological pH, such as a compound having any of Formulae I-VI.

By "neutral lipid" as used herein is meant any lipophilic compound other than a cationic lipid as defined herein that does not bear a net charge at about physiological pH. Suitable compounds having no net charge at about physiological pH include zwitterions.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The term "double stranded RNA" or "dsRNA" as used herein refers to a double stranded RNA molecule capable of RNA interference, including short interfering RNA (siRNA).

By "gene" is meant a nucleic acid that encodes RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof.

By "inhibit" or "inhibition", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules and the molecules of the invention. In one embodiment, inhibition with a siNA molecule is below that level observed in the presence of an inactive or attenuated molecule. In another embodiment, inhibition with siNA molecules is below that level observed in the presence of, for example, a siNA molecule with scrambled sequence or with mismatches. In another embodiment, inhibition of gene expression with a nucleic acid molecule of the instant invention is greater in the presence of the nucleic acid molecule than in its absence. In one embodiment, inhibition of gene expression is associated with post transcriptional silencing, such as RNAi mediated cleavage of a target nucleic acid molecule (e.g. RNA) or inhibition of translation. In one embodiment, inhibition is associated with pretranscriptional silencing.

The terms "linker" and "linker group" refer to polyvalent, preferably divalent, moieties that connect one or more molecules to each other. Examples are moieties that connect portions of a polymer moiety G together or connect a targeting ligand T to a polymer moiety G. Linkers can be biodegradable or biostable. Biodegradable linkers are designed such that their stability can be modulated for a particular purpose, such as delivery to a particular tissue or cell type. Examples of suitable linker groups include the following groups: —C(O)—, —O—, —O—C(O)O—, —C(O)CH$_2$CH$_2$C(O)—, —S—S—, —NR$^3$—, —NR$^3$C(O)O—, —OC(O)NR$^3$—, —NR$^3$C(O)—C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)-alkylene-C(O)NR$^3$—, —NR$^3$C(O)O-alkylene-, —NR$^3$C(O)NR$^3$-alkylene-, —OC(O)NR$^3$-alkylene, —NR$^3$-alkylene-, —O-alkylene-, —NR$^3$C(O)-alkylene-, —C(O)NR$^3$-alkylene-, -alkylene-NR$^3$C(O)O-alkylene-, -alkylene-NR$^3$C(O)NR$^3$-alkylene-, -alkylene-OC(O)NR$^3$-alkylene-, -alkylene-NR$^3$-alkylene-, -alkylene-O-alkylene-, -alkylene-NR$^3$C(O)-alkylene-, —C(O)NR$^3$-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —C(O)NR$^3$-alkyleneoxy-, and -alkyleneoxy-NR$^3$C(O)O-alkyleneoxy-, where R$^3$ is hydrogen, or optionally substituted alkyl, and

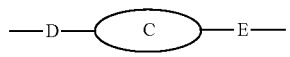

where

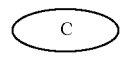

is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR$^3$—, —NR$^3$C(O)O—, —OC(O)NR$^3$—, —NR$^3$C(O)—, —C(O)NR$^3$—, —NR$^3$C(O)NR$^3$—, -alkylene-NR$^3$C(O)O—, -alkylene-NR$^3$C(O)NR$^3$—, -alkylene-OC(O)NR$^3$—, -alkylene-NR$^3$—, -alkylene-O—, -alkylene-NR$^3$C(O)—, alkylene-C(O)NR$^3$—, —NR$^3$C(O)O-alkylene-, —NR$^3$C(O)NR$^3$-alkylene-, —OC(O)NR$^3$-alkylene-, —NR$^3$-alkylene-, —O-alkylene-, —NR$^3$C(O)-alkylene-, —NR$^3$C(O)O-alkyleneoxy-, —NR$^3$C(O)NR$^3$-alkyleneoxy-, —OC(O)NR$^3$-alkyleneoxy, —NR$^3$-alkyleneoxy-, —O-alkyleneoxy-, —NR$^3$C(O)-alkyleneoxy-, —C(O)NR$^3$-alkyleneoxy-, -alkyleneoxy-NR$^3$C(O)O-alkyleneoxy-, —C(O)NR$^3$-alkylene-, -alkylene-NR$^3$C(O)O-alkyleneoxy-, —C(O)NR$^3$-alkylene-, -alkylene-NR$^3$C(O)NR$^3$-alkylene-, -alkylene-OC(O)NR$^3$-alkylene-, and —C(O)NR$^3$-alkylene-, where R$^3$ is as defined above.

The term "targeting ligand" refers to any compound or molecule, such as a drug, peptide, hormone, or neurotransmitter that is capable of interacting with another compound, such as a receptor, either directly or indirectly. The receptor that interacts with a ligand can be present on the surface of a cell or can alternately be an intercellular receptor. Interaction of the ligand with the receptor can result in a biochemical reaction, or can simply be a physical interaction or association. Non-limiting examples of ligands include pharmacologically active small molecules, endosomolytic agents, fusogenic peptides, cell membrane permeating agents, charge masking agents, and nucleic acids. Other non-limiting examples of ligands include sugars and carbohydrates such as galactose, galactosamine, and N-acetyl galactosamine; hormones such as estrogen, testosterone, progesterone, glucocortisone, adrenaline, insulin, glucagon, cortisol, vitamin D, thyroid hormone, retinoic acid, and growth hormones; growth factors such as VEGF, EGF, NGF, and PDGF; cholesterol; bile acids; neurotransmitters such as GABA, Glutamate, acetylcholine; NOGO; inositol triphosphate; diacylglycerol; epinephrine; norepinephrine; peptides, vitamins such as folate, pyridoxine, and biotin, drugs such as acetylsalicylic acid and naproxen, antibodies and any other molecule that can interact with a receptor in vivo or in vitro. The ligand can be attached to a compound of the invention using a linker molecule, such as an amide, carbonyl, ester, peptide, disulphide, silane, nucleoside, abasic nucleoside, polyether, polyamine, polyamide, carbohydrate, lipid, polyhydrocarbon, phosphate ester, phosphoramidate, thiophosphate, alkylphosphate, or photolabile linker. In one embodiment, the linker is a biodegradable linker. Conditions suitable for cleavage can include but are not limited to pH, UV irradiation, enzymatic activity, temperature, hydrolysis, elimination, and substitution reactions, and thermodynamic properties of the linkage.

The term "lipid" as used herein, refers to any lipophilic compound. Non-limiting examples of lipid compounds include fatty acids and their derivatives, including straight chain, branched chain, saturated and unsaturated fatty acids, carotenoids, terpenes, bile acids, and steroids, including cholesterol and derivatives or analogs thereof.

The term "lipid particle" or "lipid particle composition" refers to a composition comprising one or more biologically active molecules independently or in combination with a cationic lipid, a neutral lipid, and/or a polyethyleneglycol-diacylglycerol conjugate (i.e., polyethyleneglycol diacylglycerol (PEG-DAG), PEG-cholesterol, or PEG-DMB). A formulated molecular composition can further comprise cholesterol or a cholesterol derivative. The cationic lipid of the invention can comprise a compound having any of Formulae I-VI, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-Dioleoyl-3-Dimethylammonium-propane (DODAP), 1,2-

Dioleoylcarbamyl-3-Dimethylammonium-propane (DOCDAP), 1,2-Dilineoyl-3-Dimethylammonium-propane (DLINDAP), 3-Dimethylamino-2-(Cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLin DMA), N,N-Dimethyl-3,4-dioleyloxybenzylamine (DMOBA) and/or a mixture thereof. The neutral lipid can comprise dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof. The PEG conjugate can comprise a PEG-dilaurylglycerol (C12), a PEG-dimyristylglycerol (C14), a PEG-dipalmitoylglycerol (C16), a PEG-disterylglycerol (C18), PEG-dilaurylglycamide (C12), PEG-dimyristylglycamide (C14), PEG-dipalmitoylglycamide (C16), PEG-disterylglycamide (C18), PEG-cholesterol, or PEG-DMB. The cationic lipid component can comprise from about 2% to about 60%, from about 5% to about 45%, from about 5% to about 15%, or from about 40% to about 50% of the total lipid present in the formulation. The neutral lipid component can comprise from about 5% to about 90%, or from about 20% to about 85% of the total lipid present in the formulation. The PEG-DAG conjugate (e.g., polyethyleneglycol diacylglycerol (PEG-DAG), PEG-cholesterol, or PEG-DMB) can comprise from about 1% to about 20%, or from about 4% to about 15% of the total lipid present in the formulation. The cholesterol component can comprise from about 10% to about 60%, or from about 20% to about 45% of the total lipid present in the formulation. In one embodiment, a formulated molecular composition of the invention comprises a cationic lipid component comprising about 7.5% of the total lipid present in the formulation, a neutral lipid comprising about 82.5% of the total lipid present in the formulation, and a PEG conjugate comprising about 10% of the total lipid present in the formulation. In one embodiment, a formulated molecular composition of the invention comprises a biologically active molecule, DODMA, DSPC, and a PEG-DAG conjugate. In one embodiment, the PEG-DAG conjugate is PEG-dilaurylglycerol (C12), PEG-dimyristylglycerol (C14), PEG-dipalmitoylglycerol (C16), or PEG-disterylglycerol (C18). In another embodiment, the formulated molecular composition also comprises cholesterol or a cholesterol derivative.

By "nanoparticle" is meant a microscopic particle whose size is measured in nanometers. Nanoparticles of the invention typically range from about 1 to about 999 nm in diameter, and can include an encapsulated or enclosed biologically active molecule.

By "PEG" is meant, any polyethylene glycol or other polyalkylene ether or equivalent polymer.

The terms "short interfering nucleic acid", "siNA", "short interfering RNA", "siRNA", and "short interfering nucleic acid molecule" as used herein refer to any nucleic acid molecule capable of inhibiting or down regulating gene expression or viral replication by mediating RNA interference "RNAi" or gene silencing in a sequence-specific manner. For example the siNA can be a double-stranded nucleic acid molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof). Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell.,* 110, 563-574 and Schwarz et al., 2002, *Molecular Cell,* 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides. As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. Non limiting examples of siNA molecules of the invention are shown in U.S. Ser. No. 11/234,730, filed Sep. 23, 2005, incorporated by reference in its entirety herein. Such siNA molecules are distinct from other nucleic acid technologies known in the art that mediate inhibition of gene expression, such as ribozymes, antisense, triplex forming, aptamer, 2,5-A chimera, or decoy oligonucleotides.

By "target" as used herein is meant, any target protein, peptide, or polypeptide encoded by a target gene. The term "target" also refers to nucleic acid sequences encoding any target protein, peptide, or polypeptide having target activity, such as encoded by target RNA. The term "target" is also meant to include other target encoding sequence, such as other target isoforms, mutant target genes, splice variants of target genes, and target gene polymorphisms.

Pharmaceutical Compositions

The compounds of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. One or more compounds of the invention may be present in association with one or more non-toxic pharmaceutically acceptable carriers and/or diluents and/or adjuvants, and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oil phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, preservative and flavoring and coloring agent. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

General Procedure

Representative synthetic procedures for the preparation of compounds of the invention are outlined below in the following schemes. Those having skill in the art will recognize that the starting materials and reaction conditions may be varied, the sequence of the reactions altered, and additional steps employed to produce the desired compounds. In some cases, protection of certain reactive functionalities may be necessary to achieve some of the above transformations. In general, the need for such protecting groups as well as the conditions necessary to attach and remove such groups will be apparent to those skilled in the art of organic synthesis.

Unless otherwise indicated, $R_1$, $R_2$, X, X', G, $G_1$, $G_2$, T, $T_1$, $T_2$, n1, n2, n3, and n4 carry the definitions set forth above in connection with formulae I-VI. The variable LG represents a suitable leaving group including, but not limited to, halogen, toluenesulfonyl, methanesulfonyl, trifluoromethanesulfonyl, 2,2,2-trifluoroethoxy, N-hydroxysuccinimidyl, and the like.

-continued

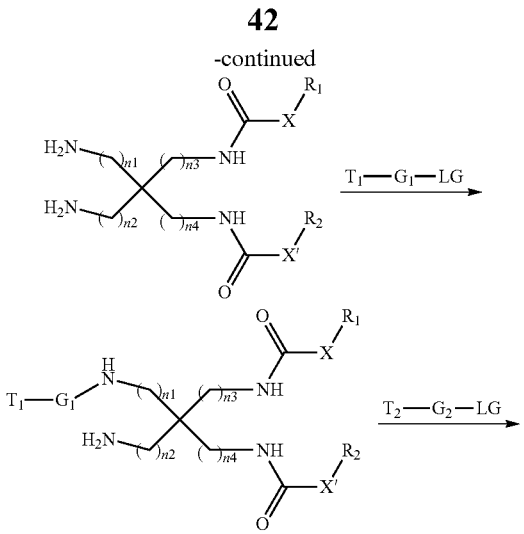

Scheme 1

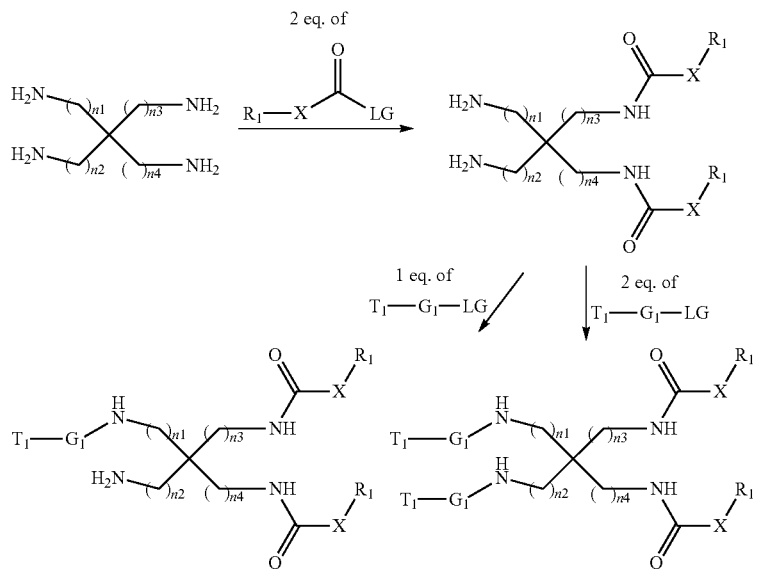

Scheme 2

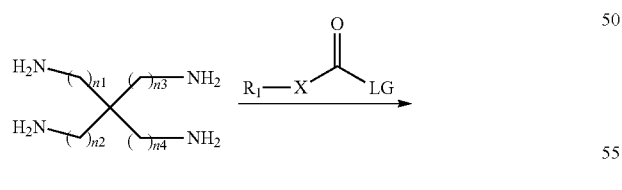

-continued

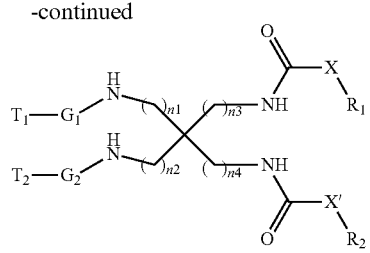

Scheme 3

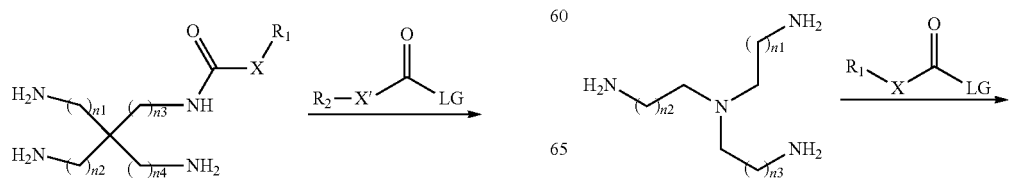

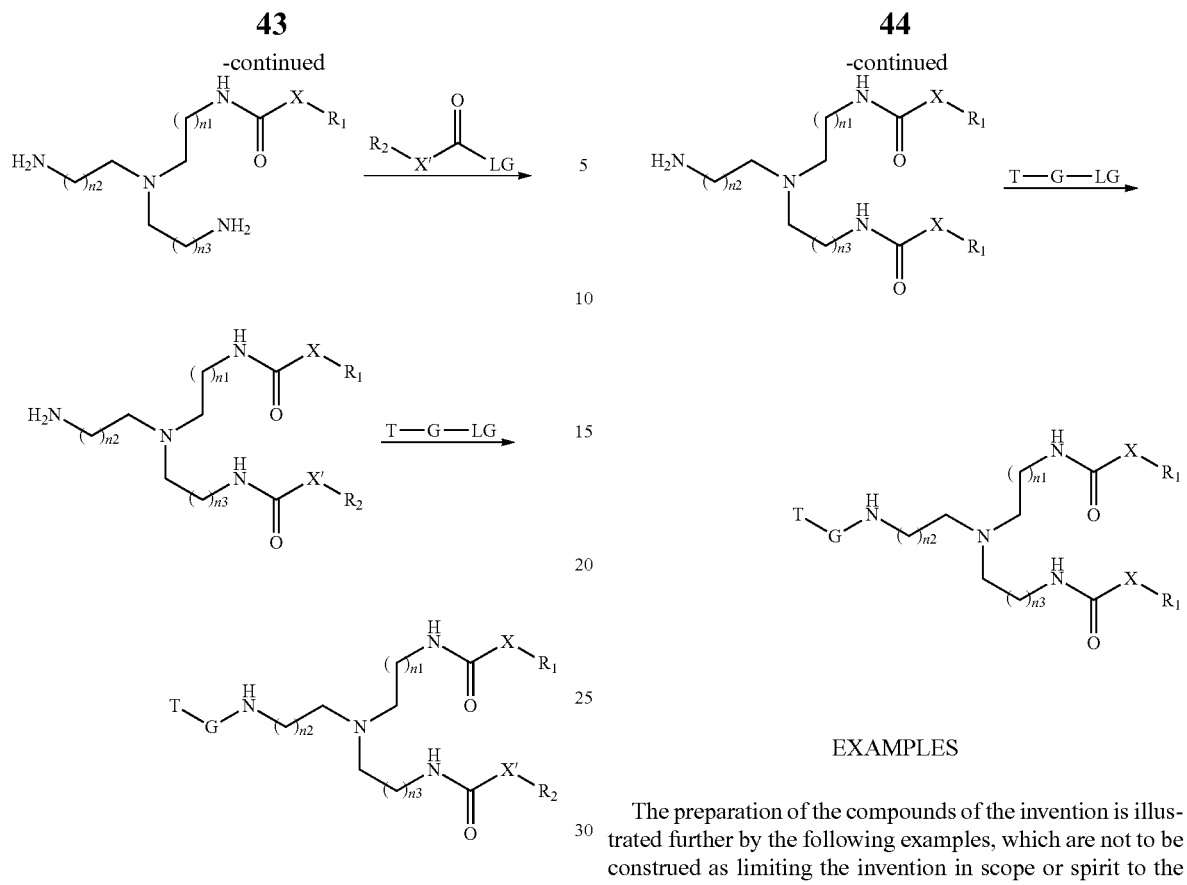

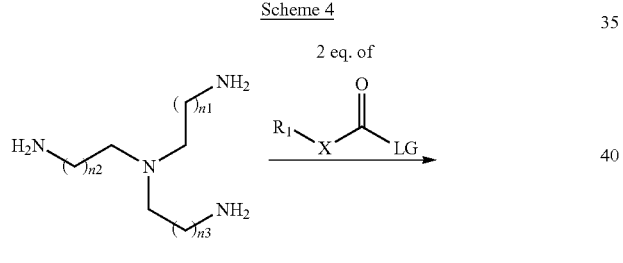

EXAMPLES

The preparation of the compounds of the invention is illustrated further by the following examples, which are not to be construed as limiting the invention in scope or spirit to the specific procedures and compounds described in them. Representative methods for synthesizing compounds of the invention are presented below. It is understood that the nature of the substituents required for the desired target compound often determines the preferred method of synthesis.

Example 1

Synthesis of N,N'-dioleoyl tetrakis(aminomethyl)methane ("dioleoyl crossamine")

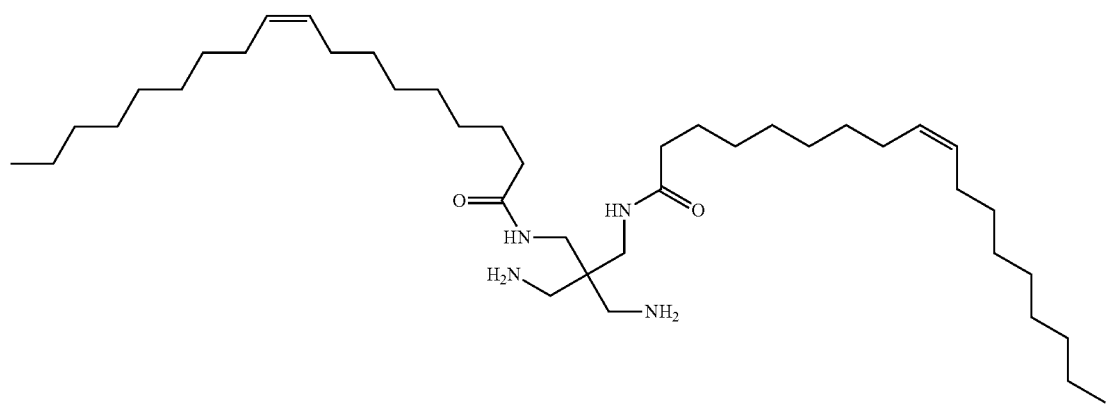

dioleoyl crossamine

Tetrakis(aminomethyl)methane is prepared by a known procedure (Adil, K. et al., Solid State Sciences, 6 (2004), 1229-1235). A 50 mL flask is equipped with a reflux condenser and a magnetic stirrer. The flask is charged with tetrakis(aminomethyl)methane tetrachloride (800 mg, 2.88 mmol), methanol (10 mL) and NaOMe/MeOH solution (2.10 g of 5.457M, 11.50 mmol). The mixture is stirred and refluxed for 4 hours, then cooled. Methanol solution is decanted from the inorganic salts, and the salts are re-suspended in absolute ethanol (15 mL). The suspension is centrifuged, and the combined organics are concentrated in vacuo. The residue is dissolved in methylene chloride (15 mL) and filtered using a syringe (0.45 micron filter) from the remaining inorganic salts. Concentration of the filtrates affords free tetrakis(aminomethyl)methane in a quantitative yield as a white semi-solid material (the residual alcohol is estimated by NMR). NMR (D$_2$O) δ 2.9 (s, CH$_2$)

The obtained tetrakis(aminomethyl)methane (420 mg, 90% purity, 2.86 mmol) is dissolved in absolute ethanol (15 mL) and trifluoroacetic acid (400 mg, 3.50 mmol) is added, followed by 2,2,2-trifluoroethyloleate (2.08 g, 5.72 mmol) [vide infra, Example 3]. The homogeneous mixture is allowed to react for 72 hrs at room temperature, and concentrated in vacuo. The residue is dissolved in MeOH/water (10%)/trifluoroacetic acid (0.1%) (40 mL), and pH is adjusted to ca. pH 2 with trifluoroacetic acid. The residue is purified by chromatography on C-8 modified silica, using MeOH/water (10%)/tri-fluoroacetic acid (0.1%) as eluent. N,N'-dioleoyl tetrakis(aminomethyl)methane ("dioleoyl crossamine") is Isolated as bistrifluoroacetic salt (0.9 g). MS (TFA salt) 661 [M+1]; NMR (CDCl$_3$) δ 8.5 (br. 6H), 8.05 (br, 2H), 5.37 (m, 4H), 3.07 and 2.95 (poorly resolved, 4H each); 2.15 (t, 4H), 2.01 (m, 8H), 1.35 (m, 48H), 0.9 (t, 6H)

Minor amounts of 2, 3, and 4 are produced when the reaction is carried under higher pH (e.g. without trifluoroacetic acid or in the presence of NaOMe), and those can be readily removed (e.g. chromatography):

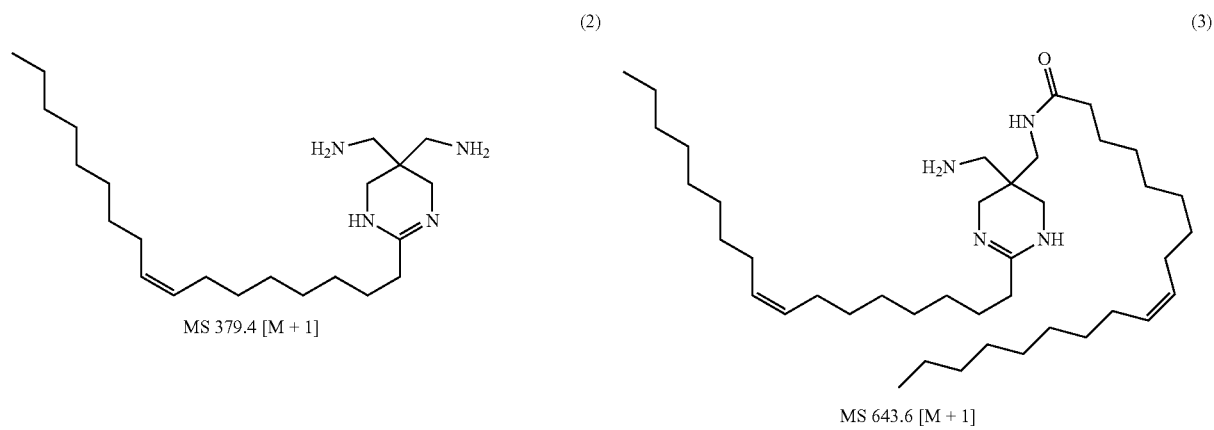

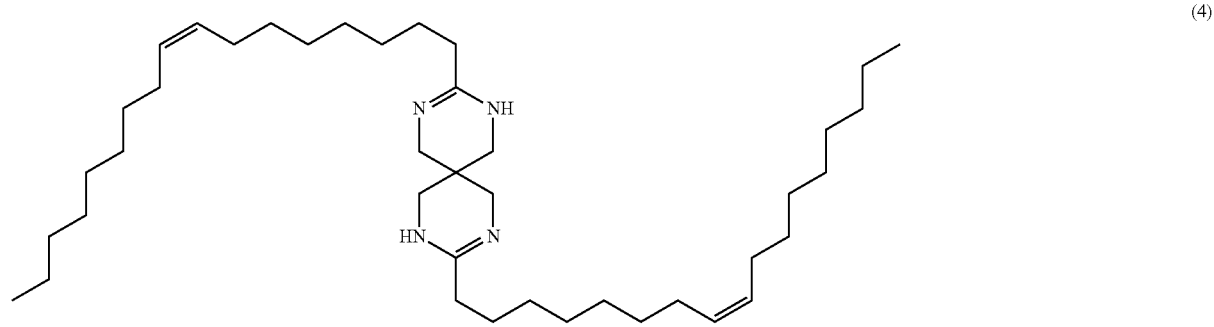

Example 2

2.1. Folate-PEG3400-COOH

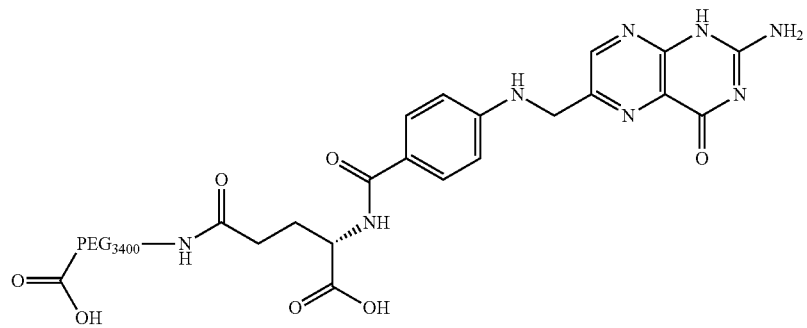

170 mg of H₂N-PEG3400-COOH (manufactured by Laysan) is dissolved in dry DMSO (2 mL) and dry chloroform (2 mL). Hunig's base (15 µL) is added, followed by addition of Folic acid-NHS ester (60 mg, prepared by a known procedure Lee, R. J.; Low, P. S.; "Methods in Molecular Medicine", 25, 69-76, April 2000). Additional 80 mg of Folic acid-NHS is added as a solution in DMSO (2.5 mL). The stirred mixture is kept at room temperature for 24 hrs; the chloroform is removed in vacuo, and the residue is diluted with deionized water (60 mL). The resulting homogeneous yellow solution is dialyzed against deionized water, with a few drops of TFA to pH 2-3, using 3500 D cutoff membrane. After six dialysis bath changes the yellow solution is collected and concentrated in vacuo to afford Folate-PEG3400-COOH.

2.2. Coupling with Folate-PEG3400-COOH to Obtain "folate-PEG-dioleoyl crossamine" (5)

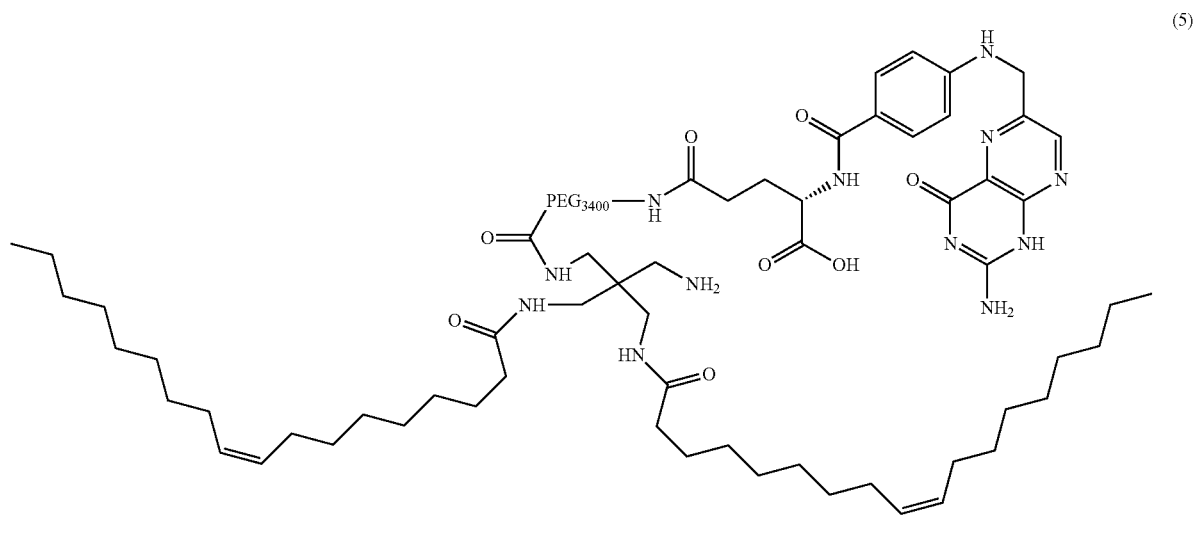

folate-PEG-dioleoyl crossamine 150 mg of Folate-PEG3400-COOH is dissolved in dry DMSO (2 mL) and NHS (9 mg) is added, followed by DCC (16 mg). The mixture is allowed to react in the dark for 20 hrs to obtain Folate-PEG3400-COONHS. To this solution, 30 mg of N,N'-dioleoyl tetrakis(aminomethyl)methane in dry DMSO (2 mL) is added. After the reaction mixture is reacted for 24 hrs, it is diluted with deionized water (60 mL). The resulting homogeneous yellow solution is dialyzed against deionized water using 3500 D cutoff bag, to afford Folate-PEG-ylated N,N'-dioleoyl tetrakis(aminomethyl)methane ("folate-PEG-dioleoyl crossamine") as ca. 50% mixture with unreacted Folate-PEG3400-COOH.

Example 3

Synthesis of N,N'-dioleoyl tris(aminoethyl)amine ("dioleoyl monoamine") (6)

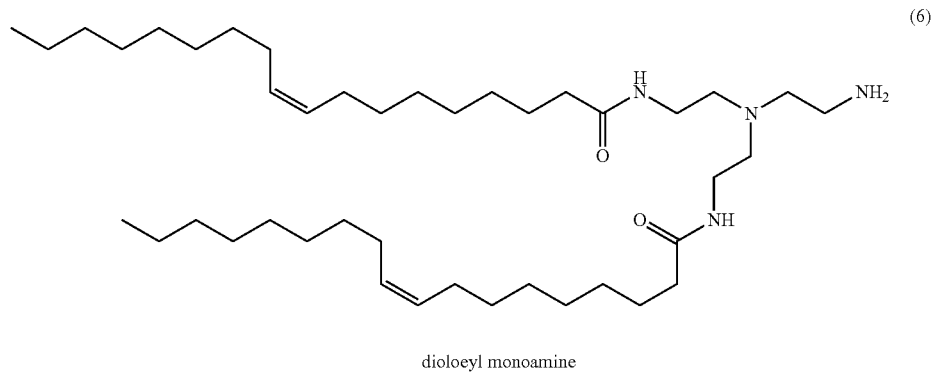 [SMILES: CCCCCCCC/C=C\CCCCCCCC(=O)NCCN(CCN)CCNC(=O)CCCCCCC/C=C\CCCCCCCC]

dioloeyl monoamine

Oleoyl chloride (75 g, 250 mmol) is heated at reflux with 2,2,2-trifluoroethanol (60 g, 600 mmol) for 16 hrs. After the evolution of HCl ceased, excess trifluoroethanol is removed in vacuo. Vacuum distillation of the residue afforded 87.6 g of 2,2,2-trifluoroethyl oleate as colorless liquid, by 150°/0.3.

Tris-(2-aminoethyl)amine (1.45 g, 10 mmol) is dissolved in 20 mL of ethanol. To this solution 2,2,2-trifluoroethyl oleate (5.6 g) is added, and the reaction mixture is refluxed for 24 hrs. The mixture is concentrated in vacuo, the residue is dissolved in 90% acetonitrile/10% water and acidified to pH 2-3 with trifluoroacetic acid (TFA). Reverse-phase chromatography of this solution on C8 silica (eluent 89.9% acetonitrile/10% water/0.1% TFA) affords 1.8 g of N,N'-dioleoyl tris(aminoethyl)amine ("dioleoyl monoamine") as its trifluoroacetic salt. MS (TFA salt) 675 [M+1]; NMR (CDCl$_3$) δ 7.4 (br, 2H), 5.37 (m, 4H), 3.55, 3.37 and 3.05 (poorly resolved, 12H total), 2.15 (t, 4H), 2.01 (m, 8H), 1.35 (m, 48H), 0.9 (t, 6H).

Example 3A

Preparation of Methyl-dioleoyl Monoamine (6.1)

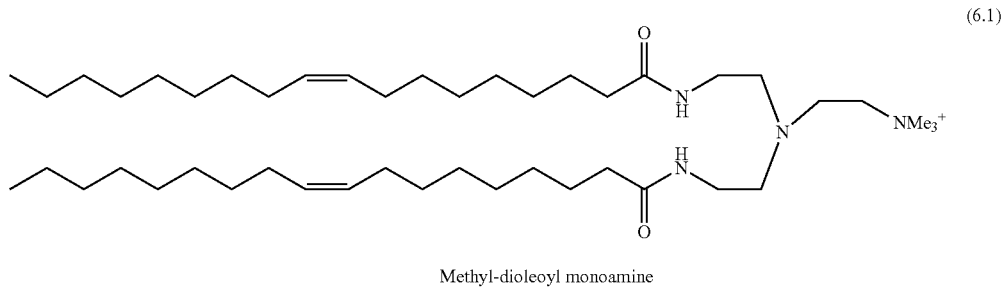

Methyl-dioleoyl monoamine

The title compound is prepared by methylation of the product of Example 3, N,N'-dioleoyl tris(aminoethyl)amine {"dioleoyl monoamine"), with an excess of iodomethane.

Example 4

Synthesis of N,N'-dioleoyl-N'''-acetylsalicyloyl tris(aminoethyl)amine (7)

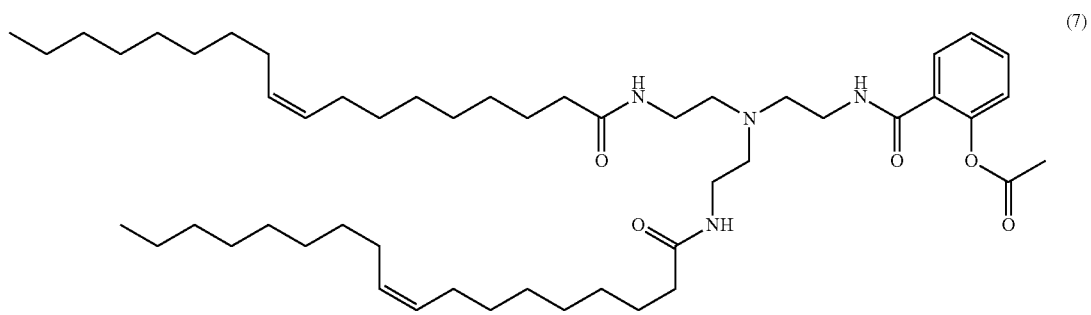 [SMILES: CCCCCCCC/C=C\CCCCCCCC(=O)NCCN(CCNC(=O)CCCCCCC/C=C\CCCCCCCC)CCNC(=O)c1ccccc1OC(C)=O]

N,N'-dioleoyl-tris(aminoethyl)amine trifluoroacetate (80 mg, 100 µmol) is dissolved in 5 mL chloroform and treated with 3 mL of 10% aq. K$_2$CO$_3$ solution. The organic phase is separated, dried and concentrated in vacuo to afford N,N'-dioleoyl-tris(aminoethyl)amine as the free base. This material is dissolved in 3 mL of dry chloroform and the solution is treated with acetylsalycyloylchloride (20 mg, 100 µmol) to afford the title compound.

Example 5

Coupling with Folate-PEG3400-COOH to Obtain "folate-PEG-dioleoyl monoamine" (8)

(8)

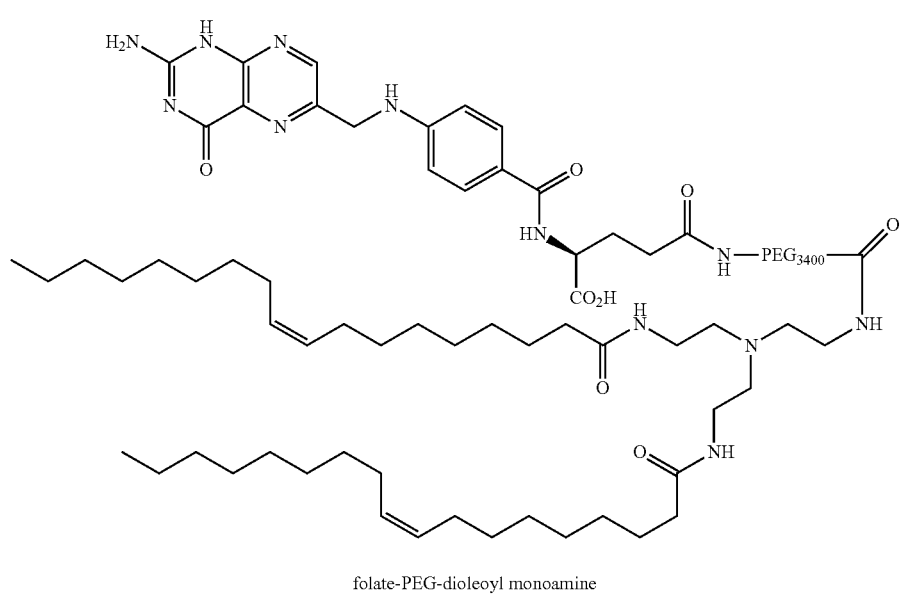

folate-PEG-dioleoyl monoamine

Folate-dioleoyl monoamine is obtained essentially as described in Example 2 from Folate-PEG3400-COOH and dioleyl monoamine.

Example 6

Complex of Dioleoyl Crossamine with siRNA; Formation of Nanoparticles

The siRNA used is a double stranded sequence of nucleotides intended to produce a knock-down of endogenous vascular endothelial growth factor (VEGF) transcripts and protein levels. The cationic lipid used is dioleoyl crossamine. siRNA (3 mg/mL) and dioleoyl crossamine (5 mg/mL) solutions are separately prepared in water for injection and subsequently diluted in 5% dextrose to 0.3 mg/mL for siRNA and 1.5 mg/mL for dioleoyl crossamine. The siRNA in dextrose solution is added to dioleoyl crossamine in dextrose solution using a micropipette to a charge ratio of 5:1 (positive:negative). The formulation is incubated for 15 minutes at room temperature to allow the complexes to form.

Example 7

Complex of Dioleoyl Crossamine with DNA; Formation of Nanoparticles

The nucleic acid used is a plasmid DNA encoding for luciferase gene. The cationic lipid used is dioleoyl crossamine. The plasmid DNA (3 mg/mL) and dioleoyl crossamine (5 mg/mL) solutions are separately prepared in water for injection, and subsequently diluted in 5% dextrose to 0.3 mg/mL for plasmid DNA and 1.5 mg/mL for dioleoyl crossamine. The plasmid DNA in dextrose solution is added to dioleoyl crossamine in dextrose solution using a micropipette to a charge ratio of 5:1 (positive:negative). The formulation is incubated for 15 minutes at room temperature to allow the complexes to form.

Example 8

Complex of Folate-PEG-Dioleoyl Crossamine with siRNA

The siRNA used is a double stranded sequence of nucleotides intended to produce a knock-down of endogenous vascular endothelial growth factor (VEGF) transcripts and protein levels. The cationic lipid used is dioleoyl crossamine conjugated to folate ligands or co-formulated with folated dioleoyl crossamine at different molar ratios (1:1), (2:1), (4:1), or (10:1). The co-formulant is added to dioleoyl crossamine chloroform solution, and liposome preparation is performed as described in Example 9. The siRNA (3 mg/mL) and folate-PEG-dioleoyl crossamine (5 mg/mL) solutions are separately prepared in water for injection and subsequently diluted in 5% dextrose to 0.3 mg/mL for siRNA and 1.9 mg/mL for folate-PEG-dioleoyl crossamine. The siRNA in dextrose solution is added to folate-PEG-dioleoyl crossamine in dextrose solution using a micropipette to a charge ratio of 5:1 (positive:negative). The formulation is incubated for 15 minutes at room temperature to allow the complexes to form.

Example 9

Complex of Dioleoyl Monoamine and siRNA; Formation of Nanoparticles

The siRNA used is a double stranded sequence of nucleotides intended to produce a knock-down of endogenous vascular endothelial growth factor (VEGF) transcripts and protein levels. The cationic lipid used is dioleoyl monoamine. siRNA (3 mg/mL) and dioleoyl monoamine (5 mg/mL) solutions are separately prepared in water for injection, and subsequently diluted in 5% dextrose to 0.3 mg/mL for siRNA and 1.5 mg/mL for dioleoyl monoamine. The siRNA in dextrose solution is added to the dioleoyl monoamine in dextrose solution using a micropipette to a charge ratio of 5:1 (positive: negative). The formulation is incubated for 15 minutes at room temperature to allow the complexes to form.

Example 10

Complex of Dioleoyl Monoamine and DNA; Formation of Nanoparticles

The nucleic acid used is a plasmid DNA encoding for luciferase gene and the cationic lipid used is dioleoyl monoamine. The plasmid DNA (3 mg/mL) and dioleoyl monoamine (5 mg/mL) solutions are separately prepared in water for injection, and subsequently diluted in 5% dextrose to 0.3 mg/mL for the plasmid DNA and 1.5 mg/mL for dioleoyl monoamine. The plasmid DNA in dextrose solution is added to the dioleoyl monoamine in dextrose solution using a micropipette to a charge ratio of 5:1 (positive:negative). The formulation is incubated for 15 minutes at room temperature to allow the complexes to form.

Example 11

Preparation of Encapsulated siRNA with Dioleoyl Crossamine

This example illustrates liposomal encapsulation of siRNA using dioleoyl crossamine. The siRNA used is a double stranded sequence of nucleotides intended to produce a knock-down of endogenous vascular endothelial growth factor (VEGF) transcripts and protein levels. The cationic lipid used is dioleoyl crossamine. To prepare the capsulation liposomes, the lipids are dissolved and mixed in chloroform to assure a homogeneous mixture of lipids. The organic solvent is removed by rotary evaporation yielding a thin lipid film on the sides of a round flask. Chloroform is further evaporated by placing the round flask on a vacuum pump overnight. The resulting lipid film is dissolved initially in 100% ethanol then brought to 50%. siRNA dissolved in water is added to liposomes/ethanol solution. Ethanol is evaporated from the liposomes/siRNA mixture by a rotary evaporation system. The resulting nanoparticles are suspended in 5% dextrose by adding and equal amount of 10% dextrose to the encapsulated siRNA particles.

Example 12

Preparation of Encapsulated siRNA with Folate-PEG-Dioleoyl Crossamine

This example illustrates liposomal encapsulation of siRNA using folate-PEG-dioleoyl crossamine. The siRNA used is a double stranded sequence of nucleotides intended to produce a knock-down of endogenous vascular endothelial growth factor (VEGF) transcripts and protein levels. The cationic lipid used is folate-PEG-dioleoyl crossamine. To prepare the capsulation liposomes, the lipids are dissolved and mixed in chloroform to assure a homogeneous mixture of lipids. The organic solvent is removed by rotary evaporation yielding a thin lipid film on the sides of a round flask. Chloroform is further evaporated by placing the round flask on a vacuum pump overnight. The resulting lipid film is dissolved initially in 100% ethanol then brought to 50%. siRNA dissolved in water is added to liposomes/ethanol solution. Ethanol is evaporated from the liposomes/siRNA mixture by a rotary evaporation system. The resulting nanoparticles are suspended in 5% dextrose by adding and equal amount of 10% dextrose to the encapsulated siRNA particles.

Example 13

Preparation of siRNA Transfection Complexes with Dioleoyl Monoamine with Co-Formulants The siRNA used is a double stranded sequence of nucleotides intended to produce a knock-down of endogenous vascular endothelial growth factor (VEGF) transcripts and protein levels. The dioleoyl monoamine is formulated with other lipids at a molar ratio of (4:1). The lipids used are 1,2-Dioleoyl-sn-Glycero-3-Phosphoethanolamine (DOPE), 1,2-distearoyl-sn-glycero-3-phosphoethanolamine-N-[methoxy(polyethylene glycol)-550], 1,2-Dioleoyl-sn-Glycero-3-Phosphoethanolamine-N-Lactosyl, and Cholesterol. The co-formulants are added to dioleoyl monoamine in chloroform. Liposomes are prepared as previously described in Example 9. The siRNA (3 mg/mL) and dioleoyl monoamine (5 mg/mL) solutions are separately prepared in water for injection, and subsequently diluted in 5% dextrose to 0.3 mg/mL for siRNA and 1.9 mg/mL for dioleoyl monoamine. The siRNA in dextrose solution is added to the dioleoyl monoamine in dextrose solution using a micropipette to a charge ratio of 5:1 (positive negative). The formulation is incubated for 15 minutes at room temperature to allow the complexes to form.

Example 14

Preparation of DNA Transfection Complexes with Dioleoyl Monoamine

The nucleic acid used is a plasmid DNA encoding for luciferase gene and the dioleoyl monoamine lipid. The plasmid DNA (3 mg/mL) and dioleoyl monoamine (5 mg/mL) solutions are separately prepared in water for injection and subsequently diluted in 5% dextrose to 0.3 mg/mL for plasmid DNA and 1.9 mg/mL for dioleoyl monoamine. The plasmid DNA in dextrose solution is added to the dioleoyl monoamine in dextrose solution using a micropipette to a charge ratio of 5:1 (positive:negative). The formulation is incubated for 15 minutes at room temperature to allow the complexes to form.

Example 15

Preparation of DNA Transfection Complexes with Dioleoyl Monoamine with Co-Formulants The nucleic acid used is a plasmid DNA encoding for luciferase gene and the cationic lipid used is dioleoyl monoamine. The cationic lipid used in this example is dioleoyl monoamine formulated with other lipids at a molar ratio of (4:1). The lipids used are 1,2-Dioleoyl-sn-Glycero-3-Phosphoethanolamine (DOPE), 1,2-distearoyl-sn-glycero-3-phosphoethanolamine-N-[methoxy(polyethylene glycol)-550], 1,2-Dioleoyl-sn-Glycero-3-Phosphoethanolamine-N-Lactosyl, and Cholesterol. The co-formulants are added to dioleoyl monoamine chloroform solution. Liposomes are prepared as previously described in Example 9. The DNA (3 mg/mL) and dioleoyl monoamine co-formulants (5 mg/mL) solutions are separately prepared in water for injection, and subsequently diluted in 5% dextrose to 0.3 mg/mL for DNA and 1.9 mg/mL for dioleoyl monoamine. The DNA in dextrose solution is added to the dioleoyl monoamine in dextrose solution using a micropipette to a charge ratio of 5:1 (positive: negative). The formulation is incubated for 15 minutes at room temperature to allow the complexes to form.

Example 16

Preparation of siRNA Transfection Complexes with Dioleoyl Monoamine Co-Formulated with Folate-PEG-Dioleoyl Monoamine The siRNA used is a double stranded sequence of nucleotides intended to produce a knock-down of endogenous vascular endothelial growth factor (VEGF) transcripts and protein levels. The cationic lipid used is dioleoyl monoamine co-formulated with folate-PEG-dioleoyl monoamine at different molar ratios (1:1), (2:1), (4:1), or (10:1). The co-formulant is added to dioleoyl monoamine chloroform solution. Liposomes are prepared as previously described in Example 9. The siRNA (3 mg/mL) and dioleoyl monoamine/folate-PEG-dioleoyl monoamine (5 mg/mL) solutions are separately prepared in water for injection, and subsequently diluted in 5% dextrose to 0.3 mg/mL for siRNA and 1.9 mg/mL for dioleoyl monoamine. The siRNA in dextrose solution is added to the dioleoyl monoamine in dextrose solution using a micropipette to a charge ratio of 5:1 (positive:negative). The formulation is incubated for 15 minutes at room temperature to allow the complexes to form.

Example 17

Preparation of Encapsulated siRNA with Dioleoyl Monoamine Liposomes

The siRNA used is a double stranded sequence of nucleotides intended to produce a knock-down of endogenous vascular endothelial growth factor (VEGF) transcripts and protein levels. The cationic lipid used is dioleoyl monoamine. To prepare the capsulation liposomes, the lipids are dissolved and mixed in chloroform to assure a homogeneous mixture of lipids. The organic solvent is removed by rotary evaporation yielding a thin lipid film on the sides of a round flask. Chloroform is further evaporated by placing the round flask on a vacuum pump overnight. The resulting lipid film is dissolved initially in 100% ethanol then brought to 50%. siRNA dissolved in water is added to liposomes/ethanol solution. Ethanol is evaporated from the liposomes/siRNA mixture by a rotary evaporation system. The resulting nanoparticles are suspended in 5% dextrose by adding and equal amount of 10% dextrose to the encapsulated siRNA particles.

Example 18

Preparation of Encapsulated siRNA with Folate-PEG-Dioleoyl Monoamine Liposomes

The siRNA used is a double stranded sequence of nucleotides intended to produce a knock-down of endogenous vascular endothelial growth factor (VEGF) transcripts and protein levels. The cationic lipid used is folate-PEG-dioleoyl monoamine. To prepare the capsulation liposomes, the lipids are dissolved and mixed in chloroform to assure a homogeneous mixture of lipids. The organic solvent is removed by rotary evaporation yielding a thin lipid film on the sides of a round flask. Chloroform is further evaporated by placing the round flask on a vacuum pump overnight. The resulting lipid film is dissolved initially in 100% ethanol then brought to 50%. siRNA dissolved in water is added to liposomes/ethanol solution. Ethanol is evaporated from the liposomes/siRNA mix by a rotary evaporation system. The resulting nanoparticles are suspended in 5% dextrose by adding and equal amount of 10% dextrose to the encapsulated siRNA particles.

Example 19

Transfection Activity of siRNA and Dioleoyl Crossamine Complexes

The transfection activity of siRNA and dioleoyl crossamine complexes is determined in vitro as follows. Transfection complexes containing mVEGF or luciferase siRNA constructs are prepared by methods described in Example 9. SCCVII cells ($0.5 \times 10^5$ cells/well; murine squamous cell carcinomas) are seeded into 24-well tissue culture plates in 10% fetal bovine serum (FBS). Each well is incubated for 6 hours with 0.5 µg of complexed siRNA in absence or presence of FBS in a total volume of 250 µL of Dulbecco Modified Eagle's Minimal Essential Medium (DMEM). When the incubation period is concluded for the cells lacking FBS in their medium, 250 µL of DMEM supplemented with 20% FBS is added to the transfected cells and incubated further for another 40 hours. To cells with FBS in their transfection medium, 250 µL of DMEM supplemented with 10% FBS is added to the transfected cells and incubated further for another 40 hours. At the end of the incubation period, knock down of mVEGF protein and transcripts are evaluated in the cell culture medium (protein) or cell lysate (transcripts). For measurement of mVEGF protein levels, cell culture medium is directly analyzed by mVEGF ELISA assay. For mVEGF transcripts analysis, cells are lysed using Tri-reagent and then quantified for the level of mVEGF transcripts using qRT-PCR detection kit.

Example 20

Transfection Activity of Encapsulated siRNA with Dioleoyl Crossamine

This example illustrates liposomal encapsulation of siRNA using dioleoyl monoamine, dioleoyl crossamine, or a mixture of both cationic agents. The siRNA used is a double stranded sequence of nucleotides intended to produce a knock-down of endogenous vascular endothelial growth factor (VEGF) transcripts and protein levels. The cationic lipids used are dioleoyl monoamine (Example 3), dioleoyl crossamine (Example 1), or a mixture of both. To prepare the capsulation liposomes, the lipids are dissolved and mixed in chloroform to assure a homogeneous mixture of lipids. The organic solvent is removed by rotary evaporation yielding a thin lipid film on the sides of a round flask. Chloroform is further evaporated by placing the round flask on a vacuum pump overnight. The resulting lipid film is dissolved initially in 100% ethanol then brought to 50%. siRNA dissolved in water is added to liposomes in ethanol solution. Ethanol is evaporated from the liposomes/siRNA mixture by a rotary evaporation system. The resulting nanoparticles are suspended in 5% dextrose by adding and equal amount of 10% dextrose to the encapsulated siRNA particles. SCCVII cells ($0.5 \times 10^5$ cells/well) are seeded into 24-well tissue culture plates in 10% FBS. Each well is incubated for 6 hours with 0.5 µg of complexed siRNA in absence or presence of FBS in a total volume of 250 µL of DMEM. When the incubation period is concluded for the cells lacking FBS in their medium, 250 μL of DMEM supplemented with 20% FBS is added to the transfected cells and incubated further for another 40 hours. To cells with FBS in their transfection medium, 250 μL of DMEM supplemented with 10% FBS is added to the transfected cells and incubated further for another 40 hours. At the end of the incubation period, knock down of mVEGF protein and transcripts are evaluated is measured in the cell culture medium (protein) or cell lysate (transcripts). For measurement of mVEGF protein levels, cell culture medium is directly analyzed by mVEGF ELISA assay. For mVEGF transcripts analysis, cells are lysed using Tri-reagent and then quantified for the level of mVEGF transcripts using qRT-PCR detection kit.

Example 21

Transfection Activity of Encapsulated siRNA with Folate-PEG-dioleoyl Crossamine

This example illustrates liposomal encapsulation of siRNA using folate-PEG-dioleoyl monoamine, folate-PEG-dioleoyl crossamine, or a mixture of both cationic agents. The siRNA used is a double stranded sequence of nucleotides intended to produce a knock-down of endogenous vascular endothelial growth factor (VEGF) transcripts and protein levels. The cationic lipids used are folate-PEG-dioleoyl monoamine (Example 5), folate-PEG-dioleoyl crossamine liposomes (Example 2), or mixture of both. To prepare the capsulation liposomes, the lipids are dissolved and mixed in chloroform to assure a homogeneous mixture of lipids. The organic solvent is removed by rotary evaporation yielding a thin lipid film on the sides of a round flask. Chloroform is further evaporated by placing the round flask on a vacuum pump overnight. The resulting lipid film is dissolved initially in 100% ethanol then brought to 50%. siRNA dissolved in water is added to liposomes in ethanol solution. Ethanol is evaporated from the liposomes/siRNA mixture by a rotary evaporation system. The resulting nanoparticles are suspended in 5% dextrose by adding and equal amount of 10% dextrose to the encapsulated siRNA particles. SCCVII cells ($0.5 \times 10^5$ cells/well) are seeded into 24-well tissue culture plates in 10% FBS. Each well is incubated for 6 hours with 0.5 μg of complexed siRNA in absence or presence of FBS in a total volume of 250 μL of DMEM. When the incubation period is concluded for the cells lacking FBS in their medium, 250 μL of DMEM supplemented with 20% FBS is added to the transfected cells and incubated further for another 40 hours. To cells with FBS in their transfection medium, 250 μL of DMEM supplemented with 10% FBS is added to the transfected cells and incubated further for another 40 hours. At the end of the incubation period, knock down of mVEGF protein and transcripts are evaluated is measured in the cell culture medium (protein) or cell lysate (transcripts). For measurement of mVEGF protein levels, cell culture medium is directly analyzed by mVEGF ELISA assay. For mVEGF transcripts analysis, cells are firstly, lysed using Tri-reagent and then quantified for the level of mVEGF transcripts using qRT-PCR detection Example 22

Uterine VEGF Protein Knockdown Following Intravaginal Administration of Dioleoyl Monoamine Complexed siRNA Two days preceding siRNA administration female ICR mice (17-22 grams) are given two daily sub-cutaneous administrations of progesterone (0.5 mg dissolved in sesame oil) to normalize estrus cycling in the animals. Mice are then intravaginally administered formulated siRNA targeting VEGF transcript or a non-targeting siRNA control. siRNA is complexed with dioleoyl monoamine at a 5:1 N:P charge ratio. A total of 9 μg siRNA is administered in a final volume of 30 μl (0.3 mg/mL). At 48 hours after administration, the animals are euthanized and the vagina/cervix and uterus (including uterine horns) are collected dissected free of other tissue and stored frozen in liquid $N_2$. Only tissues from animals that had a gross appearance consistent with progesterone treatment are used for analysis. Tissue is homogenized in lysis buffer and VEGF proteins determinations made by ELISA.

Example 23

Protein and Transcript Knockdown of Growth Factor in Ascites and Intraperitonel Tumor Nodules in Animals with Disseminated Peritoneal Malignancies Following Administration of Crossamine siRNA Formulations containing siRNA and dioleoyl crossamine are administered to animals with disseminated ovarian cancer in an effort to decrease VEGF levels that have been associated with disease progression. To induce disseminated ovarian cancer, female C57BL/6 mice are implanted IP with $2.5 \times 10^6$ ID8 (murine ovarian carcinoma) cells. At a predetermined day after tumor implant mice are injected with 200 μg siVEGF (or non-coding control siRNA) formulated with dioleoyl crossamine at an N:P ratio of 5:1. Starting at 24 hours after treatment animals are euthanized, tumor and ascites fluid are harvested from the peritoneal cavity and analyzed for VEGF protein and transcript levels. For ascites transcript analysis, samples are initially subjected to a red blood cell lysis protocol and enriched for nucleated cells prior to RNA isolation.

Example 24

Tumor Targeted siRNA Using Folate-PEG-Dioleoyl Crossamine

VEGF siRNA formulated with folate-PEG-dioleoyl crossamine is delivered intravenously or intraperitoneally into mice bearing subcutaneous SCCVII tumors. At specified time points after administration tumors are harvested and transcript and protein determination of the targeted transcript is determined.

Example 25

Enhanced Systemic Uptake of siRNA Using Peptide Modified Dioleoyl Crossamine siRNA is formulated with dioleoyl crossamine that has been functionally modified to target integrin receptor by the addition of a peptide having a conserved Arg-Gly-Asp motif. The complex is delivered intravenously or intraperitoneally to tumor bearing animals. At specified time points after administration various tissues are harvested and transcript and protein determination of the targeted transcript/protein is determined.

Example 26

Protein Knock-Down Following In Vitro Transfection of Complexed siRNA with Dioleoyl Monoamine Delivery Reagent The transfection activity of siRNA and dioleoyl monoamine delivery reagent conjugate complexes is determined in vitro. Transfection complexes containing simVEGF siRNA construct are prepared by methods previously described in Example 9. SCCVII cells ($0.5\times10^5$ cells/well) are seeded into 24-well tissue culture plates in 10% FBS. Each well is incubated for 6 hours with 0.5 μg of complexed siRNA in a total volume of 250 μL of DMEM. When the incubation period is concluded, 250 μL of DMEM supplemented with 20% FBS is added to the transfected cells and incubated further for another 40 hours. At the end of the incubation period, supernatant mVEGF protein determinations are made. The results indicate a significant (~95%) knockdown of VEGF protein (FIG. 1).

Example 27

Figure 2:
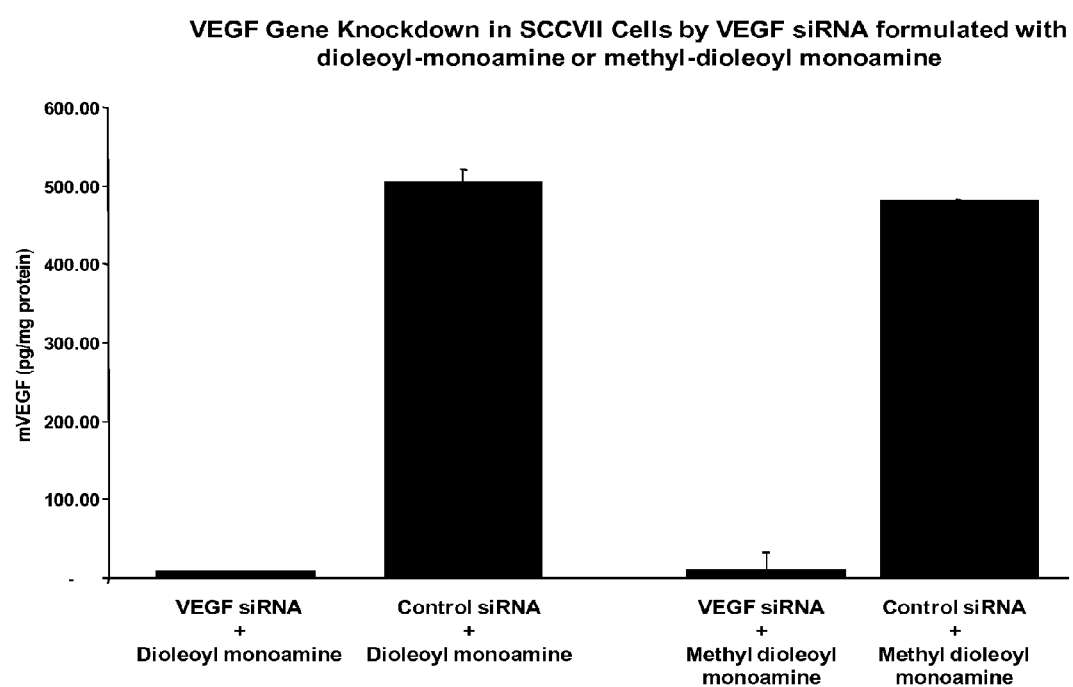
FIG. 2 is a graph showing protein expression levels of VEGF in cell culture medium following an in vitro transfection using murine squamous cell carcinoma VII (SCCVII) cells. Cells were transfected with siRNA formulated with dioleoyl monoamine or methyl-dioleoyl monoamine.

Protein Knock-Down Following In Vitro Transfection of Complexed siRNA with Dioleoyl Monoamine and Methyl-Dioleoyl Monoamine Delivery Reagents The transfection activity of siRNA complexes with dioleoyl monoamine (Example 3) or methyl-dioleoyl monoamine (Example 3A) delivery reagents is determined in vitro. Transfection complexes containing simVEGF siRNA construct are prepared by methods previously described. SCCVII cells ($0.5\times10^5$ cells/well) are seeded into 24-well tissue culture plates in 10% FBS. Each well is incubated for 6 hours with 0.5 μg of complexed siRNA in a total volume of 250 μL of DMEM. When the incubation period is concluded, 250 μL of DMEM supplemented with 20% FBS is added to the transfected cells and incubated further for another 40 hours. At the end of the incubation period, supernatant mVEGF protein determinations are made as described above. The results indicate a significant (~95%) knockdown of VEGF protein (FIG. 2).

Example 28

Protein and Transcripts Knock-Down Following In Vitro Transfection of Complexed siRNA with Folate-PEG-Dioleoyl Monoamine The transfection activity of siRNA and folate-PEG-dioleoyl monoamine conjugate complexes is determined in vitro. Transfection complexes containing simVEGF siRNA construct are prepared by methods previously described. SCCVII cells ($0.5\times10^5$ cells/well) are seeded into 24-well tissue culture plates in 10% FBS. Each well is incubated for 6 hours with 0.5 μg of complexed siRNA in absence or presence of folate substrate at variable concentrations in a total volume of 250 μL of DMEM. When the incubation period is concluded, 250 μL of DMEM supplemented with 20% FBS is added to the transfected cells and incubated further for another 40 hours. At the end of the incubation period, mVEGF protein and mVEGF transcripts levels are measured from the cell culture medium and cell lysates respectively. For measurement of mVEGF protein levels, cell culture medium is directly analyzed by mVEGF ELISA assay. For mVEGF transcripts analysis, cells are lysed using Tri-reagent and then quantified for the level of mVEGF transcripts using qRT-PCR detection kit. The percentage of VEGF protein and transcript knockdown that occurs relative to cells that have been transfected with non silencing control siRNA is calculated.

Example 29

Figure 3:
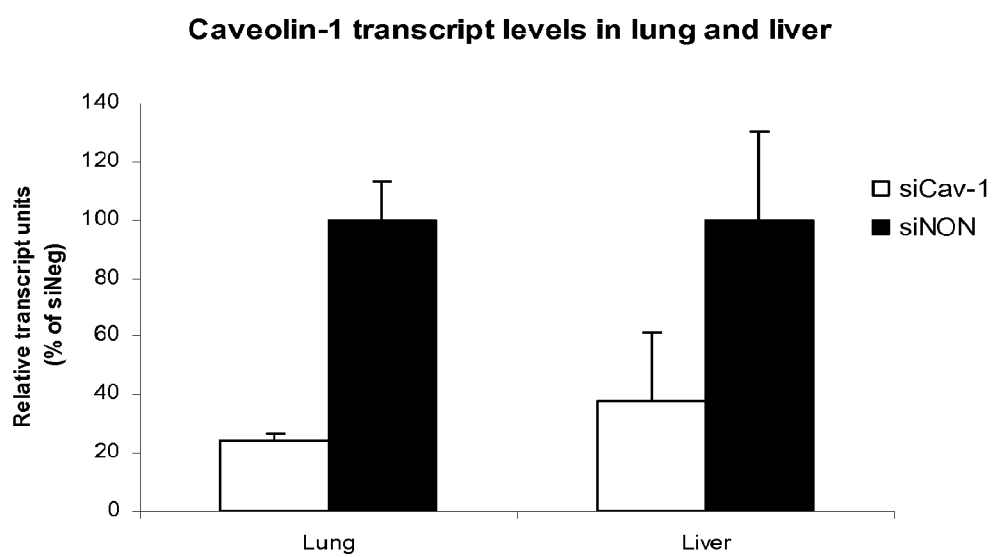
FIG. 3 is a graph showing siRNA specific transcript knockdown (Caveolin-1) in the lung and livers of mice following a single iv injection of siRNA formulated with dioleoyl monoamine.

Caveolin-1 Transcript Knockdown in Lung and Liver Following Administration of siRNA Complexed with Dioleoyl Monoamine Delivery Reagent Female ICR mice (17-22 grams) are injected intravenously with formulated siRNA targeting Caveolin-1 (Cav-1) transcript or a non-targeting siRNA control. siRNA is complexed with dioleoyl monoamine delivery reagent at a 10:1 ratio. A total of 100 μg siRNA is injected in a final volume of 200 μL (0.5 mg/mL). At 48 hours after injection the animals are euthanized and lungs and livers are harvested for Cav-1 transcript analysis using qRTPCR. Transcript levels are normalized to β-actin as an internal control. Results (FIG. 3) indicate a significant decrease in target specific Cav-1 transcript levels in both lungs (76% knockdown) and livers (62% knockdown). For each group, n=5.

Example 30

Figure 4A:
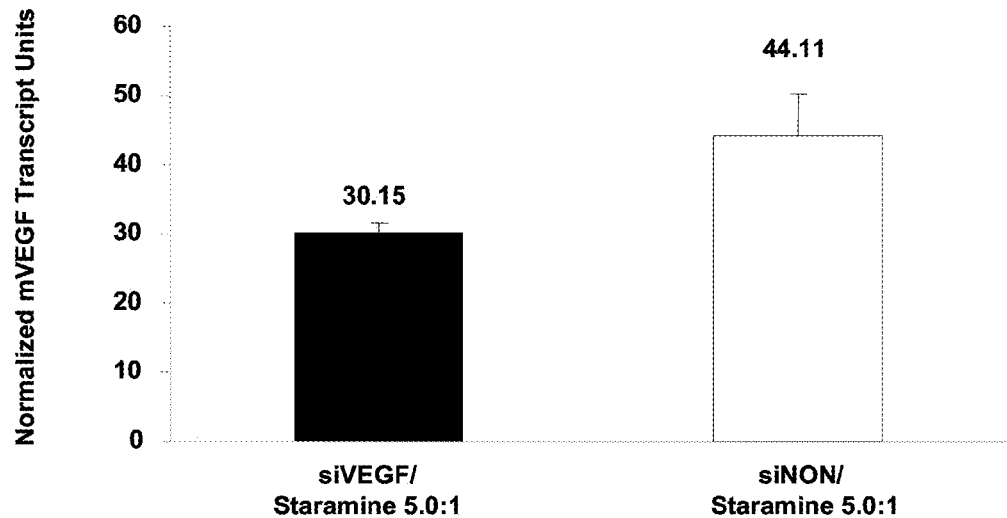
FIG. 4A and FIG. 4B are graphs showing mVEGF transcript levels in SCCVII tumors following IT injection of dioleoyl monoamine formulated VEGF siRNA (FIG. 4A) and inhibition of tumor growth (FIG. 4B) in mice following intratumoral administration of formulated VEGF siRNA.
Figure 4B:
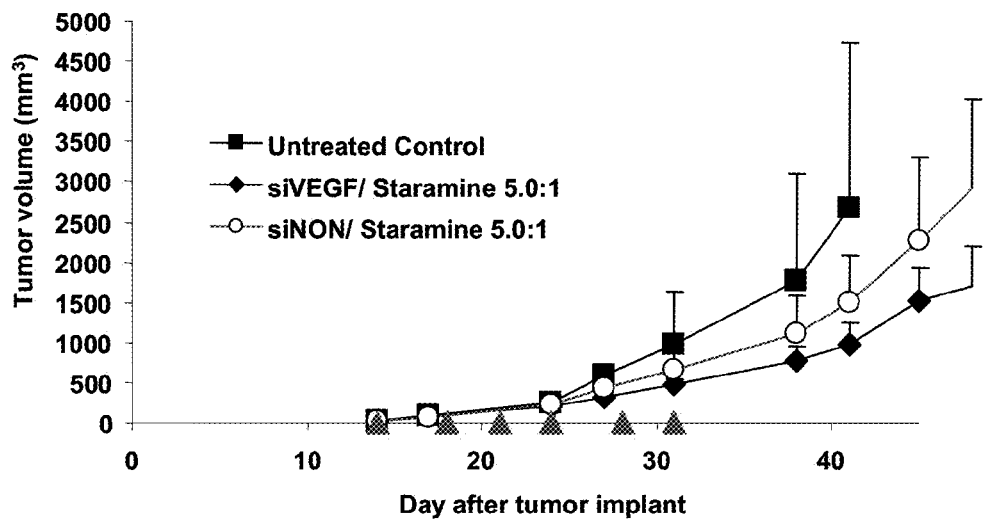

VEGF Transcript Knockdown Resulting in Tumor Inhibition Following Dioleoyl Monoamine Formulated siVEGF Injected into Subcutaneous Tumors in Mice In this example tumors were implanted into the hind flanks of CH3 mice by injecting $5\times10^5$ squamous cell carcinoma cells. Tumors were allowed to grow until they reached a size of ~40 mm$^3$. Tumors were then injected with a commercially available siRNA targeting VEGF that was formulated with dioleoyl monoamine at a 5:1 N:P ratio or with a similarly formulated non-silencing control siRNA. The final concentration of siRNA was 0.3 mg/mL. A total of 30 μl of the formulated siRNA solution was injected into tumors and injections were repeated every 3-4 days for a total of 6 injections. The tumors from some animals were harvested 48 hours after the second formulated siRNA injection for transcript analysis. Results from this study (FIG. 4) indicate that administration of the VEGF siRNA resulted in a 32% decrease in VEGF transcript relative to the non-silencing control group. One week following the last tumor injection there was a 31% decrease in tumor volume in the VEGF siRNA group relative to non-silencing siRNA and a 57% decrease relative to untreated control animals. The VEGF siRNA treatments further resulted in a 13% improvement in median survival of animals relative to either the non-silencing control (siNON) or untreated groups.

Example 31

Preparation of Concentrated siRNA Transfection Complexes with Dioleoyl Monoamine by Filtration The siRNA used is a double stranded sequence of nucleotides intended to produce a knock-down of endogenous vascular endothelial growth factor (VEGF) transcripts and protein levels. Liposomes of the cationic lipids are prepared as previously described in Example 9. The siRNA (20 mg/mL) and dioleoyl monoamine (6.4 mg/mL) solutions are separately prepared in water for injection. 25 µL of the siRNA is combined with 500 µL of dioleoyl monoamine solution. Subsequently, the complex is diluted in 5% dextrose to 0.03 mg/mL of siRNA. Diluted complex is transferred into 25-50 kDa centrifugal filter unit and centrifuged for several minutes to reach the desired siRNA concentration in the retentate.

Example 32

Preparation of Concentrated siRNA Transfection Complexes with Dioleoyl Crossamine by Filtration The siRNA used is a double stranded sequence of nucleotides intended to produce a knock-down of endogenous vascular endothelial growth factor (VEGF) transcripts and protein levels. Liposomes of the cationic lipids are prepared as previously described in Example 9. The siRNA (20 mg/mL) and dioleoyl crossamine (5 mg/mL) solutions are separately prepared in water for injection. 25 µL of the siRNA is combined with 500 µL of dioleoyl monoamine solution. Subsequently, the complex is diluted in 5% dextrose to 0.03 mg/mL of siRNA. Diluted complex is transferred to 25-50 kDa centrifugal filter unit and centrifuged for several minutes until the desired siRNA concentration in the retentate is reached.

Example 33

Determination of Particle Size and Zeta Potential of Nanoparticles

Dioleoyl crossamine/siRNA and dioleoyl monoamine/siRNA complexes are formulated as in Examples 6 and 9, and are diluted in 50 mM NaCl to appropriate concentrations. Samples are then added to a polystyrene cuvet and measured for particle size and zeta potential using a 90Plus/BI-MAS particles sizer. Observed particle sizes are between 80-400 nm and observed zeta potentials are between +10 to +40 mV.

Example 34

Synthesis of a di-[2-(oleoylamino)ethyl][2-[(methoxydodecaethyleneglycolcarbonylamino)ethyl]amine "mPEG-dioleoyl monoamine" (9)

Methoxy(dodecaethylene glycol) (MW 550, polydisperse, containing approximately 12 ethylene glycol units, 720 mg, 1.30 mmol) is dissolved in 8 mL of dry toluene. To this phosgene solution in toluene (4 mL of a 2 M solution, 8 mmol) is added. The reaction mixture is stirred at room temperature for 3 hours, and then concentrated in vacuuo at room temperature, affording 810 mg (1.31 mmol) of crude methoxy(dodecaethyleneglycol)chloroformate.

The above methoxy(dodecaethyleneglycol)chloroformate (810 mg, 1.31 mmol) is dissolved in 6.313 g of dry methylene chloride. dioleoyl monoamine is converted to the free base by treatment with potassium carbonate and extraction with methylene chloride. The organic phase is dried to give a dry oily material (700 mg, 1.04 mmol), which is re-dissolved in 6 mL dry methylene chloride. 5.66 g of the Methoxy(dodecaethylene glycol)chloroformate solution (1.04 mmol of mPEG chloroformate) is added with stirring to the dioleoyl monoamine free base solution. The mixture is stirred for 3 hours at room temperature, and then concentrated and purified chromatographically using silica gel (3 to 15% methanol in methylene chloride gradient elution). The purification affords PEG-dioleoyl monoamine (830 mg, 0.664 mmol).

Example 35

Preparation of a Fluorescent Taggant-Carrying Monoamine

The sulforhodamine B acyl chloride [Fluka, 115 mg, 0.2 mmol] is dissolved in 7 mL of dry chloroform. This solution is added to the well stirred solution of dioleoyl monoamine free base [140 mg, ca. 0.2 mmol, prepared as above by a treatment of the chloroform solution of its TFA salt with potassium carbonate] in 5 mL of dry chloroform. The mixture is stirred for 3 hours at room temperature, and then concentrated and purified chromatographically using 2000 micron thick layer silica gel preparative plate [subsequent elutions in 3 to 15% methanol in methylene chloride]. The purification affords [rhodamine B sulphonyl]dioleoyl monoamine (120 mg, 0.1 mmol).

(9)

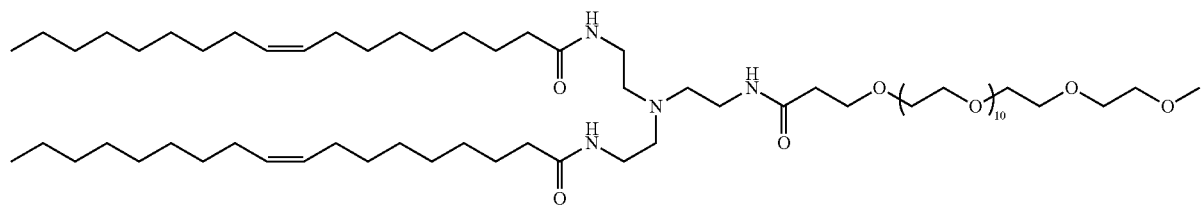

mPEG-dioleoyl monoamine

Example 36

Synthesis of α-lactobionylamido-ω-propionic acidundecaethyleneglycol-di-[2-(oleoylamino)ethyl](2-aminoethyl)amine "lactobionyl-dioleoyl monoamine" (10)

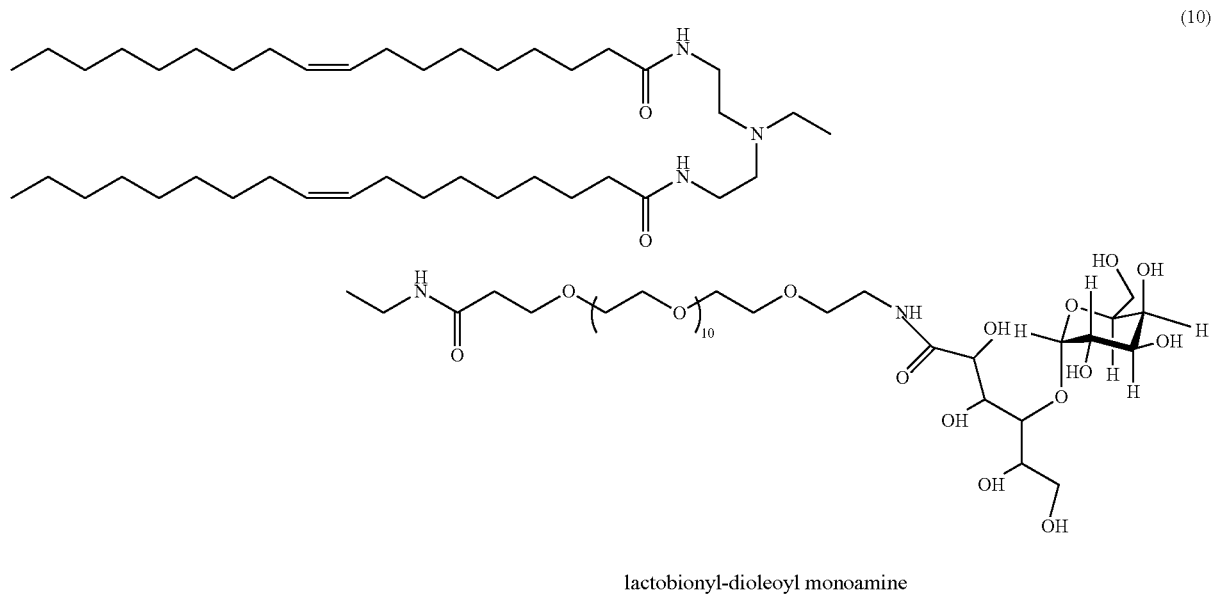

lactobionyl-dioleoyl monoamine

Fmocamino-ω-propionic acid-undecaethyleneglycol linker (Fmoc-PEG$_{11}$-COOH) (100 mg, 0.119 mmol) and p-nitrophenol (18 mg, 0.129 mmol) is dissolved in 1 mL methylene chloride. DCC (27 mg, 0.131 mmol) is dissolved in 1 mL methylene chloride and added to the stirring PEG/p-nitrophenol solution. The reaction is allowed to proceed at room temperature for 3 hours, after which DCU is removed using a 0.45 μm syringe filter. Dioleoyl monoamine is converted to the free base by treatment with potassium carbonate and extraction with methylene chloride. The organic phase is dried to give 75 mg (0.111 mmol) dry material which is redissolved in 0.5 mL methylene chloride. This solution is added to the p-nitrophenol-activated α-Fmocamino-ω-propionic acid-undecaethyleneglycol acid solution. The reaction is allowed to proceed for 18 hours at room temperature. The crude material is dried and re-dissolved in 1.8 mL dimethylformamide to which 200 μL piperidine is added. The Fmoc cleavage is allowed to proceed for 15 min, after which the dimethylformamide and piperidine are removed under high vacuum. α-Amino-ω-propionic acid-undecaethyleneglycol-di-[2-(oleoylamino)ethyl](2-aminoethyl)amine is isolated by separation on a silica gel column containing 80% methylene chloride in methanol, followed by 75%. The appropriate fractions are dried, giving 75 mg (0.59 mmol) of a brown oily material.

Lactobionic acid is first converted to the corresponding lactone by dehydration at 50° C. in methanol containing a drop of trifluoroacetic acid. α-Amino-ω-propionic acid-undecaethyleneglycol-di-[2-(oleoylamino)ethyl](2-aminoethyl)amine (50 mg, 0.039 mmol) is dissolved in 1.5 mL of methanol containing 15 μL diisopropylethylamine. To this stirring solution dry lactobionolactone (15 mg, 0.044 mmol) is added. The flask is sealed and the reaction is stirred at 60° C. for 20 hours. A small amount of precipitate is removed by syringe filtration and the α-lactobionylamido-ω-propionic acid-undecaethyleneglycol-di-[2-(oleoylamino)ethyl](2-aminoethyl)amine is dried under high vacuum to give 57 mg (0.035 mmol) of pure material.

Example 37

Synthesis of di-[2-(oleoylamino)ethyl][2-[ω-propionyl-LHRH-octaethyleneglycolpropionylamino)ethyl]amine "LHRH-dioleoyl monoamine" (11)

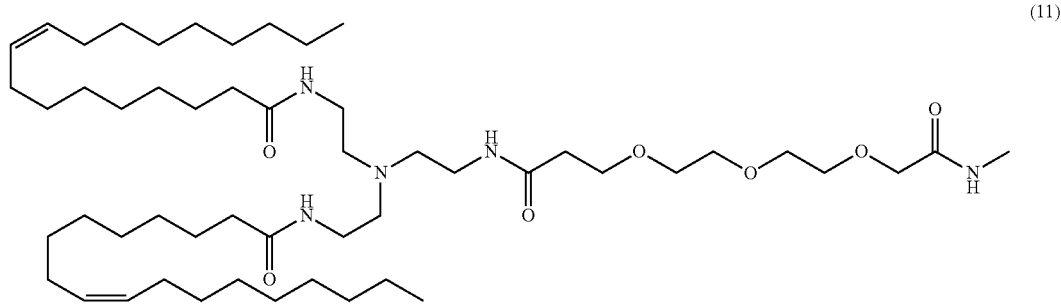

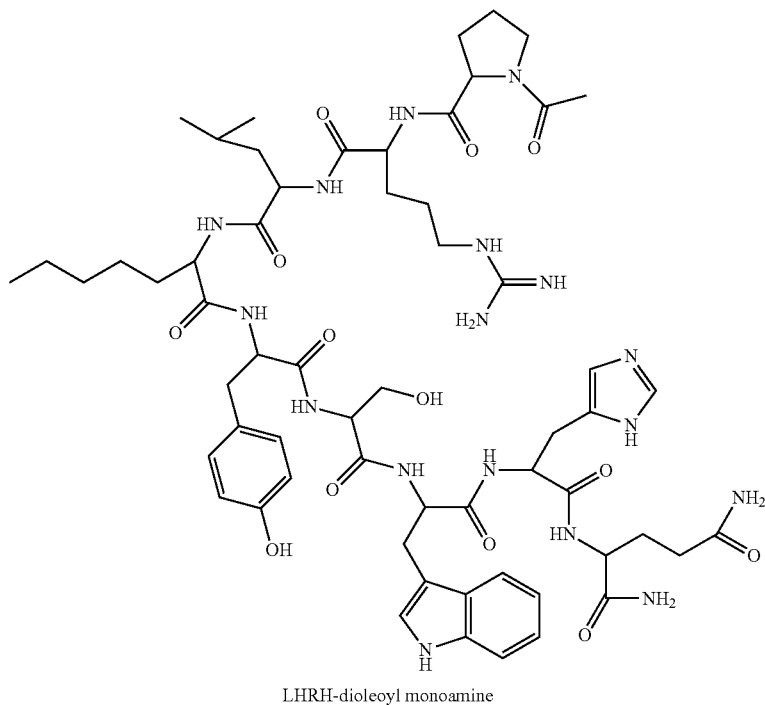

LHRH-dioleoyl monoamine

Octaethyleneglycoldipropionic acid (347 mg, 0.675 mmol) is dissolved in 8 mL of dry methylene chloride. To this p-nitrophenol (210 mg, 1.5 mmol) is added, followed by dicyclohexylcarbodiimide (DCC) (313 mg, 1.52 mmol). The next day, the reaction mixture is filtered from precipitated dicyclohexylurea, the filtrate concentrated and the title compound purified by chromatography on silica (first, elution with ether to remove the unreacted p-nitrophenol, and then with 4% methanol/methylene chloride).

The above octaethyleneglycoldipropionic acid di-p-nitrophenyl ester (510 mg, 0.68 mmol) is dissolved in 6 mL of dry methylene chloride. Di-[2-(oleoylamino)ethyl](2-aminoethyl)amine is converted to the free base by treatment with potassium carbonate and extraction with methylene chloride. The organic phase is dried to give a dry oily material (390 mg, 0.58 mmol), which is re-dissolved in 3 mL methylene chloride. The mixture is stirred overnight, and then purified chromatographically, using the same procedure as for the aforementioned di-p-nitrophenyl ester. After the unreacted di-[2-(oleoylamino)ethyl](2-aminoethyl)amine fraction, di-[2-(oleoylamino)ethyl][2-[ω-propionic acid octaethyleneglycolpropionylamino)ethyl]amine p-nitrophenolate (268 mg, 0.207 mmol) is collected.

Commercial LHRH peptide (sequence: Ac-QH-WSYKLRP-Am, 98 mg of TFA salt, 0.078 mmol) is dissolved in 2 mL of dry dimethylformamide and the solution is evaporated in high vacuum to dry the peptide. The residue is dissolved in 1 mL of dry dimethylformamide; the solution of the above di-[2-(oleoylamino)ethyl][2-[ω-propionic acid octaethyleneglycolpropionylamino)ethyl]amine p-nitrophenolate (135 mg, 0.104 mmol) in 1 mL dimethylformamide is added, followed by the addition of triethylamine (0.028 mL, 0.201 mmol). The stirred reaction mixture is kept at room temperature for 17 hours and then concentrated in vacuo. The purification of the target material is accomplished by reverse phase preparative chromatography using a C8 column and acetonitrile/water gradient elution [30% acetonitrile/water (0.1% TFA) to 90% over 15 min] affords 97 mg of di-[2-(oleoylamino)ethyl][2-[ω-propionyl-LHRH octaethyleneglycolpropionylamino)ethyl]amine.

Example 38

Synthesis of di-[2-(oleoylamino)ethyl][2-[ω-propionyl-RGD-octaethyleneglycolpropionylamino)ethyl] amine "RGD-dioleoyl monoamine" (12)

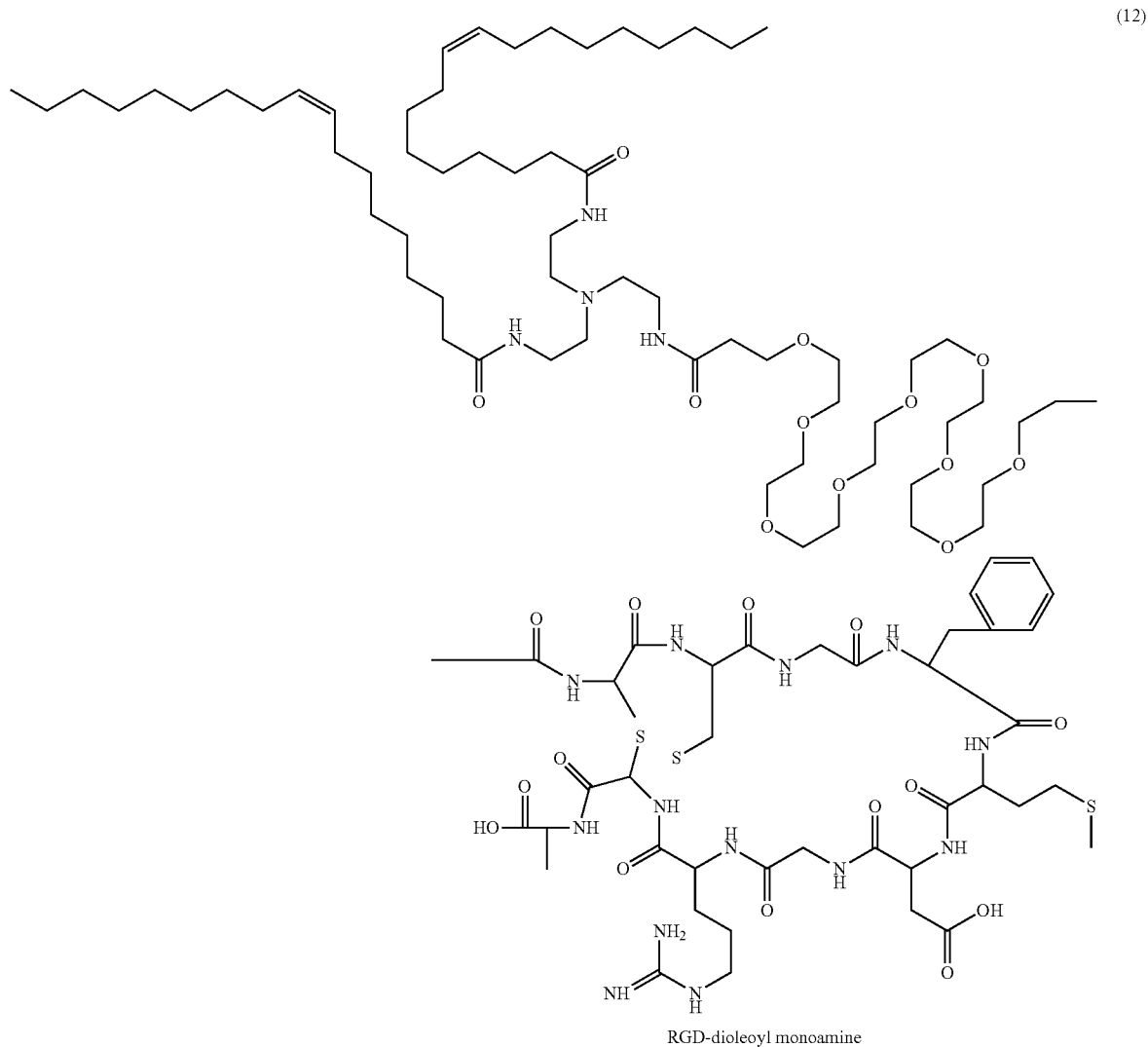

RGD-dioleoyl monoamine

Octaethyleneglycoldipropionic acid (347 mg, 0.675 mmol) is dissolved in 8 mL of dry methylene chloride. To this p-nitrophenol (210 mg, 1.5 mmol) is added, followed by dicyclohexylcarbodiimide (DCC) (313 mg, 1.52 mmol). The next day the reaction mixture is filtered from precipitated dicyclohexylurea, the filtrate concentrated and the title compound purified by chromatography on silica (first, elution with ether to remove the unreacted p-nitrophenol, and then with 4% methanol/methylene chloride).

The above octaethyleneglycoldipropionic acid di-p-nitrophenyl ester (510 mg, 0.68 mmol) is dissolved in 6 mL of dry methylene chloride. Dioleoyl monoamine is converted to the free base by treatment with potassium carbonate and extraction with methylene chloride. The organic phase is dried to give a dry oily material (390 mg, 0.58 mmol) which is redissolved in mL methylene chloride. The mixture is stirred overnight, and then purified chromatographically using the same procedure as for the aforementioned di-p-nitrophenyl ester. After the unreacted dioleoyl monoamine fraction, di-[2-(oleoylamino)ethyl][2-[ω-propionic acid octaethyleneglycol-propionylamino)ethyl]amine p-nitrophenolate (268 mg, 0.207 mmol) is collected.

Commercial RGD peptide [sequence: A*CRGDMFG*CA (2-9 disulfide bridge), 117 mg of TFA salt, 0.100 mmol] is dissolved in 3 mL of dry dimethylformamide and the solution evaporated in high vacuum to dry the peptide. The residue is dissolved in 3 mL of dry methanol; the solution of the above di-[2-(oleoylamino)ethyl][2-[ω-propionic acid octaethyleneglycol-propionylamino)ethyl]amine p-nitrophenolate (135 mg, 0.104 mmol) in 3 mL methylene chloride is added, followed by the addition of Hunig's base (0.065 mL, 0.370 mmol). The reaction mixture is stirred at room temperature for 72 hours and then concentrated in vacuuo. The purification of the target material is accomplished by reverse phase preparative chromatography using a C8 column and acetonitrile/water gradient elution affording 43 mg (0.020 mmol) of di-[2-(oleoylamino)ethyl][2-[ω-propionyl-RGD-octaethyleneglycolpropionylamino)ethyl]amine.

Example 39

Preparation of Complexed siRNA with Dioleoyl Monoamine and mPEG-Dioleoyl Monoamine The siRNA used is a double stranded sequence of nucleotides intended to produce a knockdown of endogenous vascular endothelial growth factor (VEGF) transcript and protein levels. The cationic lipids used are mixtures of dioleoyl monoamine (Example 3) and mPEG-dioleoyl monoamine (Example 34). To prepare the liposomes, the lipids are dissolved and mixed in chloroform to assure a homogenous mixture. The organic solvent is removed by rotary evaporation yielding a thin lipid film on the walls of a round-bottom flask. Chloroform is further evaporated by placing the round-bottom flask on a vacuum pump overnight. The resulting lipid film is rehydrated with distilled water at a desired concentration and vortexed vigorously for several minutes. The solution is placed in a bath sonicator for 1 hour and is then filtered through a 200 nm sterile syringe filter to give the final liposomal solution. siRNA dissolved in water is added to the liposome solution.

Example 40

Preparation of Encapsulated siRNA with Dioleoyl Monoamine and mPEG-Dioleoyl Monoamine This example illustrates liposomal encapsulation of siRNA using mPEG-dioleoyl monoamine. The siRNA used is a double stranded sequence of nucleotides intended to produce a knockdown of endogenous target transcript and protein levels. The cationic lipids used are mixtures of dioleoyl monoamine (Example 3) and mPEG-dioleoyl monoamine (Example 34). To prepare the encapsulation liposomes, the lipids are dissolved and mixed in chloroform to assure a homogenous mixture. The organic solvent is removed by rotary evaporation yielding a thin lipid film on the walls of a round-bottom flask. Chloroform is further evaporated by placing the round-bottom flask on a vacuum pump overnight. The resulting lipid film is dissolved initially in 100% ethanol then brought to 50%. siRNA dissolved in water is added to the liposomes in ethanol solution. Ethanol is evaporated from the liposomes/siRNA mixture by a rotary evaporation system. The resulting nanoparticles are suspended in 5% dextrose by adding an equal amount of 10% dextrose to the encapsulated siRNA particles.

Example 41

Figure 5A:
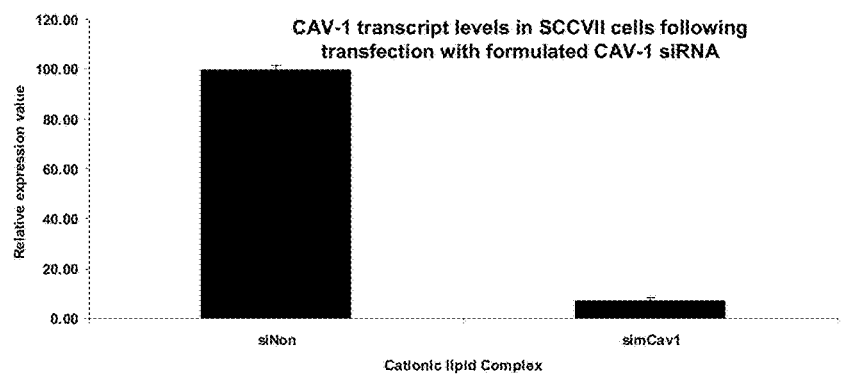
FIG. 5A and FIG. 5B are graphs showing relative transcript levels of Caveolin-1 (Cav-1) in cell culture medium following an in vitro transfection using murine squamous cell carcinoma VII (SCCVII) cells. Cells were transfected with siRNA and dioleoyl monoamine/mPEG-dioleoyl monoamine complexes (FIG. 5A) or encapsulated siRNA with dioleoyl monoamine/mPEG-dioleoyl monoamine (FIG. 5B).

Transfection Activity siRNA and Dioleoyl Monoamine/mPEG-Dioleoyl Monoamine Complexes The transfection activity of siRNA and dioleoyl monoamine/mPEG-dioleoyl monoamine complexes is determined in vitro as follows. The siRNA used is a double stranded sequence of nucleotides intended to produce a knockdown of endogenous Caveolin-1 (Cav-1) transcript levels. The cationic lipids used are mixtures of dioleoyl monoamine (Example 3) and mPEG-dioleoyl monoamine (Example 34). To prepare the liposomes, the lipids are dissolved and mixed in chloroform to assure a homogenous mixture. The organic solvent is removed by rotary evaporation yielding a thin lipid film on the walls of a round-bottom flask. Chloroform is further evaporated by placing the round-bottom flask on a vacuum pump overnight. The resulting lipid film is rehydrated with distilled water at a desired concentration and vortexed vigorously for several minutes. The solution is placed in a bath sonicator for 1 hour and is then sterile syringe filtered through a 200 nm syringe filter to give the final liposomal solution. siRNA dissolved in water is added to the liposome solution. The resulting nanoparticles are suspended in 5% dextrose by adding an equal amount of 10% dextrose to the complexed siRNA particles. SCCVII cells ($0.5 \times 10^5$ cells/well) are seeded into 24-well tissue culture plates in 10% FBS. Each well is incubated for 6 hours with 0.5 µg of complexed siRNA in absence or presence of FBS in a total volume of 250 µL DMEM. When the incubation period is concluded for the cells lacking FBS in their medium, 250 µL of DMEM supplemented with 20% FBS is added to the transfected cells and incubated further for another 40 hours. To cells with FBS in their transfection medium, 250 µL of DMEM supplemented with 10% FBS is added to the transfected cells and incubated further for another 40 hours. At the end of the incubation period, knockdown of Cav-1 transcript is measured in cell lysates. To perform Cav-1 transcript analysis, cells are lysed using Tri-reagent and then quantified for the level of Cav-1 transcript using a qRT-PCR detection kit. Cav-1 transcript is inhibited up to 90% compared to a non-silencing control (FIG. 5A).

Example 42

Figure 5B:
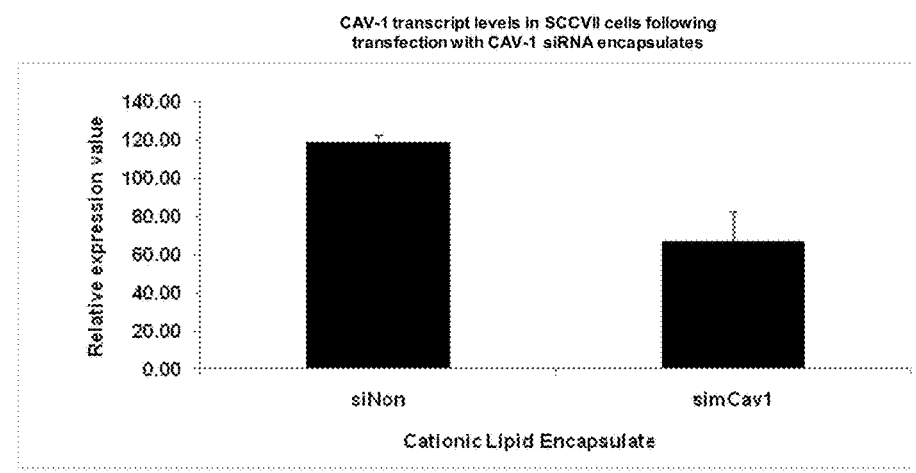

Transfection Activity of Encapsulated siRNA with Dioleoyl Monoamine/mPEG-Dioleoyl Monoamine The transfection activity of encapsulated siRNA with dioleoyl monoamine/mPEG-dioleoyl monoamine is determined in vitro as follows. The siRNA used is a double stranded sequence of nucleotides intended to produce a knockdown of endogenous Caveolin-1 (Cav-1) transcript levels. The cationic lipids used are mixtures of dioleoyl monoamine (Example 3) and mPEG-dioleoyl monoamine (Example 34). To prepare the encapsulation liposomes, the lipids are dissolved and mixed in chloroform to assure a homogenous mixture. The organic solvent is removed by rotary evaporation yielding a thin lipid film on the walls of a round-bottom flask. Chloroform is further evaporated by placing the round-bottom flask on a vacuum pump overnight. The resulting lipid film is dissolved initially in 100% ethanol then brought to 50%. siRNA dissolved in water is added to the liposomes in ethanol solution. Ethanol is evaporated from the liposomes/siRNA mixture by a rotary evaporation system. The resulting nanoparticles are suspended in 5% dextrose by adding an equal amount of 10% dextrose to the encapsulated siRNA particles. SCCVII cells ($0.5 \times 10^5$ cells/well) are seeded into 24-well tissue culture plates in 10% FBS. Each well is incubated for hours with 0.5 µg of encapsulated siRNA in absence or presence of FBS in a total volume of 250 µL DMEM. When the incubation period is concluded for the cells lacking FBS in their medium, 250 µl of DMEM supplemented with 20% FBS is added to the transfected cells and incubated further for another 40 hours. To cells with FBS in their transfection medium, 250 µL of DMEM supplemented with 10% FBS is added to the transfected cells and incubated further for another 40 hours. At the end of the incubation period, knockdown of Cav-1 transcript is measured in the cell lysates. For Cav-1 transcript analysis, cells are lysed using Tri-reagent and then quantified for the level of VEGF transcript using a qRT-PCR detection kit. Cav-1 transcript is inhibited up to 45% compared to a non-silencing control (See FIG. 5B).

Example 43

Figure 6:
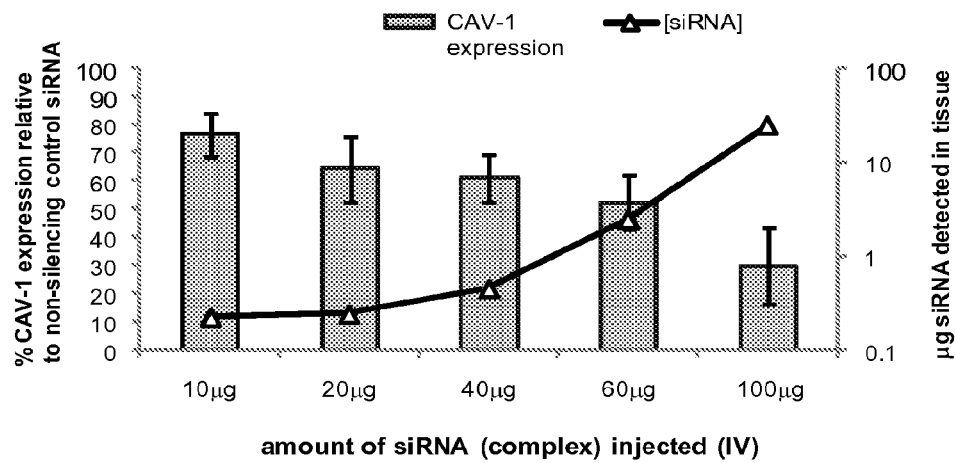
FIG. 6 shows dose dependent (10 µg-100 µg), siRNA specific transcript knockdown (Cav-1) in the lung of mice following a single iv injection of siRNA complexed with dioleoyl monoamine and mPEG-dioleoyl monoamine.

Caveolin-1 Transcript Knockdown in Lung Following Administration of siRNA Complexed with Dioleoyl Monoamine and mPEG-Dioleoyl Monoamine Female ICR mice (17-22 g) are injected intravenously (IV) with 200 µL of previously formulated siRNA targeting Caveolin-1 (Cav-1) transcript. siRNA complexes contain 10:1 mixture of dioleoylmonoamine and mPEG-dioleoyl monoamine with 100, 60, 40, 20, or 10 µg of siRNA (20:1 N:P ratio) (ref. Example 9). At 48 hours after injection the animals are euthanized and lungs are harvested for target Cav-1 transcript analysis and siRNA quantification using qRT-PCR. The CAV-1 transcript levels (normalized to β-actin as an internal control) are expressed as a percent expression relative to untreated control animals. Results indicate a dose-dependent reduction of Cav-1 transcript levels in lungs of animals ranging from >60% in animals given 100 µg siRNA to ~13% in animals given 10 µg siRNA. Quantification of the injected siRNA indicates a dose dependent increase in the absolute amount of siRNA distributed to the lungs (FIG. 6). At the lowest dose ~5% of the injected siRNA is distributed to the lungs. At the highest dose ~50% of the injected siRNA is distributed to the lungs. The number of animals ("n") is 6 for each group.

Example 44

Figure 7:
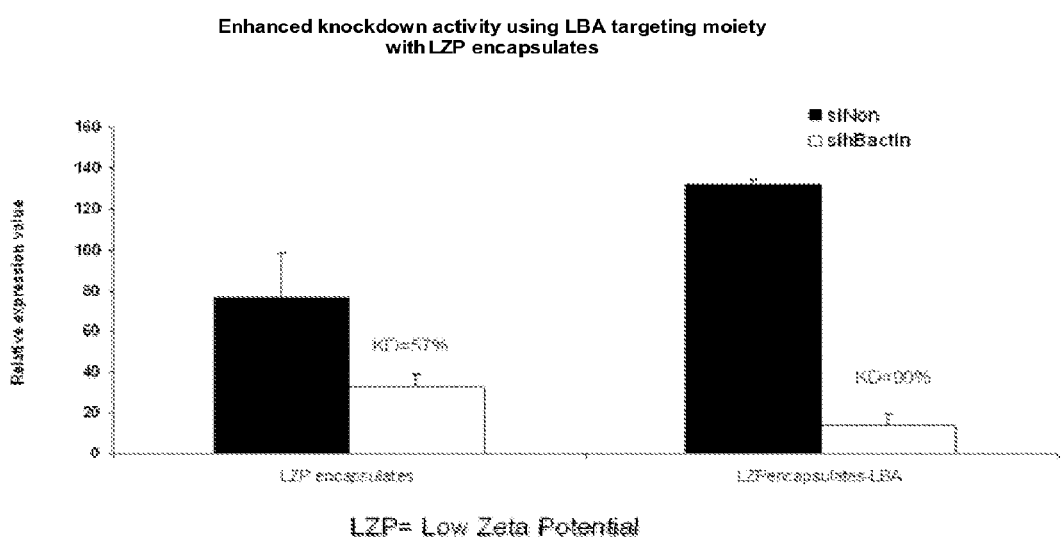
FIG. 7 shows protein expression levels of β-actin in cell culture medium following an in vitro transfection using HepG2 cells. Cells were transfected with siRNA formulated with dioleoyl monoamine/lactobionyl-dioleoyl monoamine.

Transfection Activity of Encapsulated siRNA with Dioleoyl Monoamine/Lactobionyl-Dioleoyl Monoamine The transfection activity of encapsulated siRNA with dioleoyl monoamine/lactobionyl-dioleoyl monoamine is determined in vitro as follows. The siRNA used is a double stranded sequence of nucleotides intended to produce a knockdown of β-actin transcript levels. The cationic lipids used are mixtures of dioleoyl monoamine (Example 3) and lactobionyl-dioleoyl monoamine (Example 35). To prepare the encapsulation liposomes, the lipids are dissolved and mixed in chloroform to assure a homogenous mixture. The organic solvent is removed by rotary evaporation yielding a thin lipid film on the walls of a round-bottom flask. Chloroform is further evaporated by placing the round-bottom flask on a vacuum pump overnight. The resulting lipid film is dissolved initially in 100% ethanol then brought to 50%. siRNA dissolved in water is added to the liposomes in ethanol solution. Ethanol is evaporated from the liposomes/siRNA mixture by a rotary evaporation system. The resulting nanoparticles are suspended in 5% dextrose by adding an equal amount of 10% dextrose to the encapsulated siRNA particles. Hepa16 cells ($0.5 \times 10^5$ cells/well) are seeded into 24-well tissue culture plates in 10% FBS. Each well is incubated for hours with 0.5 µg of encapsulated siRNA in absence or presence of FBS in a total volume of 250 µL DMEM. When the incubation period is concluded for the cells lacking FBS in their medium, 250 µl of DMEM supplemented with 20% FBS is added to the transfected cells and incubated further for another 40 hours. To cells with FBS in their transfection medium, 250 µL of DMEM supplemented with 10% FBS is added to the transfected cells and incubated further for another 40 hours. At the end of the incubation period, knockdown of β-actin transcript is measured in the cell lysates. For transcript analysis, cells are lysed using Tri-reagent and then quantified for the level of β-actin transcript using a qRT-PCR detection kit. β-actin transcript is inhibited to 90% compared to a non-silencing control, while samples containing identical particles lacking the LBA ligand showed only 57% inhibition compared to a non-silencing control (FIG. 7).

Example 45

Figure 8:
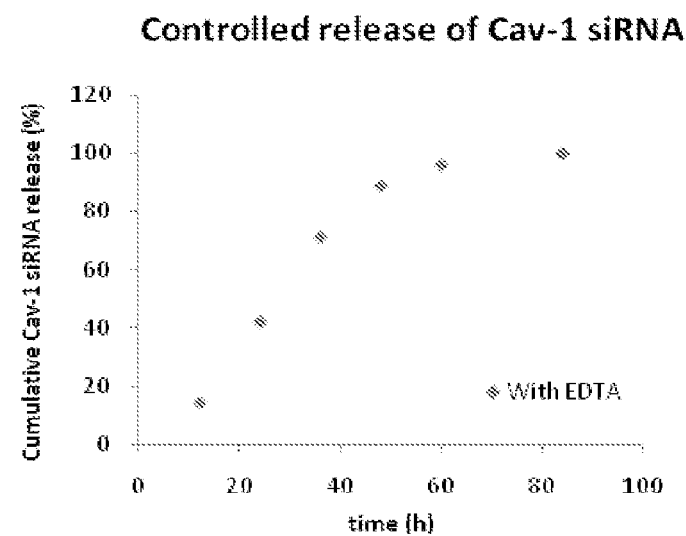
FIG. 8 shows controlled-release of Cav-1 siRNA complexed with dioleoyl monoamine from alginate gels with and without EDTA.
Figure 8:
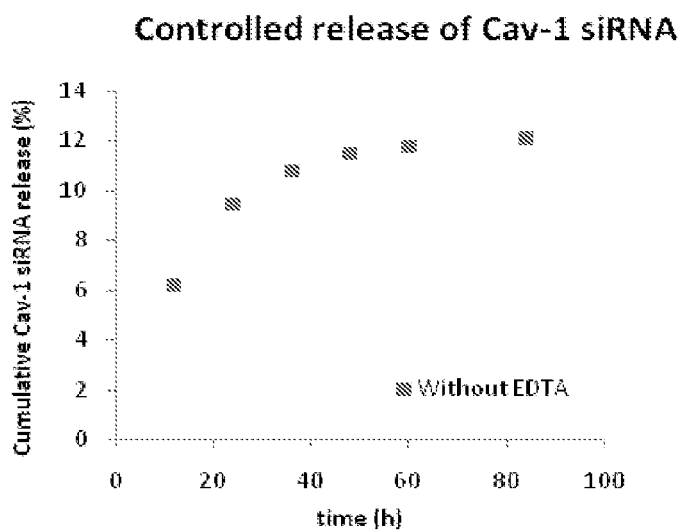

Controlled Release of siRNA Complexed with Dioleoyl Monoamine from Crosslinked Gel siRNA complexed with dioleoyl monoamine is formulated as described in Example 39 containing 50 µg Cav-1 siRNA and 1.4 µg dioleoyl monoamine in a volume of 50 µL. Sodium alginate (Type A) is dissolved in water to give a 2% solution. An alginate solution (100 µL) is added to a single well of a 96-well plate followed by 50 µL of the dioleoyl monoamine/Cav-1 siRNA solution. After thorough mixing, 50 µL of a 0.68 M $CaCl_2$ solution is added to the previous mixture to crosslink the gel. One hundred µL of water or 0.1 M EDTA (which serves to break down the gel by complexing the $Ca^{2+}$ ions) is then added to ensure complete submersion of the gel in aqueous solution. At the prescribed time points, the supernatants are removed (200 µL) and replaced with fresh 200 µL water or 0.1 M EDTA. After 84 hours, all collected samples are assayed for Cav-1 siRNA content using qRT-PCR. The siRNA amounts collected at each time point are summed in order to determine amount released over time. In samples that have the addition of EDTA, 100% of the loaded dioleoyl monoamine formulated siRNA is released after 84 hours. In samples which do not contain EDTA, a significantly slower release kinetic was observed with <20% of the total siRNA loaded being released by 84 hours (FIG. 8).

Example 46

Figure 9:
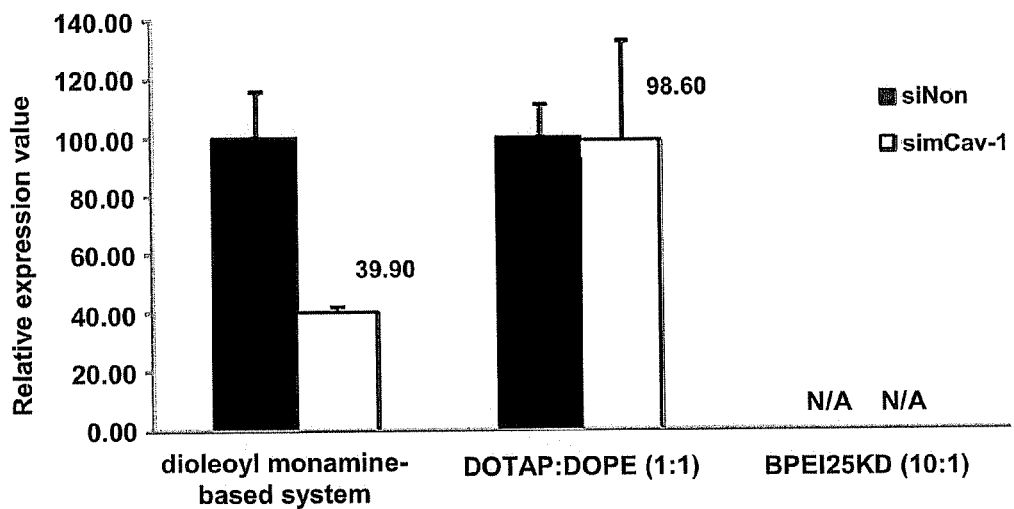
FIG. 9 shows siRNA specific transcript knockdown (Cav-1) in the lung and liver of mice following a single iv injection of siRNA complexed with dioleoyl monoamine and mPEG-dioleoyl monoamine, or with DOTAP:DOPE (1:1), or with BPEI.
Figure 9:
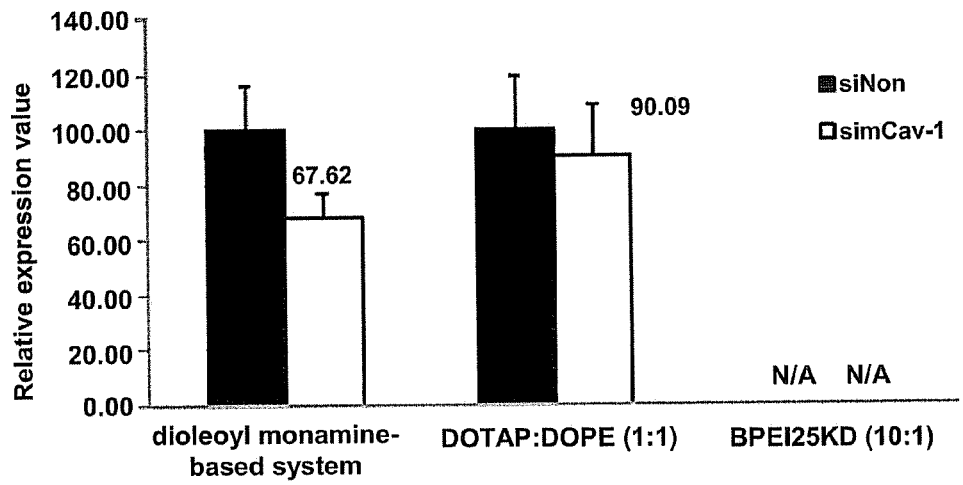

Caveolin-1 Transcript Knockdown in Lung and Liver Following Administration of siRNA Complexed with Dioleoyl Monoamine and mPEG-Dioleoyl Monoamine in Comparison to siRNA Complexed with Other Commercially Available Cationic Lipid and Cationic Polymeric Systems Female ICR mice (17-22 g) are injected intravenously (IV) with 200 µL of a previously formulated siRNA targeting Caveolin-1 (Cav-1) transcript. siRNA complexes contain 10:1 mixture of dioleoyl monoamine and mPEG-dioleoyl monoamine with 40 µg siRNA (20:1 N:P ratio) (ref. Example 39). In addition, siRNA is formulated with either DOTAP:DOPE (1:1) at a 20:1 N:P ratio, or with 25 kDa branched PEI (10:1). A total of 40 µg siRNA formulated with DOTAP:DOPE (in 200 µL) is injected IV into mice or a total of 20 µg of siRNA formulated with branched PEI (in 100 µL) is injected IV. Branched PEI is used in a lower amount in order to try and mitigate the known toxicities associated with this formulation. At 48 hours after injection animals are euthanized and lungs and livers are harvested for target Cav-1 transcript analysis and siRNA quantification using qRT-PCR. The CAV-1 transcript levels (normalized to β-actin as an internal control) are expressed as a percent expression relative to untreated control animals. The number of animals ("n") is 5 for each group. Results indicate significant (~60%) transcript knockdown in CAV-1 expression in lung tissue and a ~33% transcript knockdown in liver (FIG. 9). No significant transcript knockdown was noted for the DOTAP:DOPE formulated siRNA. For the branched PEI formulated siRNA the animals died due to toxicity associated with the formulation prior to tissue harvest and could therefore not be analyzed; the dioleoyl monoamine/mPEG-dioleoyl monoamine formulated siRNA and the DOTAP:DOPE formulated siRNA were administered with little toxicity.

Example 47

Figure 10:
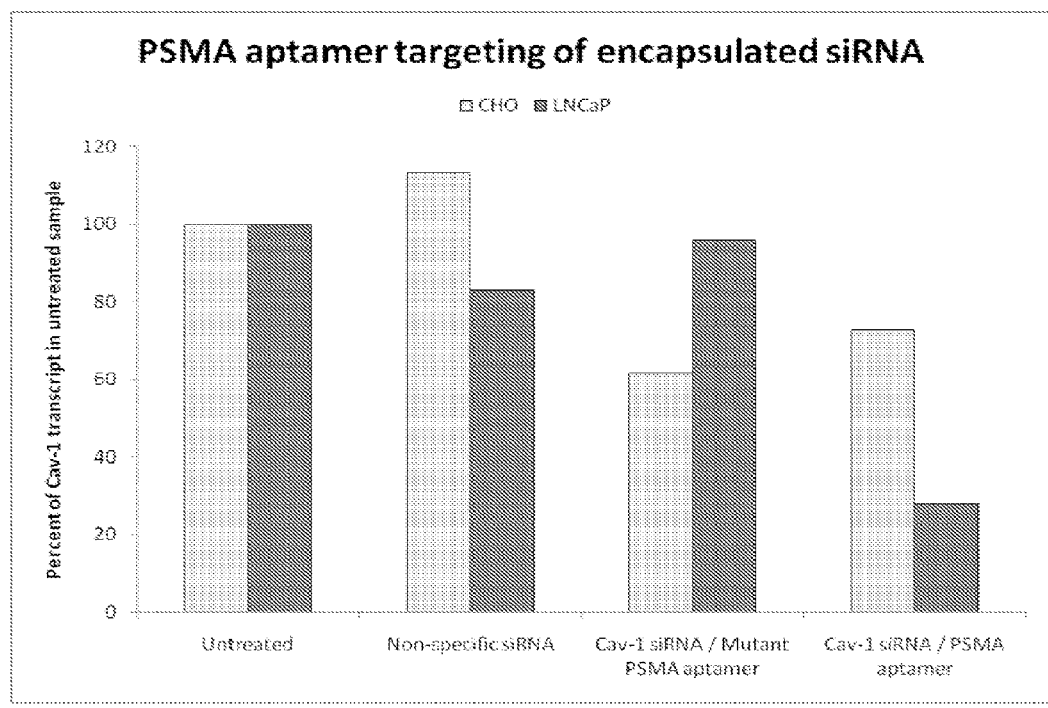
FIG. 10 shows transfection activity of encapsulated siRNA with dioleoyl crossamine/prostate specific membrane antigen (PSMA) targeting aptamer.

Transfection Activity of Encapsulated siRNA with Dioleoyl Crossamine/PSMA Targeting Aptamer The transfection activity of encapsulated dsRNA with dioleoyl crossamine/PSMA targeting aptamer is determined in vitro as follows. The siRNA used is a double stranded sequence of nucleotides intended to produce a knockdown of Cav-1 transcript levels. The cationic lipid used is dioleoyl crossamine (Example 1). The RNA aptamer targets the prostate specific membrane antigen and includes a ssRNA uridine tail on the 3' end (PSMA aptamer sequence: 5' GGGAGGAC-GAUGCGGAUCAGCCAUGUUUACGU-CACUCCUAAUUUUUUUUUUUUUUUUUUUU 3'). A non-binding mutant aptamer is included as a negative control (mutant PSMA aptamer sequence: 5' GGGAGGAC-GAUGCGGAUCAGCCAUCCUUACGU-CACUCCUAAUUUUUUUUUUUUUUUUUUUU 3'). Encapsulated liposomes are prepared as described in Example 45. Targeted liposomes are prepared by adding the RNA aptamer to the encapsulated liposomes and incubating the mixture at room temperature for 30 minutes. LNCaP cells ($2.5 \times 10^5$ cells/well) are seeded into 12 well tissue culture plates in 10% FBS. Each well is incubated for 5 hours with 0.1 μg of targeted liposomes or non-targeted control liposomes (complexed with a non-binding mutant aptamer) in the absence of FBS in a total volume of 500 μL RPMI 1640. When the incubation period is concluded, the media is replaced with 500 μL of RPMI 1640 supplemented with 10% FBS and incubated for an additional 40 hours. At the end of the incubation period, knockdown of the Cav-1 transcript is measured in the cell lysates. For transcript analysis, cells are lysed and total RNA is purified using Qiagen's RNEasy kit (Qiagen product number: 74106). Transcript levels for Cav-1 and GAPDH (internal control) were quantified using a qRT-PCR detection kit. Cav-1 transcript levels are depleted in cells treated with PSMA targeting liposomes by 70% compared to non-silencing control. This is in contrast to cells treated with the non-targeting mutant PSMA aptamer, which show no depletion of Cav-1 transcripts compared to non-silencing controls. Treatment of cells lacking the prostate specific membrane antigen (Chinese hamster ovary cells) show similar levels of Cav-1 depletion (~35%) compared to non-silencing controls independent of targeting aptamer identity (FIG. 10)

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

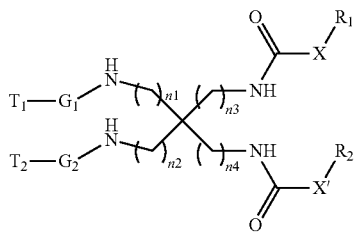

wherein n1, n2, n3, and n4 are independently 1, 2, 3, or 4;

X and X' are independently a bond, oxygen, or nitrogen;

$R_1$ and $R_2$ are independently $C_8$-$C_{25}$ hydrocarbon groups optionally containing from 1-4 double or triple bonds; and $T_1$ and $T_2$ are independently hydrogen or a targeting ligand;

$G_1$ and $G_2$ are independently bond or a polymer moiety, where at least one of $T_1$ and $T_2$ is a targeting ligand.

2. A compound according to claim 1, wherein n1, n2, n3, and n4 are all 1, and both X and X' are bonds.

3. A compound according to claim 1, wherein $R_1$ and $R_2$ are independently $C_8$-$C_{25}$ hydrocarbon groups containing 1 or 2 double bonds.

4. A compound according to claim 1, wherein at least one of $G_1$ and $G_2$ is a polyoxyalkylene, polyvinylpyrrolidone, polyacrylamide, polydimethylacrylamide, polyvinyl alcohol, dextran, poly(L-glutamic acid), styrene maleic anhydride, poly-N-(2-hydroxypropyl)methacrylamide, or polydivinylether maleic anhydride.

5. A compound according to claim 4, wherein the polymer comprises at least one linker group between polymer units.

6. A compound according to claim 5, wherein the polymer is a polyoxyalkylene where the oxyalkylene groups are independently straight or branched chain polyoxyalkylene groups having from 2-5 carbon atoms in their repeating units.

7. A formulation comprising a compound of claim 1 and a molecule selected from the group consisting of:

(a) ribosomal RNA; antisense polynucleotides of RNA or DNA; ribozymes; siRNA; shRNA; miRNA; and polynucleotides of genomic DNA, cDNA, or mRNA that encode for a therapeutically useful protein;

(b) an aptamer; or (c) proteins, peptides, cholesterol, hormones, small molecule pharmaceutical compounds, vitamins, and co-factors.

8. A method for in vivo delivery of a molecule, said method comprising administering to a mammalian subject a therapeutically effective amount of a formulation of claim 7.

* * * * *

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(9)
<223> OTHER INFORMATION: C-terminal amidation

<400> SEQUENCE: 1

Gln His Trp Ser Tyr Lys Leu Arg Pro
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: DISULFID
<222> LOCATION: (2)..(9)

<400> SEQUENCE: 2

Ala Cys Arg Gly Asp Met Phe Gly Cys Ala
1               5                   10
```

```
<210> SEQ ID NO 3
<211> LENGTH: 61
<212> TYPE: RNA
<213> ORGANISM: Artificial Sequence
<220> FEATURE:
<223> OTHER INFORMATION: Synthetic

<400> SEQUENCE: 3
gggaggacga ugcggaucag ccauguuuac gucacuccua auuuuuuuuu uuuuuuuuuu    60
u                                                                   61

<210> SEQ ID NO 4
<211> LENGTH: 61
<212> TYPE: RNA
<213> ORGANISM: Artificial Sequence
<220> FEATURE:
<223> OTHER INFORMATION: Synthetic

<400> SEQUENCE: 4
gggaggacga ugcggaucag ccauccuuac gucacuccua auuuuuuuuu uuuuuuuuuu    60
u                                                                   61
```